US012735446B2

(12) United States Patent
Chiba et al.

(10) Patent No.: US 12,735,446 B2
(45) Date of Patent: Sep. 15, 2026

(54) ALKOXYPHENYL DERIVATIVES, PROTECTED NUCLEOSIDES AND PROTECTED NUCLEOTIDES, METHOD FOR PRODUCING OLIGONUCLEOTIDES, AND METHOD FOR REMOVING SUBSTITUENTS

(71) Applicant: FUJIMOTO CHEMICALS CO., LTD., Osaka (JP)

(72) Inventors: Kazuhiro Chiba, Tokyo (JP); Yohei Okada, Tokyo (JP); Hideaki Umemoto, Hyogo (JP); Takuya Onaka, Hyogo (JP)

(73) Assignee: FUJIMOTO CHEMICALS CO., LTD., Osaka (JP)

( * ) Notice: Subject to any disclaimer, the term of this patent is extended or adjusted under 35 U.S.C. 154(b) by 349 days.

(21) Appl. No.: 18/603,643

(22) Filed: Mar. 13, 2024

(65) Prior Publication Data

US 2024/0239833 A1 Jul. 18, 2024

Related U.S. Application Data

(62) Division of application No. 17/261,481, filed as application No. PCT/JP2019/008113 on Mar. 1, 2019, now Pat. No. 12,209,106.

(30) Foreign Application Priority Data

Jul. 20, 2018 (JP) ................................ 2018-136466

(51) Int. Cl.
*C07H 21/04* (2006.01)
*C07H 1/02* (2006.01)

(52) U.S. Cl.
CPC ............... *C07H 21/04* (2013.01); *C07H 1/02* (2013.01)

(58) Field of Classification Search
CPC .. C07D 401/12; C07D 243/08; C07D 261/12; C07K 14/70578; C07K 19/00; C08F 20/26; C07H 1/00; C07H 1/02; C07H 19/067; C07H 19/073; C07H 19/167; C07H 19/173; C07H 21/00; C07H 21/02; C07H 21/04
USPC ........................................................ 536/23.1
See application file for complete search history.

(56) References Cited

U.S. PATENT DOCUMENTS

| | | | |
|---|---|---|---|
| 3,927,082 | A | 12/1975 | Katori et al. |
| 5,298,652 | A | 3/1994 | Carson et al. |
| 2003/0153001 | A1 | 8/2003 | Soane et al. |
| 2004/0058006 | A1 | 3/2004 | Barry et al. |
| 2005/0153876 | A1 | 7/2005 | Cameron et al. |
| 2006/0194927 | A1 | 8/2006 | Gin et al. |
| 2008/0112544 | A1 | 5/2008 | Kim et al. |
| 2008/0112546 | A1 | 5/2008 | Fletcher et al. |
| 2012/0296074 | A1 | 11/2012 | Hirai et al. |
| 2019/0169223 | A1 | 6/2019 | Sugawara |

FOREIGN PATENT DOCUMENTS

| | | | |
|---|---|---|---|
| CN | 1839150 | A | 9/2006 |
| CN | 103476784 | A | 12/2013 |
| DE | 2407016 | A | 9/1974 |
| EP | 1025066 | A2 | 8/2000 |
| EP | 1656390 | A2 | 5/2006 |
| EP | 1758859 | A1 | 3/2007 |
| EP | 2147925 | A1 | 1/2010 |
| EP | 2711370 | A1 | 3/2014 |
| FR | 2217316 | A | 9/1974 |

(Continued)

OTHER PUBLICATIONS

Tsunashima et al.; Fullerene Nanowires: Self-Assembled Structures of a Low-Molecular-Weight Organogelator Fabricated by the Langmuir-Blodgett Method; Chem. Eur. J. 2008, 14, 8169-8176; 8 pages.

(Continued)

*Primary Examiner* — Robert B Mondesi
*Assistant Examiner* — Mohammad Y Meah
(74) *Attorney, Agent, or Firm* — Meunier Carlin & Curfman LLC

(57) ABSTRACT

The present invention relates to an alkoxyphenyl derivative capable of synthesizing an oligonucleotide by a quicker liquid phase synthesis method than in the prior art, a protected nucleoside and a protected nucleotide to which the alkoxyphenyl derivative is bonded, a method for producing an oligonucleotide using the same, and a method for selectively removing the alkoxyphenyl derivative moiety and the like.

A compound represented by the general formula (1) or a derivative thereof:

[Chemical Formula 1]

(1)

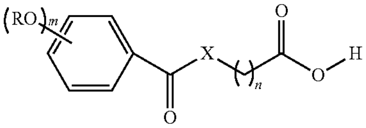

(In the formula,

R each independently represents an optionally substituted alkyl group having 10 to 40 carbons.

m represents an integer between 1 and 5. When m is 2 or more, a plurality of ROs may be the same or different.

X represents O, S, NH, or $NR^N$.

n represents an integer from 1 to 4.

$R^N$ represents an optionally substituted alkyl group having 1 to 6 carbons.)

10 Claims, No Drawings

(56) References Cited

FOREIGN PATENT DOCUMENTS

| | | | |
|---|---|---|---|
| GB | 1418595 | A | 12/1975 |
| JP | 49-124043 | A | 11/1974 |
| JP | 49-126644 | A | 12/1974 |
| JP | 2004-262809 | A | 9/2004 |
| JP | 2007-536200 | A | 12/2007 |
| JP | 2010-275254 | A | 12/2010 |
| JP | 5548852 | B2 | 7/2014 |
| JP | 2016179993 | A | 10/2016 |
| JP | 2018090598 | A | 6/2018 |
| WO | 1999/019276 | A2 | 4/1999 |
| WO | 2004/081979 | A2 | 9/2004 |
| WO | 2005000878 | A2 | 1/2005 |
| WO | 2005/118542 | A1 | 12/2005 |
| WO | 2012157723 | A1 | 11/2012 |
| WO | 2017086397 | A1 | 5/2017 |

OTHER PUBLICATIONS

S.L.Beaucage, D.E. Bergstrom, G. D. Glick, R.A. Jones; Current Protocols in Nucleic Acid Chemistry; John Wiley & Sons (2000).

"Genome Chemistry—A Scientific Approach Utilizing Artificial Nucleic Acids" edited by Mitsuo Sekine, Isao Saito, Koudansha Scientific Co., Ltd. (2003), 127 pages. English Excerpt 31 pages.

Chen, Chih-Hau, et al. "Convergent solution phase synthesis of chimeric oligonucleotides by a 2+2 and 3+3 phosphoramidite strategy." Australian journal of chemistry 63.2 (2010): 227-235.

Matsuno, Yuki, et al. "Synthetic method for oligonucleotide block by using alkyl-chain-soluble support." Organic letters 18.4 (2016): 800-803.

Office Action issued for corresponding Japanese Patent Application No. 2018-136466, dated May 8, 2020.

Office Action issued for corresponding Japanese Patent Application No. 2018-136466, dated Aug. 21, 2019.

International Search Report and Written Opinion issued for Application No. PCT/JP2019/008113, dated Jan. 23, 2020.

International Preliminary Report on Patentability issued for Application No. PCT/JP2019/008113, dated Jan. 26, 2021.

Extended European Search Report issued in Application No. 19838154.3-1109/3725399; dated Mar. 22, 2022; 8 pages.

ALKOXYPHENYL DERIVATIVES, PROTECTED NUCLEOSIDES AND PROTECTED NUCLEOTIDES, METHOD FOR PRODUCING OLIGONUCLEOTIDES, AND METHOD FOR REMOVING SUBSTITUENTS

TECHNICAL FIELD

The present invention relates to an alkoxyphenyl derivative cap able of synthesizing an oligonucleotide by a liquid phase synthesis method, a protected nucleoside and a protected nucleotide bonded there to, a simple constructible oligonucleotide production method using the same, and a method for removing a selective alkoxyphenyl derivative moiety of a protected nucleoside or protected nucleotide to which an alkoxyphenyl derivative is bonded, and the like.

BACKGROUND OF THF INVENTION

Recently, oligonucleotides can be synthesized by sequentially linking nucleotides serving as raw materials, but in the case of synthesizing oligonucleotides of about 20 mer or more, a blockmer synthesis method in which a building block group of 2 to 3 mer nucleotides is prepared in advance and a product having a desired chain length is obtained by repeating the linking, or a unit coupling (fragment condensation) synthesis method in which an oligonucleotide is obtained by linking between oligonucleotides of about 10 bases or more is also utilized (for example, Non-Patent Documents 1 to 3). A method for solid phase synthesis of oligonucleotides using a phosphoroamidite method has a problem in that a large excess of a nucleoside phosphoroamidite compound and a tetrazole-based compound must be used in order to increase the yield of oligonucleotide as a target substance. In addition, the solid phase synthesis method has limitations on the scale-up of equipment, etc., and also has difficulties in confirming the progress of the reaction at an intermediate stage and analyzing the structure of the intermediate.

On the other hand, in the conventional liquid phase synthesis method, it has been difficult to rapidly synthesize a large amount of oligonucleotides having a multidegree of polymerization, such as a complicated requirement for a purification operation in each step such as deprotection, coupling, and oxidation of nucleotides. For this reason, for example, in Patent Documents 1 and 2, a solution phase synthesis using a pseudo-solid phase protecting group has been proposed, but for example, it takes a long time to remove the pseudo-solid phase protecting group, and further, it is difficult to selectively remove only the pseudo-solid phase protecting group from an oligonucleotide having a pseudo-solid phase protecting group so that it is also difficult to synthesize a nucleotide (hereinafter, sometimes referred to as a "protected nucleotide" in this specification) in which a nucleic acid base or a phosphate group serving as a precursor of a building block or a fragment is protected. In Non-Patent Document 4, a pseudo-solid phase protecting group is removed by catalytic reduction using a Pd catalyst, but a toxic heavy metal or a dangerous hydrogen gas is used, and a long time of as long as 20 to 40 hours is required for deprotection. In addition, the removal of the pseudo-solid phase protecting group under general deprotection conditions of the protecting group of nucleotides has not been performed, and there has been a problem in its versatility.

PRIOR ART DOCUMENTS

Patent Document

[Patent Document 1] U.S. Pat. No. 5,548,852
[Patent Document 2] WO-A-2012/157723

Non-Patent Document

[Non-Patent Document 1] S. L. Beaucage, D. E. Bergstorm, G. D. Glick, R. A. Jones; Current Protocols in Nucleic Acid Chemistry; John Wiley & Sons (2000)
[Non-Patent Document 2] "Genome Chemistry-A Scientific Approach Utilizing Artificial Nucleic Acids," edited by Mitsuo Sekine, Isao Saito, Koudansha Scientific Co., Ltd. (2003)
[Non-Patent Document 3] C. -H. Chen, et al., Aust. J. Chem., 2010, 63, 227-235.
[Non-Patent Document 4] Y. Matsuno, et al., Org. Lett., 2016, 18, 800-803.

SUMMARY OF THF INVENTION

Problem to be Solved by the Invention

In view of such circumstances, it is an object of the present invention to provide an alkoxyphenyl derivative having high versatility which enables not only synthesis of oligonucleotides but also simple and rapid synthesis of protected oligonucleotides which have been difficult conventionally.

In addition, it is an object of the present invention to provide a protected nucleoside and a protected nucleotide (hereinafter, sometimes referred to as "Tagged" in this specification, each of which may be referred to as a "Tagged protected nucleoside" and a "Tagged protected nucleotide") which are not only synthesized of an oligonucleotide but also have high versatility in which a simple and rapid synthesis of a protected oligonucleotide which has been difficult conventionally is possible (hereinafter, sometimes referred to as "Tagged" in this specification).

Further, it is an object of the present invention to provide a method (synthesis method) for producing an oligonucleotide which is more versatile than a conventional method using the alkoxyphenyl derivatives or the Tagged protected nucleosides or Tagged protected nucleotides.

It is also an object of the present invention to provide a method for selective removal of a Tag moiety in a Tagged protected nucleoside or a Tagged protected nucleotide. In the present invention, the term "Tag moiety" refers to a moiety derived from the alkoxyphenyl derivative in the Tagged protected nucleosides or Tagged protected nucleotides.

Means for Solving the Problems

As a result of extensive studies to solve the problems, the present inventors have succeeded in creating a novel alkoxyphenyl compound and a derivative thereof described below, and have found that the object can be achieved by the compound, thereby completing the present invention.

In other words, the compound of the present invention and a derivative thereof are represented by the general formula (1) (herein after, sometimes referred to as "Compound (1)" in this specification, and other compounds represented by the general formula are also equivalent thereto).

[Chemical Formula 1]

(1)

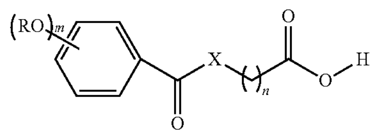

(In the formula,

R each independently represents an optionally substituted alkyl group having 10 to 40 carbons.

m represents an integer between 1 and 5. When m is 2 or more, a plurality of ROs may be the same or different.

X represents O, S, NH, or $NR^N$.

n represents an integer from 1 to 4.

$R^N$ represents an optionally substituted alkyl group having 1 to 6 carbons.)

According to the compound of the present invention or a derivative thereof, by having a structure represented by the general formula (1), not only synthesis of an oligonucleotide by a liquid phase synthesis method but also synthesis of a protected oligonucleotide which has been difficult conventionally becomes possible. More particularly, a compound of the invention or a derivative thereof (alkoxyphenyl derivative) is capable of obtaining a Tagged protected nucleoside and a Tagged protected nucleotide via a binding reaction with a nucleoside or nucleotide. Then, since the Tag moiety has the above-mentioned structure, the obtained Tagged protected nucleoside and the Tagged protected nucleotide can be conveniently separated from auxiliary materials such as an amidite monomer by a filtration operation or the like by the addition of a polar solvent, and further, only the Tag moiety can be selectively and quickly removed, and thus not only the synthesis of an oligonucleotide but also the synthesis (production) of a protected oligonucleotide which has been difficult conventionally becomes possible.

Note that, as long as the derivative of the compound does not impair the working effect of the present invention, a compound in which a chemical structure of the compound is partially substituted is widely included, and examples thereof include a compound in which an OH group moiety of a carboxyl group (—COOH) group at a terminal is replaced with a substituent. Examples of the substituent include a substituent having a high leaving ability so as to easily form a bond with a nucleoside or a nucleotide, and examples thereof include a halogen atom such as F, Cl, Br, and I, and an alkyl ester structure substituted with an alkoxy group. Further, as the substituent, a known leaving group may be used as appropriate.

In the compound of the present invention or a derivative there of, it is also preferably a compound represented by the general formula (2) or a derivative thereof.

[Chemical Formula 2]

(2)

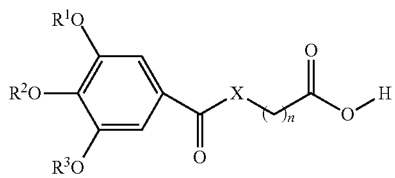

(In the formula, $R^1$, $R^2$, and $R^3$ each independently represent an optionally substituted alkyl group having 10 to 40 carbon atoms.

X represents O, S, NH, or $NR^N$.

n represents an integer from 1 to 4.

$R^N$ represents an optionally substituted alkyl group having 1 to 6 carbons.)

In addition, in the compound of the present invention or a derivative thereof, a compound represented by the general formula (3) or a derivative thereof may be used.

[Chemical Formula 3]

(3)

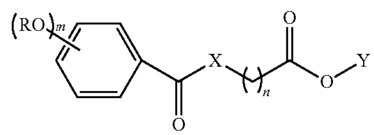

(In the formula,

R each independently represents an optionally substituted alkyl group having 10 to 40 carbons.

m represents an integer between 1 and 5. When m is 2 or more, a plurality of ROs present may be the same or different.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 4]

(4)

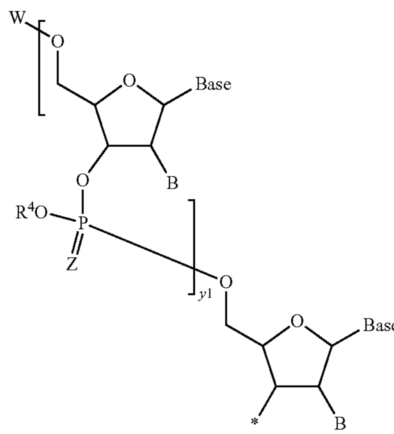

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more B are present, a plurality of Bs present may be the same or different.

W represents a hydrogen atom or protecting group.

$R_4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (3).)

[Chemical Formula 5]

(5)

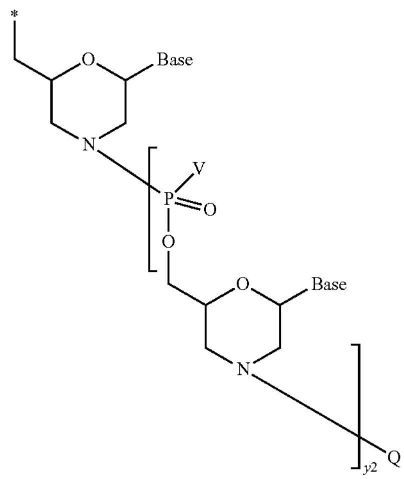

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbon atoms, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (3).)

When it has the composition, it becomes the Tagged protected nucleoside and Tagged protected nucleotide, since the Tag moiety has the above-mentioned structure, particularly in a liquid phase synthesis (including a pseudo liquid phase synthesis), by the addition of a polar solvent, it is possible to easily separate the Tag moiety from auxiliary materials such as an amidite monomer by a filtration operation or the like, and further, it is possible to selectively and quickly remove only the Tag moiety, and it is possible not only to synthesize an oligonucleotide but also to synthesize a protected oligonucleotide which has been difficult conventionally.

The nucleosides in the present invention generally represent those in which a purine or pyrimidine base and a sugar are glycosidically bonded, but broadly includes analogs thereof and those in which the general structure is partially substituted as long as the working effect of the present invention is not impaired. Examples include those in which the base moiety is not necessarily a purine or pyrimidine structure (e.g., a modified base, etc.), those in which the sugar moiety is not D-ribose or deoxy-D-ribose (e.g., morpholino nucleosides of the morpholino type, such as those shown in the general formula (5), (8)), and the like.

The nucleotide in the present invention generally also represents a phosphate ester of the nucleoside in which a purine or pyrimidine base and a sugar are glycosidically linked, but broadly includes analogs thereof and those obtained by partially replacing the general structure as long as the working effect of the present invention is not impaired. Examples include those in which the base moiety is not necessarily a purine or pyrimidine structure (e.g., a modified base), those in which the sugar moiety is not D-ribose or deoxy-D-ribose (e.g., morpholino nucleotides in the morpholino form), and phosphorothioates in which one O atom of the phosphate ester moiety is replaced by an S atom.

In addition, in the compound of the present invention or a derivative thereof, it is preferably a compound represented by the general formula (6) or a derivative thereof.

[Chemical Formula 6]

(6)

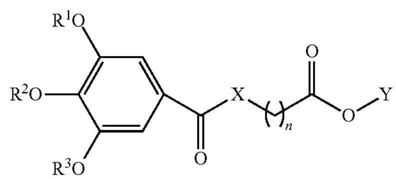

(In the formula, $R^1$, $R^2$, and $R^3$ each independently represent an optionally substituted alkyl group having 10 to 40 carbons.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 7]

(4)

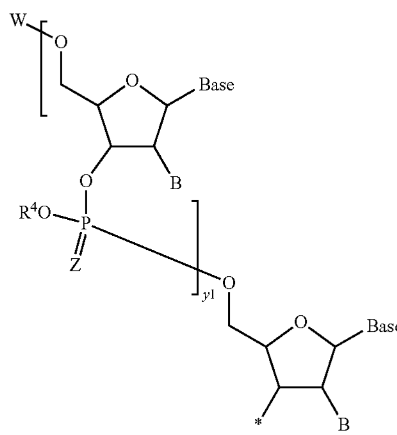

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (6).)

[Chemical Formula 8]

(5)

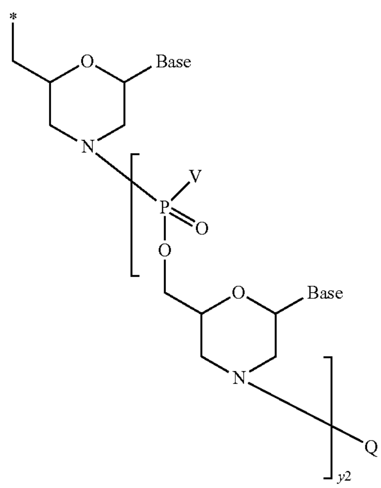

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbon atoms, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (6).)

In the compound of the present invention or a derivative thereof, W is preferably a hydrogen atom, a trityl group, a di($C_{1-6}$ alkoxy)trityl group, a mono($C_{1-18}$ alkoxy)trityl group, a 9-(9-phenyl)xanthenyl group, or a 9-(9-phenyl) thioxanthenyl group. When W is any of the above, synthesis of oligonucleotides can be more conveniently performed.

In the present compound or a derivative thereof, it is preferable that $R^4$ is an ethyl group having an electron-withdrawing group at the 2-position.

In the compound of the present invention or a derivative there of, Q is preferably a hydrogen atom, a trityl group, a di($C_{1-6}$ alkoxy)trityl group, a mono($C_{1-18}$ alkoxy)trityl group, a 9-(9-phenyl)xanthenyl group, or a 9-(9-phenyl) thioxanthenyl group. When Q is any of the above, synthesis of oligonucleotides can be more conveniently performed.

In the compound of the present invention or a derivative there of, y1 or y2 may be 1 to 100.

In the compound of the present invention or a derivative there of, y1 or y2 may also be 1 to 30.

In the compound of the present invention or a derivative there of, y1 or y2 may also be 0.

In the compound of the present invention or a derivative there of, n is preferably 1 or 2.

In the compound of the present invention or a derivative there of, m is preferably an integer of 2 to 4.

On the other hand, the production method of the present invention includes a step (1) of obtaining a compound represented by the general formula (7) or (8) for subjecting a compound represented by the general formula (3) or a derivative thereof to reduction treatment.

[Chemical Formula 9]

(3)

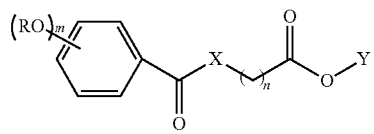

(In the formula,

R each independently represents an optionally substituted alkyl group having 10 to 40 carbons.

m represents an integer between 1 and 5. When m is 2 or more, a plurality of ROs present may be the same or different.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 10]

(4)

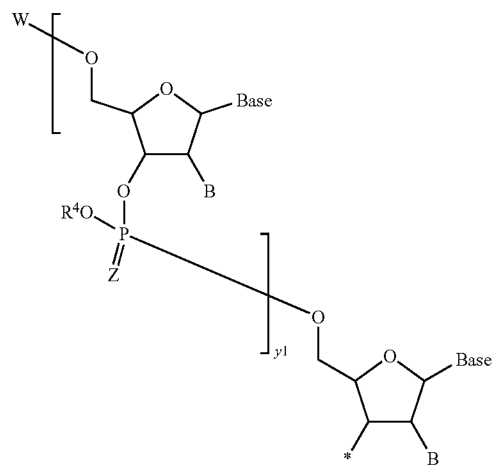

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (3).)

[Chemical Formula 11]

(5)

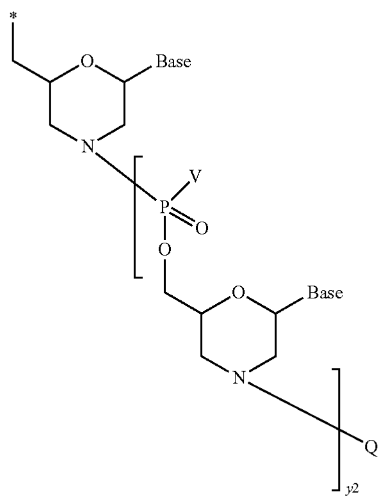

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbon atoms, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (3).)

[Chemical Formula 12]

(7)

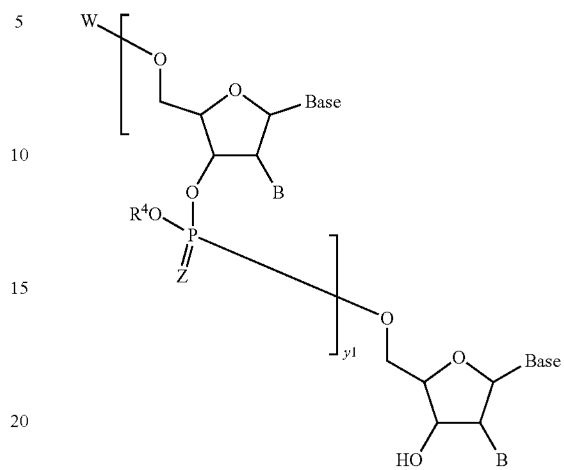

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$ are present, a plurality of $R^4$s present may be the same or different.

Z represents O or S. When 2 or more Zs are present, a plurality of Zs present may be the same or different.

y1 represents any integer greater than or equal to 0.)

[Chemical Formula 13]

(8)

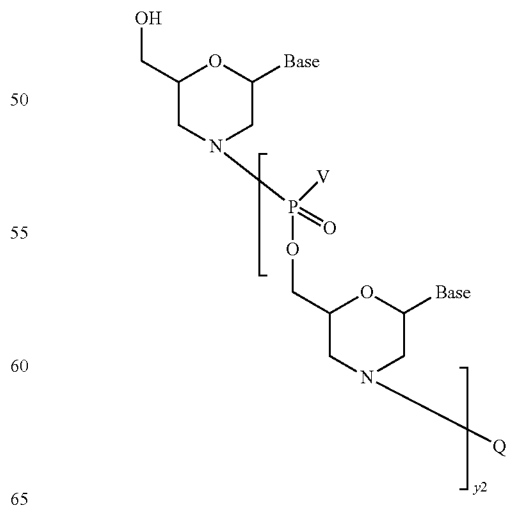

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbon atoms, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.)

According to the present production method of the present invention, since the Tagged protected nucleoside and Tagged protected nucleotide are used, in particular in liquid phase synthesis (including pseudo-liquid phase synthesis), by the addition of a polar solvent, it is possible to simply separate from auxiliary materials such as an amidite monomer by a filtration operation or the like, and further, it is possible to selectively and quickly remove only the Tag moiety, and it is possible not only to synthesize an oligonucleotide but also to synthesize a protected oligonucleotide which has been difficult conventionally. Further, for example, as compared with the proposal of Patent Document 2, in the production method of the present invention, substituent removal (elimination reaction of Tag moiety) under milder conditions (e.g., 35° C. in ammonia water) becomes possible, it is also possible to produce in a shorter time.

In addition, in the method for producing a protected oligonucleotide of the present invention, it is preferable to include a step (1) of subjecting a compound represented by the general formula (6) or a derivative thereof to reduction treatment.

[Chemical Formula 14]

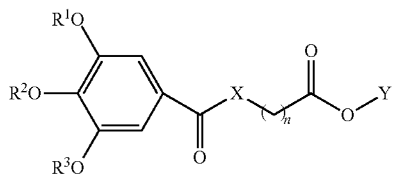

(6)

(In the formula, $R^1$, $R^2$, and $R^3$ each independently represent an optionally substituted alkyl group having 10 to 40 carbons.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 15]

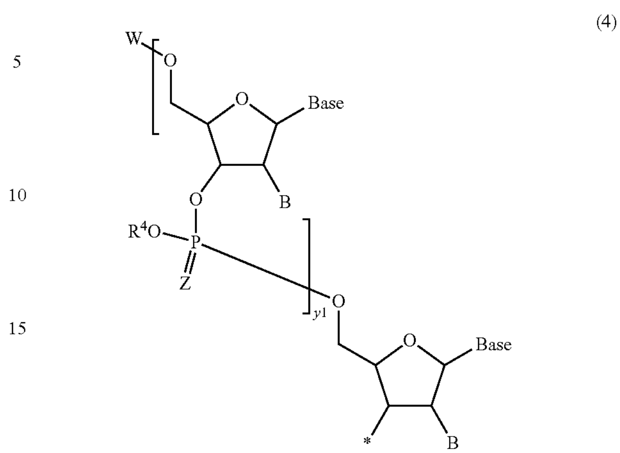

(4)

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (6).)

[Chemical Formula 16]

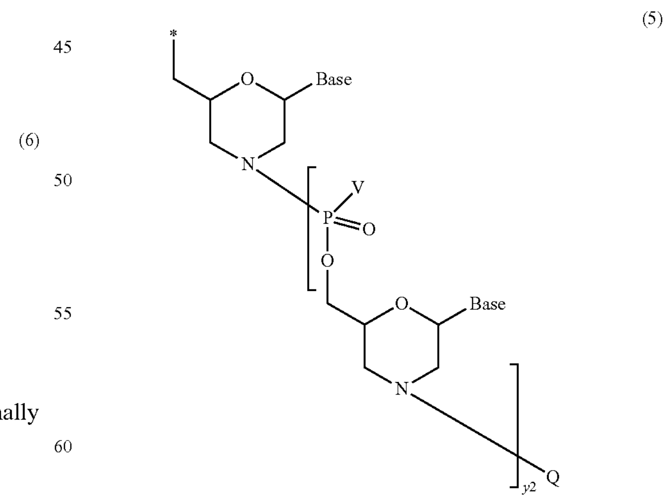

(5)

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbon atoms, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (6).)

[Chemical Formula 17]

(7)

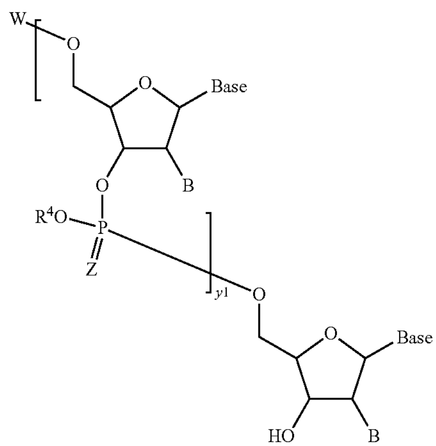

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.)

[Chemical Formula 18]

(8)

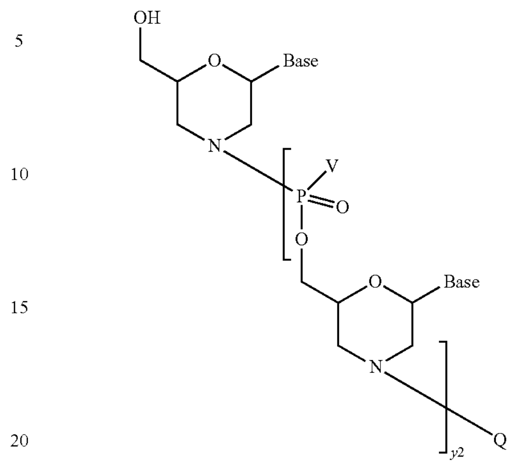

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.)

In the production method of the present invention, it is preferable that the reduction treatment described uses a boron-containing reducing agent or uses a boron-containing reducing agent and an amine. By having the configuration, a protected oligonucleotide can be more conveniently synthesized.

In addition, in the production method of the present invention, it is preferable that the boron-containing reducing agent described above is lithium borohydride, sodium borohydride, lithium triethylborohydride, or tetrabutylammonium borohydride. By having the configuration, a protected oligonucleotide can be conveniently synthesized in better yield.

In the present production method, W is preferably a hydrogen atom, a trityl group, a di ($C_{1-6}$ alkoxy)trityl group, a mono ($C_{1-18}$ alkoxy)trityl group, a 9-(9-phenyl)xanthenyl group, or a 9-(9-phenyl)thioxanthenyl group. When W is any of the above, synthesis of a protected oligonucleotide can be more conveniently performed.

In the present production method, it is preferable that $R^4$ is an ethyl group having an electron-withdrawing group at the 2-position.

In the present production method, Q is preferably a hydrogen atom, a trityl group, a di($C_{1-6}$ alkoxy)trityl group, a mono($C_{1-18}$ alkoxy)trityl group, a 9-(9-phenyl)xanthenyl group, or a 9-(9-phenyl)thioxanthenyl group. When Q is any of the above, synthesis of oligonucleotides can be more conveniently performed.

In the present production method of the present invention, y1 or y2 may be 1 to 100.

In the present production method of the present invention, y1 or y2 may also be 1 to 30.

In the present production method of the present invention, y1 or y2 may also be 0.

In the production method of the present invention, n is preferably 1 or 2.

In the production method of the present invention, m is prefer ably an integer of 2 to 4.

On the other hand, the Tag moiety removing method of the present invention (substituent removing method) includes a step (1) of subjecting a compound represented by the general formula (3) or a derivative thereof to a reduction treatment.

[Chemical Formula 19]

(3)

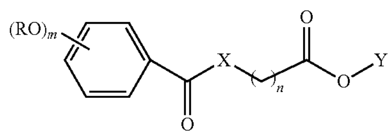

(In the formula,

R each independently represents an optionally substituted alkyl group having 10 to 40 carbons.

m represents an integer between 1 and 5. When m is 2 or more, a plurality of ROs present may be the same or different.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 20]

(4)

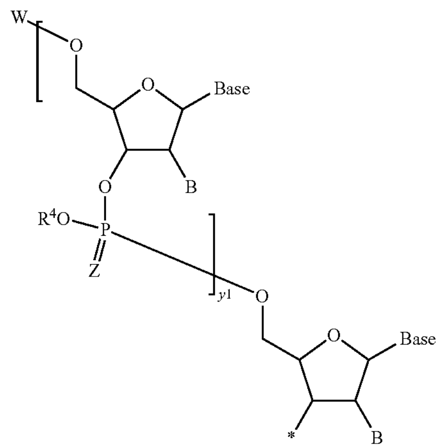

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R_4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (3).)

[Chemical Formula 21]

(5)

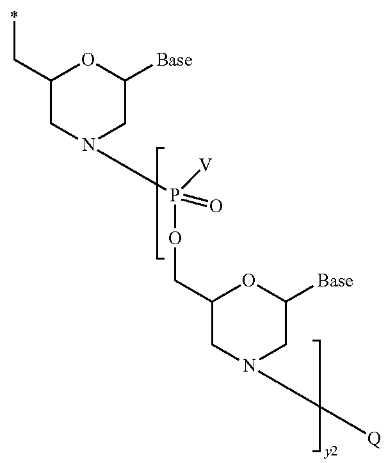

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (3).)

According to the Tag moiety removing method of the present invention, since the above-described Tagged protected nucleoside and Tagged protected nucleotide are used, it is possible to selectively and quickly remove only the Tag moiety. In addition, it is presumed that the above-mentioned working-effects are exhibited because the carbonyl group (C═O group) directly bonded to the phenyl group in the general formula (3) or the like and the X atom (0, S, NH, or $NR^N$) bonded to the carbonyl group form some kind of interaction with the reducing agent such as $LiBH_4$, and the reduction reaction is more preferably easily performed at the Tag compound site, so that the removing reaction is likely to proceed selectively and more quickly, but the scope of rights is not limited by the presumption.

In addition, in the Tag moiety removing method of the present invention, it is preferable to include a step (1) of subjecting a compo und represented by the general formula (6) or a derivative thereof to reduction treatment.

[Chemical Formula 22]

(6)

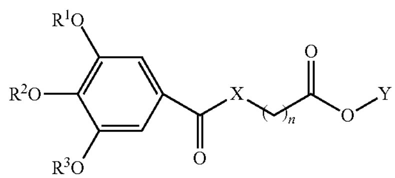

(In the formula, $R^1$, $R^2$, and $R^3$ each independently represent an optionally substituted alkyl group having 10 to 40 carbons.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 23]

(4)

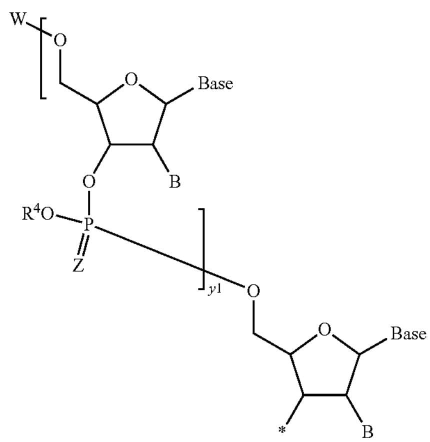

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (6).)

[Chemical Formula 24]

(5)

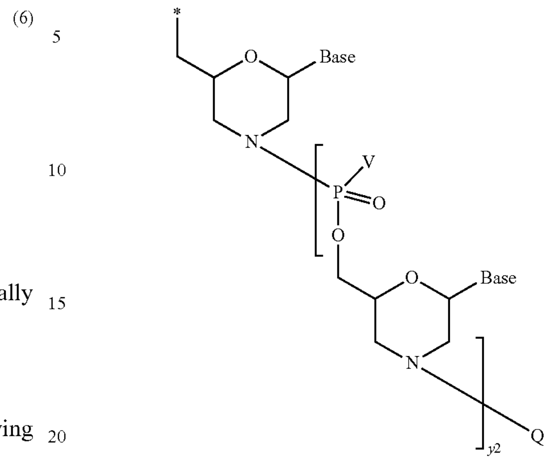

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (6).)

In the Tag moiety removing method of the present invention, it is preferable that the reduction treatment described uses a boron-containing reducing agent or uses a boron-containing reducing agent and an amine. By having the configuration, selective removal of the Tag moiety in the Tagged protected nucleoside or the Tagged protected nucleotide can be conveniently performed.

In the Tag moiety removing method of the present invention, it is also preferable that the boron-containing reducing agent described above is lithium borohydride, sodium borohydride, lithium triethylborohydride, or tetrabutylammonium borohydride. By having the configuration, selective removal of the Tag moiety in the Tagged protected nucleoside or the Tagged protected nucleotide can be performed in better yield.

Effect of the Invention

The compound of the present invention or a derivative thereof (Compound (1), (2), and the like. An alkoxyphenyl derivative.) is a novel compound, and by using the compound, it is possible to conveniently obtain the Tagged protected nucleoside and Tagged protected nucleotide.

Since the Tag moiety has the above-mentioned structure, the compounds of the present invention or derivatives thereof (Compound (3), (6), and the like. Tagged protected nucleoside and Tagged protected nucleotide, and the like) can be easily separated from auxiliary materials such as amidite monomers and the like by filtration operations by the addition of polar solvents, especially in liquid phase synthesis (including pseudo-liquid phase synthesis), and furthermore, only the Tag moiety can be selectively and quickly removed, making possible not only the synthesis of oligonucleotides by the liquid-phase synthesis method, but also the synthesis of protected oligonucleotides that have been difficult to synthesize in the past.

In addition, in the method for producing a compound of the present invention or a derivative thereof (Compound (7), (8), and the like. Oligonucleotides and the like), since the Tagged protected nucleoside and the Tagged protected nucleotide are used, synthesis of oligo nucleotides by a liquid phase synthesis method which is simpler than conventional methods becomes possible.

Further, in the method for removing the Tag moiety (substituent removal method) of the compound of the present invention or the derivative thereof (such as the compound (1), (2), (3), (6), etc.; alkoxyphenyl derivative, Tagged protected nucleoside, Tagged protected nucleotide, etc.), only the Tag moiety can be selectively and quickly removed under mild conditions because the Tagged protected nucleoside and Tagged protected nucleotide are used.

MODE FOR CARRYING OUT THF INVENTION

Hereinafter, embodiments of the present invention will be described in detail.

[Alkoxyphenyl compounds and derivatives thereof]

The alkoxyphenyl compounds of the present invention and the derivatives thereof are the compound represented by the general formula (1) or a derivative thereof.

[Chemical Formula 25]

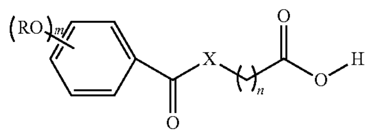

(1)

(In the formula,

R each independently represents an optionally substituted alkyl group having 10 to 40 carbons.

m represents an integer between 1 and 5. When m is 2 or more, a plurality of ROs may be the same or different.

X represents O, S, NH, or $NR^N$.

n represents an integer from 1 to 4.

$R^N$ represents an optionally substituted alkyl group having 1 to 6 carbons.)

In the general formula (1), R each independently represents an optionally substituted alkyl group having 10 to 40 carbons. The R may be an alkyl group having 13 to 30 carbons, or may be an alkyl group having 15 to 20 carbons, and among them, an alkyl group having 18 carbons may be preferred. In addition, when a plurality of Rs are present, they each independently may be a linear alkyl group or a branched alkyl group, but are preferably linear alkyl groups. Further, when the R is an alkyl group having 10 to 40 carbons, synthesis of the Tagged protected nucleoside and the Tagged protected nucleotide of the present invention becomes easy, and also an effect of improving solubility and separation ability can be obtained.

In the general formula (1), m represents an integer of 1 to 5. When m is 2 or more, a plurality of ROs may be the same or different. Preferably m is an integer from 2 to 4, more preferably m is 3. In addition, when the carbonyl group (C═O group) directly bonded to the phenyl group is set to the 1-position, the RO group is preferably bonded to the 3-position, the 4-position, or the 5-position, and when m=3, it is preferably bonded to the 3-position, the 4-position, or the 5-position. Further, by adjusting the value of m within the range, it is possible to adjust the solubility of the Tagged protected nucleoside and the Tagged protected nucleotide of the present invention in a nonpolar solvent.

In the general formula (1), X represents O, S, NH, or $NR^N$. Among them, X is preferably O.

In the general formula (1), n represents an integer of 1 to 4. Among them, n is preferably 1 or 2.

In the general formula (1), $R^N$ represents an optionally substituted alkyl group having 1 to 6 carbons. Examples of the $R^N$ include methyl group, ethyl group, 1-propyl group, 1-methyl-1-ethyl group, 1-butyl group, 1-methyl-1-propyl group, 1,1-dimethyl-1-ethyl group, 2-methyl-1-propyl group, 1-pentyl group, and 2-pentyl group.

In addition, in the present invention, it is preferable that the alkoxyphenyl compound and a derivative thereof are a compound represented by the general formula (2) or a derivative thereof.

[Chemical Formula 26]

(2)

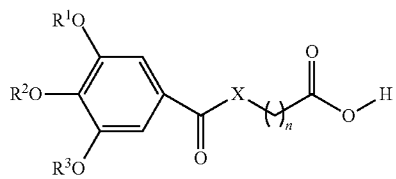

(In the formula, $R^1$, $R^2$, and $R^3$ each independently represent an optionally substituted alkyl group having 10 to 40 carbons.

X represents O, S, NH, or $NR^N$.

n represents an integer from 1 to 4.

$R^N$ represents an optionally substituted alkyl group having 1 to 6 carbons.)

In Formula (2), $R^1$, $R^2$, and $R^3$ each independently represent an optionally substituted alkyl group having 10 to 40 carbons. The $R^1$, $R^2$ and $R^3$ may be alkyl groups having 13 to 30 carbon, alkyl groups having 15 to 20 carbons, and among them, alkyl groups having 18 carbons are preferable. The $R^1$, $R^2$, and $R^3$ are independent of each other, and may be straight-chain or branched-class groups, but all are preferably straight-chain groups.

In the general formula (2), X, n, and $R^N$ are the same as those of the general formula (1).

In addition, although the alkoxyphenyl compound of the present invention and a derivative thereof have been exemplified by the syn thesis method as an example, they may be synthesized using a know n method using a commercially available raw material.

[Tagged protected nucleosides and Tagged protected nucleotides, etc.]

The Tagged protected nucleosides and the Tagged protected nucleotides in the present invention are a compound represented by the general formula (3) or a derivative thereof.

[Chemical Formula 27]

(3)

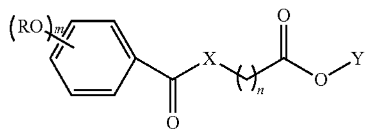

(In the formula,

R each independently represents an optionally substituted alkyl group having 10 to 40 carbons.

m represents an integer between 1 and 5. When m is 2 or more, a plurality of ROs present may be the same or different.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 28]

(4)

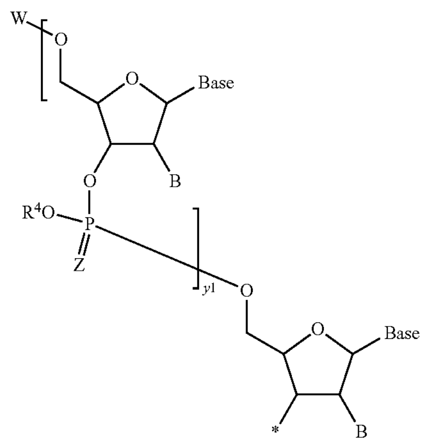

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (3).)

[Chemical Formula 29]

(5)

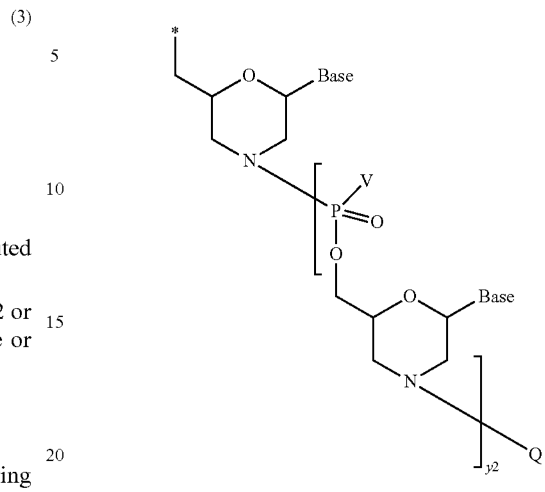

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (3).)

In the general formula (3), R, m, X, n, and $R^N$ are the same as those of the general formula (1).

In the general formula (3), Y represents the following general formula (4) or the general formula (5).

In the general formula (4), Base represents a nucleobase which may be modified. When 2 or more Bases are present, a plurality of Bases present may be the same or different.

Examples of the Base include adenyl groups, guanyl groups, sitosyl groups, thyminyl groups, or uracil groups, and derivatives thereof, as well as modifications thereof. As the above-mentioned modifications, for example, a polar group or the like may be protected by a known protecting group or the like. In addition, a plurality of Bases present in the oligonucleotide may be the same or different.

In the general formula (4), B represents a hydrogen atom, an optionally protected hydroxyl group, or a halogen. When 2 or more B s are present, a plurality of Bs present may be the same or different. In addition, in the case of a protected hydroxyl group, a known method can be appropriately used as a protecting group and a protective method.

In the general formula (4), W represents a hydrogen atom or protecting group. When W is a protecting group, a known method can be appropriately used as a protecting group and a protecting method.

It is also preferred that W is a hydrogen atom, a trityl group, a di($C_{1-6}$ alkoxy)trityl group, a mono($C_{1-18}$ alkoxy) trityl group, a 9-(9-phenyl) xanthenyl group, or a 9-(9-phenyl)thioxanthenyl group. When W is any of the above, the synthesis of oligonucleotides can be more conveniently performed.

In the general formula (4), $R^4$ represents an alkyl group having 1 to 4 carbons and having an electron-withdrawing group. If 2 or more $R^4$s are present, a plurality of $R^4$s present may be the same or different. It is also preferred that $R^4$ is an ethylenic group having an electron-withdrawing group at the 2-position. Further, as the electron-withdrawing group, for example, a cyano group can be mentioned as a preferable example.

In the general formula (4), Z represents O or S. When 2 or more Zs are present, a plurality of Zs present may be the same or different.

In the general formula (4), y1 represents an arbitrary integer of 0 or more. y1 may be 1 to 100, 1 to 50, 1 to 30, 1 to 20, 1 to 10, or 0.

In the general formula (4), * represents a bonding position in the general formula (3).

In the general formula (5), Base is the same as in the general formula (4).

In the general formula (5), Q represents a hydrogen atom or protecting group. When Q is a protecting group, a known method can be appropriately used as a protecting group and a protecting method.

It is also preferred that Q is a hydrogen atom, a trityl group, a di($C_{1-6}$ alkoxy)trityl group, a mono($C_{1-18}$ alkoxy) trityl group, a 9-(9-phenyl) xanthenyl group, or a 9-(9-phenyl)thioxanthenyl group. When Q is any of the above, synthesis of oligonucleotides can be more conveniently performed.

In the general formula (5), V represents an alkoxy group having 1 to 6 carbons, a di($C_{1-6}$ alkyl)amino group, or a piperazino group in which a nitrogen atom at the 4-position is protected with a protecting group and may be further substituted. When 2 or more Vs are present, a plurality of Vs present may be the same or different.

In the general formula (5), y2 represents an arbitrary integer of 0 or more. y2 may be 1 to 100, 1 to 50, 1 to 30, 1 to 20, 1 to 10, or 0.

In the general formula (5), * represents a bonding position in the general formula (3).

Further, it is preferable that the Tagged protected nucleoside and the Tagged protected nucleotide of the present invention be the compound represented by the general formula (6) or a derivative thereof.

[Chemical Formula 30]

(6)

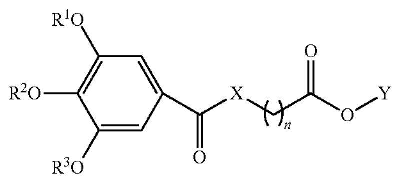

(In the formula, $R^1$, $R^2$, and $R^3$ each independently represent an optionally substituted, 10 to 40 carbons.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 31]

(4)

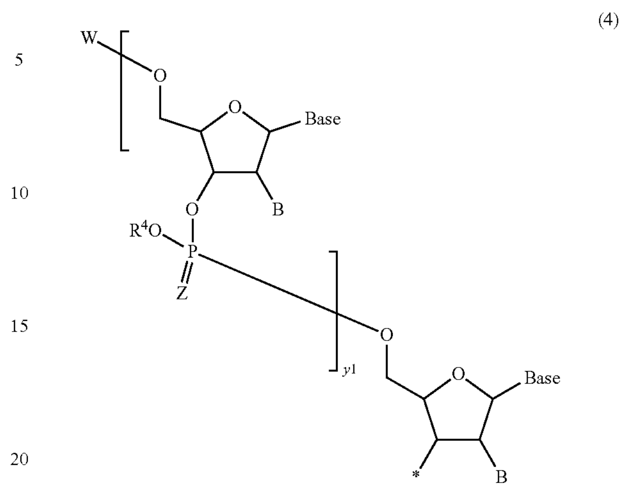

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (6).)

[Chemical Formula 32]

(5)

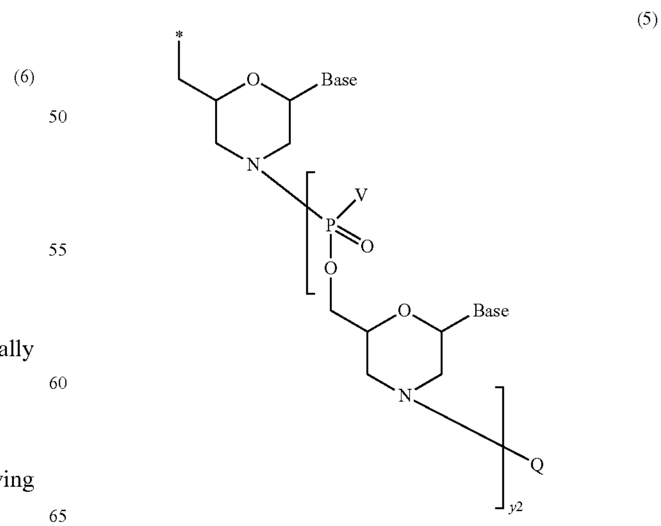

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (6).)

In the general formula (6), $R^1$, $R^2$, $R^3$, X, n, and $R^N$ are the same as in the general formula (2).

In the general formula (6), Y is the same as in the general formula (3).

In addition, although the Tagged protected nucleoside and the Tagged protected nucleotide of the present invention have been exemplified by the synthesis method in the examples, they may be synthesized using a known method using a commercially available raw material.

As a method (synthesis method) for producing a Tagged protected nucleoside and a Tagged protected nucleotide of the present invention, for example, it can be obtained by a method of binding a nucleoside or a nucleotide with an alkoxyphenyl compound or a derivative thereof described above. As a binding method, for example, a method of subjecting the alkoxyphenyl compound or a derivative thereof to a condensation reaction with a nucleoside or a nucleotide can be mentioned. When using the condensation reaction above, for example, the method of combining the alkoxyphenyl compound represented by a general formula (1) or (2) and a nucleoside or a nucleotide using a condensation agent, or the method of binding the derivative (for example, ester derivative, acid chloride derivative, etc.) of the alkoxyphenyl compound represented by the general formula (1) or (2) whose reactivity has been enhanced by a substituent or the like to a nucleoside or a nucleotide, or the method of binding the alkoxyphenyl compound represented by the general formula (1) or (2) with a nucleoside or a nucleotide whose reactivity has been enhanced by a substituent or the like, can be appropriately used.

[Method for Producing Protected Oligonucleotide and Method f or Removing Tag Moiety, etc.]

The method for producing a protected oligonucleotide of the present invention (synthesis method) and method for removing the Tag moiety of the present invention (substituent removing method) include a step (1) of subjecting a compound represented by the general formula (3) or a derivative thereof to reduction treatment.

[Chemical Formula 33]

(3)

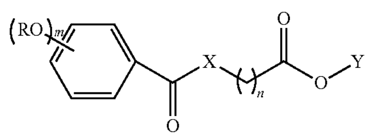

(In the formula,

R each independently represents an optionally substituted alkyl group having 10 to 40 carbons.

m represents an integer between 1 and 5. When m is 2 or more, a plurality of ROs present may be the same or different.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 34]

(4)

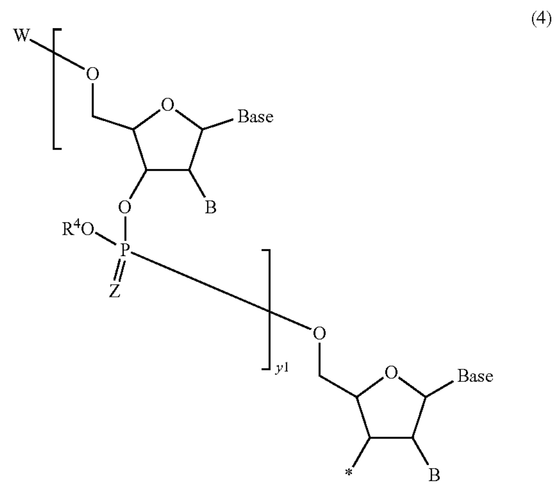

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs p resent may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (3).)

[Chemical Formula 35]

(5)

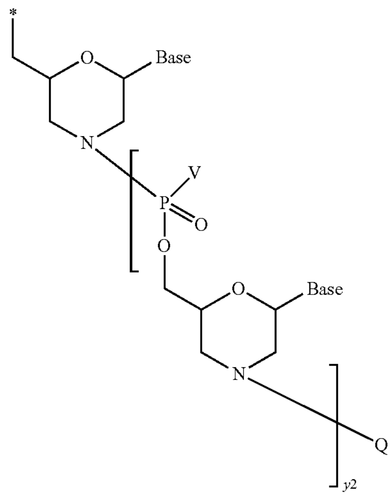

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbon atoms, a di($C_{1-6}$ alkyl)amino group, or a piperazino group in which the nitrogen atom at the 4-position is protected with a protecting group and may be further substituted. When V are present in an amount of 2 or more, a plurality of V present may be the same or different.

y2 represents any integer greater than or equal to 0.

* represents a bonding position in the general formula (3).)

[Chemical Formula 36]

(7)

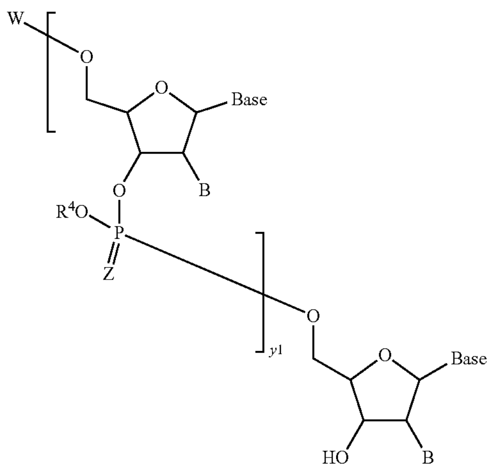

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.)

[Chemical Formula 37]

(8)

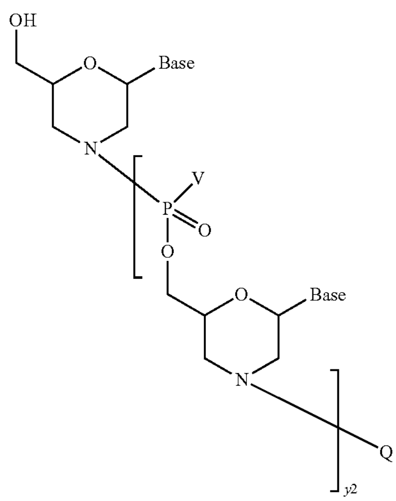

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of V presents may be the same or different.

y2 represents any integer greater than or equal to 0.)

In the method for producing a protected oligonucleotide described above, the general formulas (3), (4), and (5) are the same as de scribed above.

In the general formula (7) in the method for producing a protected oligonucleotide above, Base, B, W, $R^4$, Z, and y1 are the same as those of the general formula (4).

In the general formula (8) in the method for producing a protected oligonucleotide, Base, Q, V, and y2 are the same as those of the general formula (5).

In the method for producing a protected oligonucleotide of the present invention and method for removing the Tag moiety of the pre sent invention, it is preferable to include a step (1) of subjecting a compound represented by the general formula (6) or a derivative thereof to reduction treatment.

[Chemical Formula 38]

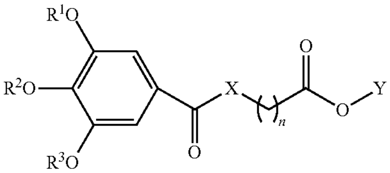

(6)

(In the formula, $R^1$, $R^2$, and $R^3$ each independently represent an optionally substituted alkyl group having 10 to 40 carbons.

X represents O, S, NH, or $NR^N$.

n represents an integer from 1 to 4.

$R^N$ represents an optionally substituted alkyl group having 1 to 6 carbons.

Y represents the following general formula (4) or general formula (5).)

[Chemical Formula 39]

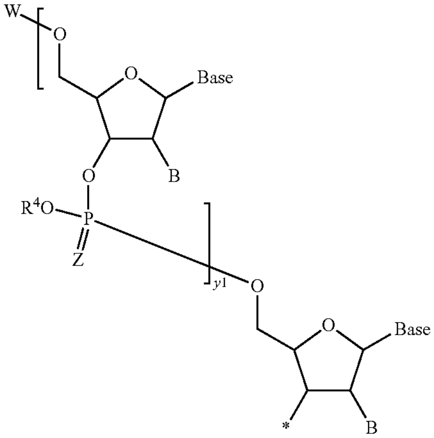

(4)

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.

* represents a bonding position in the general formula (6).)

[Chemical Formula 40]

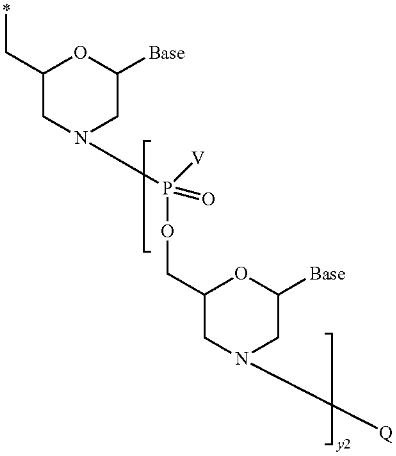

(5)

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of Vs present may be the same or different.

y2 represents any integer greater than or equal to 0.

* represents a bonding position in the general formula (6).)

[Chemical Formula 41]

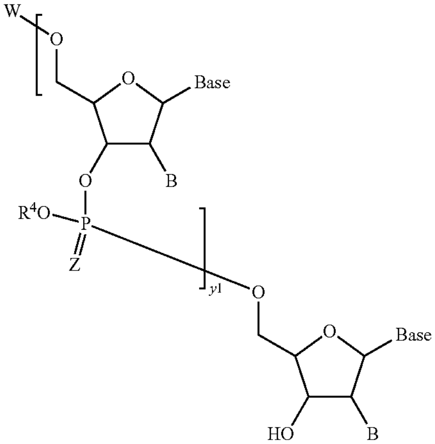

(7)

(In the formula,

Base represents a nucleobase which may be modified. When 2 or more Bases are present, a plurality of Bases present may be the same or different.

B represents a hydrogen atom, an optionally protected hydroxyl group, or a halogen. When 2 or more Bs are present, a plurality of Bs present may be the same or different.

W represents a hydrogen atom or protecting group.

$R^4$ represents an alkyl group having 1 to 4 carbons and having an electron-withdrawing group. If 2 or more $R^4$s are present, a plurality of $R^4$s present may be the same or different.

Z represents O or S. When 2 or more Zs are present, a plurality of Zs present may be the same or different.

y1 represents any integer greater than or equal to 0.)

[Chemical Formula 42]

(8)

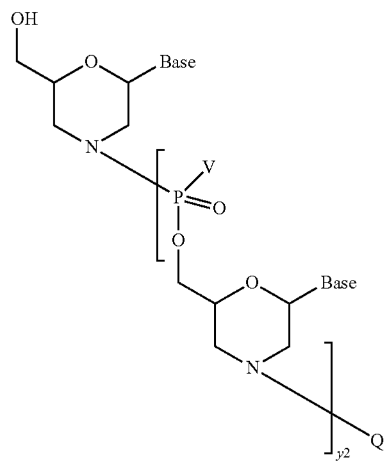

(In the formula,

Base represents a nucleobase which may be modified. When 2 or more Bases are present, a plurality of Bases present may be the same or different.

Q represents a hydrogen atom or protecting group.

V represents an alkoxy group having 1 to 6 carbons, a di($C_{1-6}$ alkyl)amino group, or a piperazino group in which the nitrogen atom at the 4-position is protected with a protecting group and may be further substituted. When 2 or more Vs are present, a plurality of V presents may be the same or different.

y2 represents any integer greater than or equal to 0.)

In the method for producing the protected oligonucleotide and method for removing the Tag moiety of the present invention, the general formulas (3), (4), and (5) are the same as described above.

In the method for producing the protected oligonucleotide and the inventive method for removing the Tag moiety, in the general formula (7), Base, B, W, $R^4$, Z, and y1 are the same as those of the general formula (4).

In the method for producing the protected oligonucleotide and method for removing the Tag moiety of the present invention, in the general formula (8), Base, Q, V, and y2 are the same as those of the general formula (5).

In the method for producing the protected oligonucleotide and method for removing the Tag moiety of the present invention, it is preferable that the reduction treatment is one using a boron-containing reducing agent or using a boron-containing reducing agent and an a mine. By having the configuration, a protected oligonucleotide can be more conveniently synthesized.

As the boron-containing reducing agent, a known one can be used, but among them, lithium borohydride, sodium borohydride, lithium triethylborohydride, tetrabutylammonium borohydride, and the like are preferred. These compounds may be used alone, or 2 or more of them may be used in combination. By having the configuration, a protected oligonucleotide can be conveniently synthesized in better yield.

When the boron-containing reducing agent and an amine are used, a known one can be used as the amine, but among them, diisopropylethylamine, triethylamine, pyridine, and the like are preferred. These compounds may be used alone, or 2 or more of them may be used in combination. By having the configuration, a protected oligonucleotide can be conveniently synthesized in better yield.

In the step (1), a known method may be used using a commercially available raw material, unless the chemical structure of the compound or a derivative thereof where the synthesis method or the re action method is represented by the general formula (6) or the like are damaged.

The step (1) may be, for example, a step of dissolving or mixing a compound represented by the general formula (6) or the like or a derivative thereof with a boron-containing reducing agent or a boron-containing reducing agent and an amine in an organic solvent, and stirring and reacting the mixture at −10° C. or at room temperature.

In addition, a method for producing a protected oligonucleotide of the present invention and a method for removing a Tag moiety of the present invention illustrate a synthesis method and a reaction method thereof in Examples, but other known methods may be used using a commercially available raw material.

As a method for producing a Tagged protected oligonucleotide of the present invention, for example, a 2 mer is taken as an example, and a Tagged protected nucleoside or a Tagged protected nucleotide described is subjected to a coupling reaction with an amidated nucleoside or nucleotide (Step A), and the obtained 2 mer is subjected to phosphoric esterification in an oxidation step (Step B), and deprotection of the protecting group W is performed (Step C), and filtration (Step D) is performed, whereby a 2 mer of a Tagged protected nucleotide can be obtained. Further, examples of the higher order (n+1) mer include a method in which the method is similarly obtained n times, and a method in which a nucleotide derivative having a certain length is used to bind them to each other.

EXAMPLES

Hereinafter, examples and the like specifically showing the configuration and effects of the present invention will be described. Hereinafter, the concentration operation in the examples was carried out under reduced pressure unless otherwise specified. The evaluation items in Examples and the like were measured as follows.

<Measurement of $^1$H-NMR Spectrum>

$^1$H-NMR spectrum was measured using a nuclear magnetic resonance apparatus (manufactured by Nippon Electronics Co., Ltd., product name AL400, and product name ECS-600) and tetramethylsilane as an internal standard.

<Determination of $^{13}$C-NMR Spectrum>

$^{13}$C-NMR spectrum was measured using nuclear magnetic resonators (manufactured by Japan Electronics Co., Ltd., under the product name AL400, and by Japan Electronics Co., Ltd., under the product name ECS-600) and using tetramethylsilane as an internal standard.

<Measure TOF/MS Spectrum>

TOF/MS spectra were measured using time-of-flight mass spectrometry (Waters, product name LCT-PremierXE and Japanese Electronic, product name JMS T-100LP).

1. Synthesis of 2-((3,4,5-Tris(Octadecyloxy)Benzoyl)Oxy)Acetic Acid

(A) Process Via Tert-Butyl Ester

Example 1-1

(1) Synthesis of 2-(Tert-Butoxy)-2-Oxoethyl 3,4,5-Tris(Octadecyloxy)Benzoate

[Chemical Formula 43]

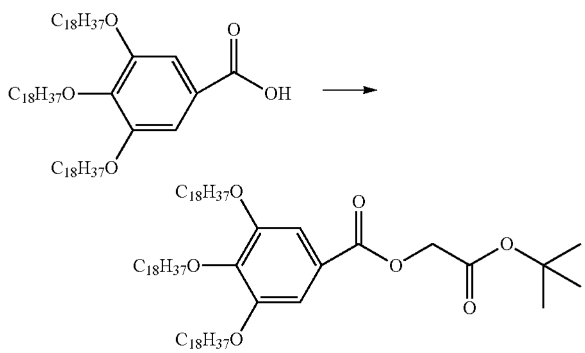

Triethylamine (0.39 g, 3.87 mmol) and 2-butyl tert-bromoacetate (0.76 g, 3.87 mmol) was added to a suspension of 3,4,5-tris(octadecyloxy)benzoic acid (1.80 g, 1.94 mmol) in THF (10 mL), and then stirred at 60° C. for 2 hours. After cooling the reaction solution to room temperature, the solid precipitated by dropping methanol (54 mL) was filtered. The solid was washed with methanol, and then dried in vacuo at 50° C. to give the title compound (1.95 g, 97%) as a white solid.

$^1$H-NMR (400 MHz, $CDCl_3$): δ 0.88 (t, 9H, J=6.8 Hz), 1.16-1.41 (m, 84H), 1.41-1.57 (m, 6H), 1.49 (s, 9H), 1.66-1.88 (m, 6H), 3.95-4.11 (m, 6H), 4.70 (s, 2H), 7.31 (s, 2H).

$^{13}$C-NMR (100 MHz, $CDCl_3$): δ 14.02, 22.48, 22.66, 22.83, 26.08, 26.11, 27.88, 28.08, 29.35, 29.40, 29.56, 29.64, 29.65, 29.70, 29.97, 30.22, 30.36, 31.76, 31.93, 32.10, 61.66, 69.35, 73.51, 82.32, 108.69, 108.90, 123.82, 123.93, 143.11, 143.38, 152.93, 165.83, 166.90.

TOF/MS (ESI): calcd for $C_{67}H_{124}O_7Na$ $[M+Na]^+$ 1063.9245, found 1063.9254.

Example 1-2

(2) Synthesis of 2-((3,4,5-Tris(Octadecyloxy)Benzoyl)Oxy)Acetic Acid

[Chemical Formula 44]

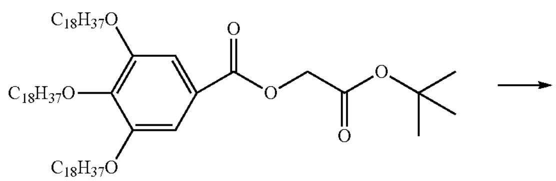

-continued

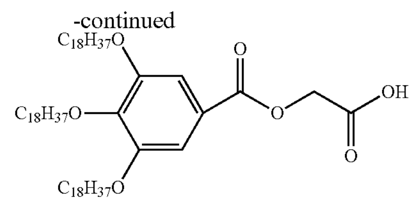

Trifluoroacetic acid (11.40 g, 100.0 mmol) was added to a solution of 2-(tert-butoxy)-2-oxoethyl 3,4,5-tris(octadecyloxy)benzoate (5.21 g, 5.0 mmol) in chloroform (20 ml), and then stirred at 50° C. for 17 hours. After cooling the reaction solution to room temperature, the solid precipitated by dropping acetonitrile (50 mL) was filtered. The solid was washed with acetonitrile-chloroform mixture solvent, and then dried in vacuo at 50° C. to give the title compound (4.89 g, 99%) as a white solid.

$^1$H-NMR (400 MHz, $CDCl_3$): δ 0.88 (t, 9H, J=7.0 Hz), 1.16-1.54 (m, 90H), 1.69-1.88 (m, 6H), 3.95-4.11 (m, 6H), 4.87 (s, 2H), 7.30 (s, 2H).

$^{13}$C-NMR (100 MHz, $CDCl_3$): δ 14.08, 22.68, 26.06, 26.10, 29.36, 29.41, 29.57, 29.65, 29.66, 29.72, 30.35, 31.93, 60.49, 69.30, 73.57, 108.53, 123.31, 143.17, 152.96, 165.74.

TOF/MS (ESI): calcd for $C_{63}H_{116}O_7Na$ $[M+Na]^+$ 1007.8619, found 1007.8639.

(B) Process Via Benzyl Esters

Example 1-3

(1) Synthesis of 2-Benzyloxy-2-Oxoethyl 3,4,5-Tris(Octadecyloxy)Benzoate

[Chemical Formula 45]

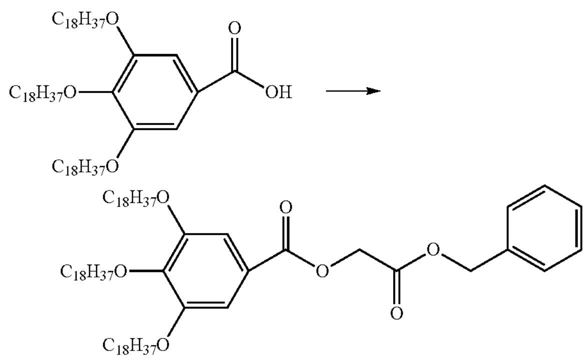

Triethylamine (0.20 g, 1.94 mmol) and benzyl 2-bromoacetate (0.45 g, 1.94 mmol) was added to a suspension of 3,4,5-tris(octadecyloxy)benzoic acid (0.90 g, 0.97 mmol) in chloroform (5 mL), and then stirred at 50° C. for 14 hours. After cooling the reaction solution to room temperature, the solid precipitated by dropping methanol (18 mL) was filtered. The solid was washed with methanol, and then dried in vacuo at 50° C. to give the title compound (1.02 g, 97%) as a white solid.

$^1$H-NMR (400 MHz, $CDCl_3$): δ 0.88 (t, 9H, J=6.8 Hz), 1.16-1.41 (m, 84H), 1.41-1.54 (m, 6H), 1.66-1.91 (m, 6H), 3.95-4.08 (m, 6H), 4.86 (s, 2H), 5.23 (s, 2H), 7.24-7.41 (m, 7H).

$^{13}$C-NMR (100 MHz, $CDCl_3$): δ 14.08, 22.71, 26.13, 26.16, 29.40, 29.43, 29.46, 29.62, 29.69, 29.71, 29.76, 30.00, 30.43, 31.98, 61.24, 67.07, 69.40, 73.59, 108.76, 123.69, 128.32, 128.50, 128.65, 135.35, 143.28, 152.96, 153.01, 165.84, 167.77.

Example 1-4

(2) Synthesis of 2-((3,4,5-Tris(Octadecyloxy)Benzoyl)Oxy)Acetic Acid

[Chemical Formula 46]

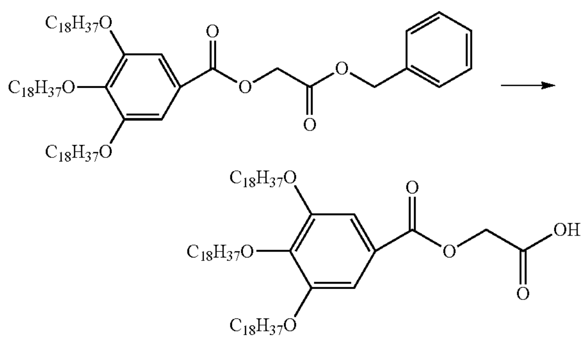

10% Pd-C (0.09 g) was added to a solution of 2-benzyloxy-2-oxoethyl 3,4,5-tris(octadecyloxy)benzoate (0.91 g, 0.85 mmol) in THF (4.3 mL), and then stirred under a hydrogen balloon at 40° C. for 19 hours. The reaction solution was cooled to room temperature, and then 10% Pd-C was removed by Celite filtration. After concentrating the filtrate, the solid precipitated by dropping acetonitrile (18 mL) to the residue was filtered. The solid was washed with acetonitrile, and then dried in vacuo at 50° C. to give the title compound (0.84 g, 100%) as a white solid.

2. Synthesis of thymidinyl-[3'→5']-deoxycytidinyl-[3'→5']-deoxycytidinyl-[3'→5']-deoxycytidinyl-[3'→5']-deoxyguanidyl-[3'→5']-deoxycytidinyl-[3'→5']-deoxycytidinyl-[3'→5']thymidinyl-[3'→5']-deoxyguanidyl-[3'→5']-thymidinyl-[3'→5']-deoxyguanidyl-[3'→5']-deoxyadenylyl-[3'→5']-deoxycytidinyl-[3'→5']-deoxyadenylyl-[3'→5']-thymidinyl-[3'→5']-deoxyguanidyl-[3'→5']-deoxycytidinyl-[3'→5']-deoxyadenylyl-[3'→5']-thymidinyl-[3'→5']thymidine (20 mer oligonucleic acid)

Example 2-1

(1) Synthesis of 5'-O-(4,4'-Dimethoxytrityl)Thymidine-3'-Yl 2-((3, 4,5-Tris(Octadecyloxy)Benzoyl) Oxy)Acetate

[Chemical Formula 47]

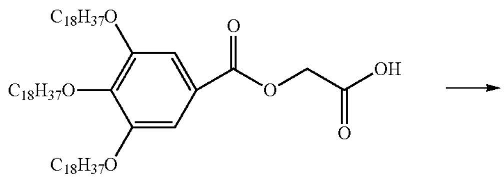

-continued

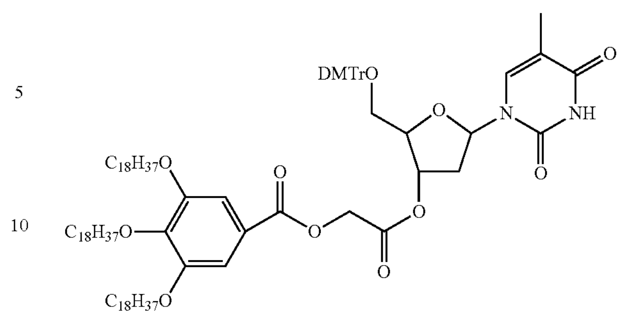

COMU (4.73 g, 11.05 mmol) was added to a suspension of 2-((3,4,5-tris(octadecyloxy)benzoyl)oxy)acetic acid (4.95 g, 5.02 mmol), 5'-O-(4,4'-dimethoxytrityl)thymidine (3.28 g, 6.03 mmol), and 1-methylimidazole (2.27 g, 27.62 mmol) in THF (50 mL), and then stirred at room temperature for 3.5 hours. The solid precipitated by dropping acetonitrile (248 mL) to the reaction solution was filtered. The solid was washed with acetonitrile—THF mixture solvent, and then dried in vacuo at 50° C. to give the title compound (7.16 g, 95%).

$^{1}$H-NMR (400 MHz, $CDCl_3$): δ 0.88 (t, 9H, J=6.8 Hz), 1.16-1.54 (m, 93H), 1.69-1.88 (m, 6H), 2.42-2.58 (m, 2H), 3.42-3.55 (m, 2H), 3.78 (s, 6H), 3.95-4.05 (m, 6H), 4.18 (s, 1H), 4.82 (s, 2H), 5.56 (d, 1H, J=5.6 Hz), 6.40-6.50 (m, 1H), 6.80-6.90 (m, 4H), 7.20-7.40 (m, 9H), 7.61 (s, 1H), 8.03 (s, 1H).

$^{13}$C-NMR (100 MHz, $CDCl_3$): δ 11.62, 14.10, 22.71, 26.11, 26.15, 29.38, 29.45, 29.61, 29.68, 29.75, 30.40, 31.96, 37.88, 55.28, 61.12, 63.68, 69.35, 73.60, 83.93, 84.40, 87.36, 108.59, 111.66, 113.43, 123.26, 127.29, 128.08, 128.19, 130.10, 130.15, 135.20, 135.25, 135.32, 144.22, 150.11, 153.02, 158.92, 163.16, 165.85, 167.50.

TOF/MS (ESI): calcd for $C_{94}H_{146}N_2O_{13}Na$ $[M+Na]^+$ 1534.0723, found 1534.0759.

Example 2-2

(2) Synthesis of Thymidine-3'-Yl 2-((3,4,5-Tris(Octadecyloxy)Benzoyl)Oxy)Acetate

[Chemical Formula 47]

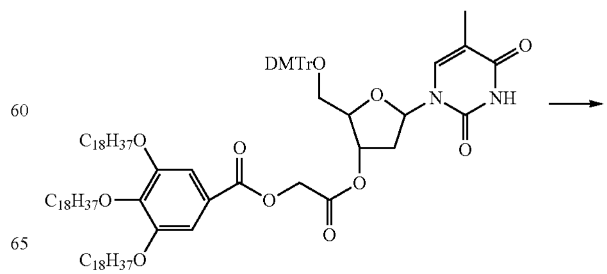

-continued

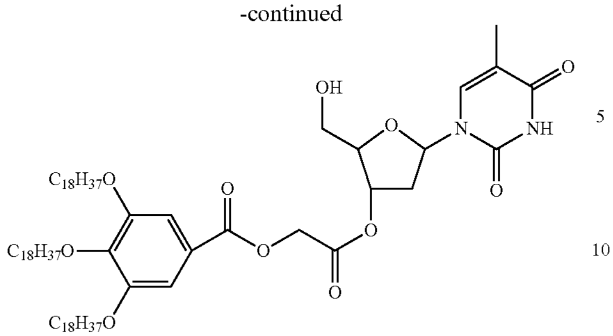

Pyrrole (1.54 g, 22.98 mmol) and trifluoroacetic acid (0.66 g, 5.75 mmol) were added to a solution of 5'-O-(4,4'-dimethoxytrityl)thymidine-3'-yl 2-((3,4,5-tris(octadecyloxy)benzoyl)oxy)acetate (6.95 g, 4.60 mmol) in dichloromethane (174 mL), and then stirred at room temperature for 2.5 hours. the solid precipitated by dropping acetonitrile (52 mL) and acetonitrile (156 mL) to the reaction solution was filtered. The solid was washed with acetonitrile-acetone-dichloromethane mixture solvent and acetonitrile, and then dried in vacuo at 50° C. to give the title compound (5.04 g, 91%).

$^1$H-NMR (400 MHz, $CDCl_3$): δ 0.88 (t, 9H, J=6.8 Hz), 1.11-1.39 (m, 84H), 1.43-1.51 (m, 6H), 1.66 (s, 1H), 1.71-1.85 (m, 6H), 1.95 (s, 3H), 2.36-2.58 (m, 3H), 3.89-3.97 (m, 2H), 3.97-4.08 (m, 6H), 4.15 (dd, 1H, J=2.0, 2.4 Hz), 4.84 (s, 2H), 5.45-5.53 (m, 1H), 6.20 (dd, 1H, J=6.0, 8.8 Hz), 7.29 (s, 2H), 7.45 (d, 1H, J=1.2 Hz), 8.59 (s, 1H).

$^{13}$C-NMR (100 MHz, $CDCl_3$): δ 12.58, 14.12, 22.70, 26.07, 26.11, 29.33, 29.38, 29.43, 29.59, 29.67, 29.68, 29.73, 30.35, 31.94, 36.99, 61.12, 62.57, 69.24, 73.58, 75.97, 84.91, 86.46, 108.36, 111.48, 123.17, 136.41, 143.09, 150.29, 152.96, 163.40, 165.91, 167.71.

TOF/MS (ESI): calcd for $C_{73}H_{128}N_2O_{11}Na$ $[M+Na]^+$ 1231.9416, found 1231.9432.

Example 2-3

(3) Synthesis of 5'-O-((Cyanoethoxy)(Thymidine-3'-Yl)Phosphoryl) Thymidine-3'-Yl 2-((3,4,5-Tris(Octadecyloxy)Benzoyl)Oxy)Acetate

[Chemical Formula 49]

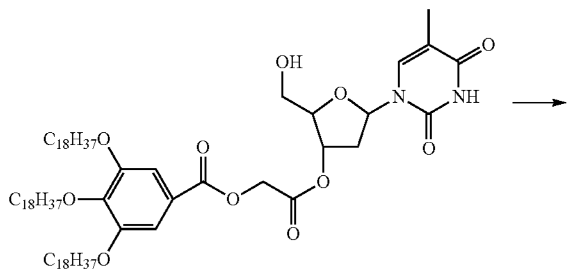

-continued

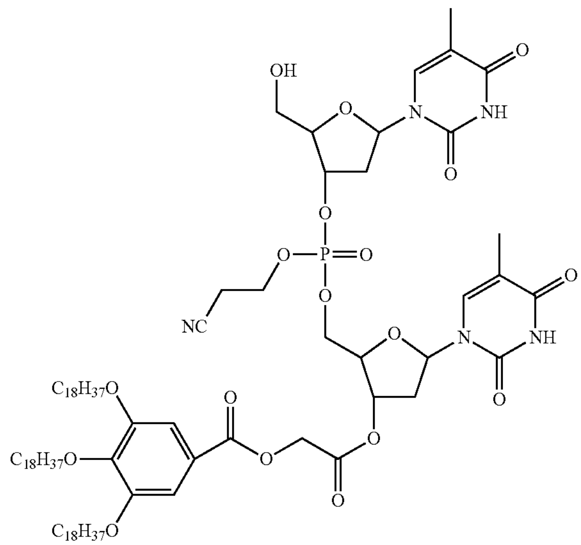

Under argon atmosphere, 5-benzylthio-1H-tetrazole (0.32 g, 1.65 mmol) was added to a suspension of thymidine-3'-yl 2-((3,4,5-tris(octadecyloxy)benzoyl)oxy)acetate (1.00 g, 0.83 mmol) and 5'-O-(4,4'-dimethoxytrityl) thymidine-3'-yl-phosphoroamidite (1.23 g, 1.65 mmol) in dichloromethane (15 mL), and then stirred at room temperature for 1.5 hours. Next, cumene hydroperoxide (content: 82%) (0.23 g, 1.24 mmol) was added, and then stirred at room temperature for 2 hours. Pyrrole (0.56 g, 8.27 mmol) and trifluoroacetic acid (0.28 g, 2.48 mmol) was added to the reaction solution, and then stirred at room temperature for 2 hours. The solid precipitated by dropping acetone (15 mL) and acetonitrile (45 mL) to the reaction solution was filtered. The solid was washed with acetonitrile-acetone-dichloromethane mixture solvent and acetonitrile, and then dried in vacuo at 50° C. to give the title compound (1.20 g, 92%) as a white solid.

$^1$H-NMR (400 MHz, $CDCl_3$): δ 0.88 (t, 9H, J=6.8 Hz), 1.11-1.55 (m, 90H), 1.65-2.05 (m, 12H), 2.40-2.60 (m, 4H), 2.75-2.90 (m, 2H), 3.84 (s, 2H), 3.95-4.10 (m, 6H), 4.15-4.50 (m, 6H), 4.85 (s, 2H), 5.15-5.25 (m, 1H), 5.35-5.55 (m, 1H), 6.10-6.35 (m, 2H), 7.29 (s, 2H), 7.35 (d, 1H, J=1.2 Hz), 7.47 (s, 1H), 9.60-9.95 (m, 2H).

$^{13}$C-NMR (100 MHz, $CDCl_3$): δ 12.42, 12.46, 14.10, 19.72, 19.79, 22.71, 26.12, 26.19, 29.38, 29.43, 29.49, 29.63, 29.70, 29.75, 30.43, 31.96, 36.47, 36.56, 38.46, 61.14, 61.91, 62.00, 62.63, 62.68, 62.75, 62.80, 67.53, 69.42, 73.64, 74.66, 74.77, 78.94, 79.12, 82.33, 82.40, 82.48, 85.60, 85.66, 85.79, 86.02, 86.21, 86.35, 108.61, 111.27, 111.33, 111.73, 111.82, 116.58, 116.66, 123.15, 135.87, 135.94, 136.53, 136.62, 143.41, 150.49, 150.59, 153.07, 163.94, 164.02, 165.69, 167.79, 167.83.

TOF/MS (ESI): calcd for $C_{86}H_{144}N_5O_{18}PNa$ $[M+Na]^+$ 1589.0142, found 1589.0104.

Example 2-4

(4) 5'-O-((2-Cyanoethoxy)(5'-O-((2-Cyanoethoxy)(5'-O-((2-Cyanoethoxy) (5'-O-((2'-Cyanoethoxy)(5'-O-((2'-Cyanoethoxy)(5'-O-((2'-Cyanoethoxy) (5'-O-((2'-Cyanoethoxy)(5'-O-((2-Cyanoethoxy)(5'-O-((2-Cyanoethoxy) (5'-O-((2-Cyanoethoxy)(5'-O-((2-Cyanoethoxy) (5'-O-((2'-Cyanoethoxy) (5'-O-((2'-Cyanoethoxy)(5'-O-((2'-Cyanoethoxy)(5'-O-((2'-Cyanoethoxy) (5'-O-((2-Cyanoethoxy)(5'-O-((2-Cyanoethoxy)(5'-O-((2-Cyanoethoxy) (5'-O-((2-Cyanoethoxy)(Thymidine-3'-Yl)Phosphoryl)-$N^4$Benzoyldeoxycytidine-3'-Yl)Phosphoryl)-$N^4$-Benzoyldeoxycytidine-3'-Yl)Phosphoryl)-$N^4$-Benzoyldeoxycytidine-3'-Yl)Phosphoryl)-$N^2$-Isobutyryldeoxyguanosine-3'-Yl)Phosphoryl)-$N^4$-Benzoyldeoxycytidine-3'-Yl)Phosphoryl)-$N^4$-Benzoyl Deoxycytidine-3'-Yl)Phosphoryl)-Thymidine-3'-Yl)Phosphoryl)-$N^2$-Isobutyryldeoxyguanosine-3'-Yl)Phosphoryl)-Thymidine-3'-Yl)Phosphoryl)-$N^2$-Isobutyryldeoxyguanosine-3'-Yl)Phosphoryl)-$N^6$-Benzoyldeoxyadenosine-3'-Yl)Phosphoryl)-$N^4$-Benzoyldeoxycytidine-3'-Yl)-Phosphoryl)-$N^6$-Benzoyldeoxyadenosine-3'-Yl)Phosphoryl)-Thymidine-3'-Yl)Phosphoryl)-$N^2$-Isobutyryldeoxyguanosine-3'-Yl)Phosphoryl)-$N^2$-Benzoyldeoxycytidine-3'-Yl)Phosphoryl)-$N^6$-Benzoyldeoxyadenosine-3'-Yl)Phosphoryl)-Thymidine-3'-Yl)Phosphoryl)-Thymidine-3'-Yl 2-((3,4,5-Tris(Octadecyloxy)Benzoyl)Oxy)Acetate The same procedure as in Example 2-3 was repeated 18 times to give the title compound (1.10 g)

TOF/MS (ESI): m/z 3114.3 $[M-3H]^{3-}$, 2335.6 $[M-4H]^{4-}$, 1868.9 $[M-5H]^{5-}$, 1557.6 $[M-6H]^{6-}$.

Example 2-5

(5) Deprotection and Purification Steps

28% ammonia water (2.1 mL) was added to the compound synthesized in Example 2-4 (50 mg, 5.4 μmol), and then heated and stirred at 80° C. for 1.5 hours. After concentrating the reaction solution under reduced pressure, the insoluble compound precipitated by dropping acetonitrile (50 mL) adding 0.1 mol/L-triethylamine acetate buffer to the concentrated residue was filtered. The eluate obtained by purifying C-18 cartridges of the filtrate was dried, and then Thymidinyl-[3'→5']-deoxycytidinyl-[3'→5']-deoxycytidinyl-[3'→5']-deoxycytidinyl-[3'→5']-deoxyguanidyl-[3'→5']-deoxycytidinyl-[3'→5']-deoxycytidinyl-[3'→5']-thymidinyl-[3'→5']-deoxyguanidyl-[3'→5']-thymidinyl-[3'→5']-deoxyguanidyl-[3'→5']-deoxyadenylyl-[3'→5']-deoxycyidinyl-[3'→5']-deoxyadenylyl-[3'→5']-thymidinyl-[3'→5']-deoxyguanidyl-[3'→5']-deoxycytidinyl-[3'→5']-deoxyadenylyl-[3'→5']-thymidinyl-[3'→5']-thymidine was obtained.

HPLC (shodexODP (4.6Φ×150 mm), flow rate: 1.0 mL/min, transfer: 0.1 mol/L triethylamine-acetate buffer, acetonitrile gradient: 0-15 min (2 to 98% acetonitrile), Rt=3.9 min (98.6%)

TOF/MS (ESI): m/z 3020.9 $[M-2H]^{2-}$, 2013.4 $[M-3H]^{3-}$, 1509.8 $[M-4H]^{4-}$.

(6) Synthesis of 5'-O-(4,4'-Dimethoxytrityl)Thymidine-3'-Yl 2-((3,4,5-Tris(Octadecyloxy)Benzoyl)Oxy)Acetate Example 2-6

(When EDCI-HCl is used as the condensing agent)

[Chemical Formula 50]

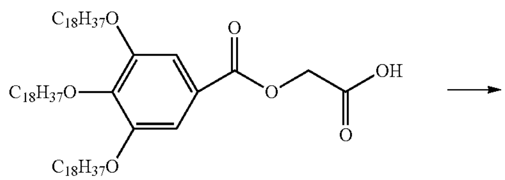

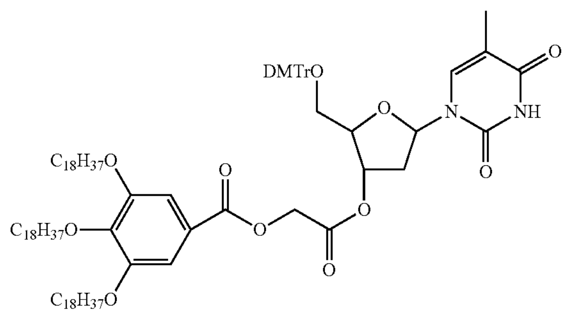

4-dimethylaminopyridine (0.02 g, 0.18 mmol) and 1-(3-dimethylaminopropyl)-3-ethylcarbodiimide hydrochloride (0.34 g, 1.77 mmol) was added to a solution of 2-((3,4,5-tris(octadecyloxy)benzoyl)oxy)acetic acid (0.87 g, 0.89 mmol) and 5'-O-(4,4'-dimethoxytrityl)thymidine (0.97 g, 1.77 mmol) in THF (9 mL), and then stirred at room temperature for 14 hours. The solid precipitated by dropping acetonitrile (18 mL) to the reaction solution was filtered. The solid was washed with acetonitrile—THF mixture solvent, and then dried under reduced pressure at 50° C. to obtain a crude compound (1.28 g). The crude compound was purified by column chromatography (spherical neutral silica gel, eluent: chloroform—THF) to give the title compound (1.06 g, 79%) as a white solid.

Example 2-7

(When CDI is used as the condensing agent)

[Chemical Formula 51]

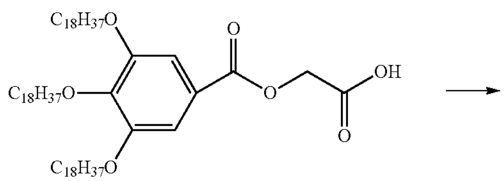

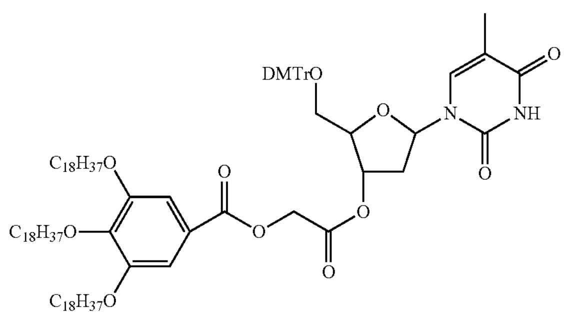

1,1'-carbonyldiimidazole (2.43 g, 15.0 mmol) was added to a suspension of dichloromethane (210 mL) of 2-((3,4,5-tris(octadecyloxy)benzoyl)oxy)acetic acid (9.86 g, 10.0 mmol) and 4-dimethylaminopyridine (0.12 g, 1.0 mmol) and stirred at room temperature for 1 hour, and then stirred at 30 to 35° C. for 4 hours. Next, 5'-O-(4,4'-dimethoxytrityl) thymidine (10.89 g, 20.0 mmol) was added, and then stirred at room temperature for 17 hours. Further, after 5'-O-(4,4'-dimethoxy trityl)thymidine (1.09 g, 0.4 mmol) was added to the reaction solution, the solution was stirred at room temperature for 4.5 hours. After dichloromethane (10 mL) was added to the reaction solution, the solid precipitated by dropping acetonitrile (400 mL) was filtered. The solid was washed with acetonitrile-dichloromethane mixture solvent, and then dried under reduced pressure at 50° C. to obtain a crude compound (14.44 g). The crude compound was purified by column chromatography (spherical neutral silica gel, eluent: dichloromethane—methanol) to give the title compound (11.11 g, 74%) as a white solid.

3. Synthesis of 5'-O-((2-Cyanoethoxy)(5'-O-((2-Cyanoethoxy)(5'-O-(4,4'-Dimethoxytrityl)-$N^2$-Isobutyryldeoxyguanosine-3'-Yl)Phosphoryl)Thymidine-3'-Yl)Phosphoryl)-$N^6$-Benzoyldeoxyadenosine-3'-Yl 2-((3,4,5-Tris(Octadecyloxy)Benzoyl)Oxy)Acetate Example 3-1

(1) Synthesis of 5'-O-(4,4'-Dimethoxytrityl)-$N^6$-Benzoyldeoxyadenosine-3'-Yl 2-((3,4,5-Tris(Octadecyloxy)Benzoyl)Oxy)Acetate

[Chemical Formula 52]

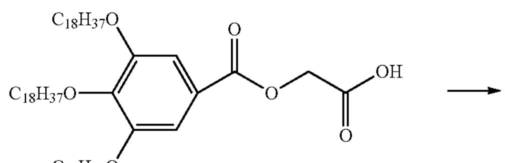

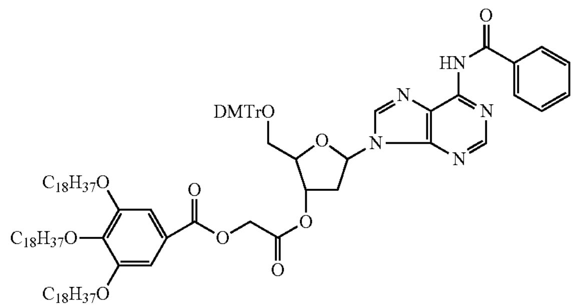

The title compound (3.11 g, 96%) was obtained from 2-((3,4,5-tris(octadecyloxy)benzoyl)oxy)acetic acid (1.97 g, 2.00 mmol) and 5'-O-(4,4'-dimethoxytrityl)-$N^6$-benzoyldeoxyadenosine (1.58 g, 2.40 m mol) according to the procedure of Example 2-1.

$^1$H-NMR (400 MHz, $CDCl_3$): δ 0.88 (t, 9H, J=6.8 Hz), 1.11-1.40 (m, 84H), 1.42-1.50 (m, 6H), 1.71-1.84 (m, 7H), 2.73 (dd, 1H, J=4.4, 12.8 Hz), 3.04-3.13 (m, 1H), 3.46 (d, 2H, J=4.0 Hz), 3.77 (s, 6H), 3.99-4.05 (m, 6H), 4.34-4.37 (m, 1H), 4.86 (s, 2H), 5.67 (d, 1H, J=5.6 Hz), 6.51 (dd, 1H, J=5.6, 8.4 Hz), 6.79 (d, 2H, J=9.4 Hz), 7.18-7.29 (m, 7H), 7.31 (s, 2H), 7.38 (d, 2H, J=7.2 Hz), 7.53 (dd, 2H, J=7.2, 7.6 Hz), 7.59-7.63 (m, 1H), 8.03 (d, 2H, J=7.2 Hz), 8.17 (s, 1H), 8.74 (s, 1H), 8.98 (s, 1H).

$^{13}$C-NMR (100 MHz, $CDCl_3$): δ 14.13, 22.71, 26.08, 26.11, 29.33, 29.38, 29.43, 29.60, 29.67, 29.74, 30.36, 31.94, 38.00, 55.23, 61.16, 63.52, 69.23, 73.58, 84.35, 84.48, 86.82, 108.35, 113.25, 123.22, 123.32, 127.03, 127.85, 127.95, 128.08, 128.91, 129.99, 130.04, 132.82, 133.66, 135.38, 135.42, 141.21, 143.07, 144.33, 149.53, 151.56, 152.75, 152.97, 158.63, 164.48, 165.89, 167.38.

TOF/MS (ESI): calcd for $C_{101}H_{149}N_5O_{12}Na$ $[M+Na]^+$ 1647.1100, found 1647.1149.

Example 3-2
(2) Synthesis of $N^6$-Benzoyldeoxyadenosine-3'-Yl 2-((3,4,5-Tris(Octadecyloxy)Benzoyl)Oxy)Acetate
[Chemical Formula 53]
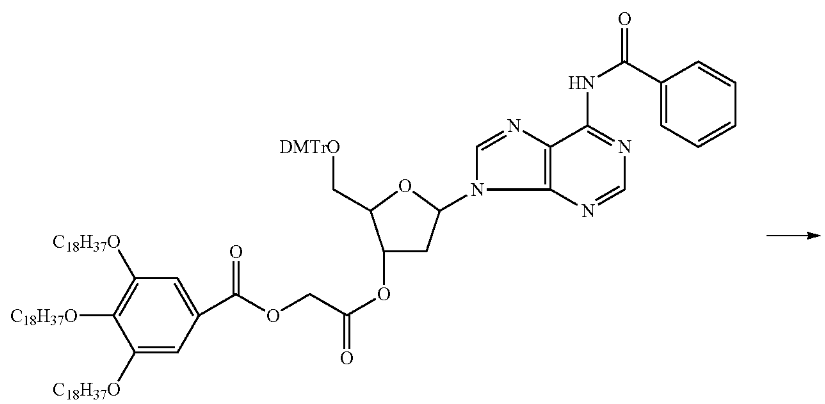
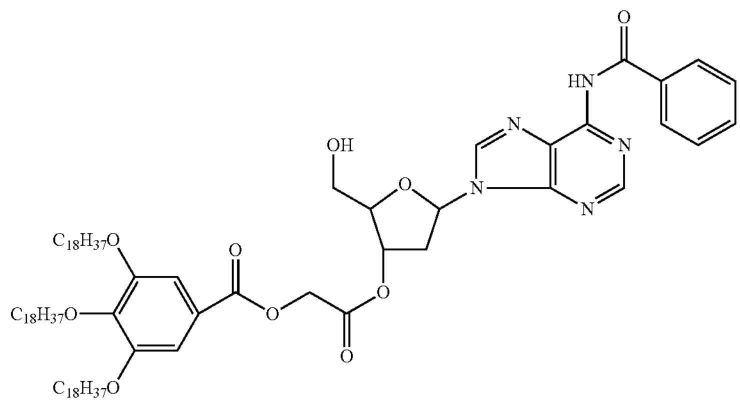

The title compound (2.25 g, 92%) was obtained from 5'-O-(4,4'-dimethoxytrityl)-$N^6$-benzoyldeoxyadenosine-3'-yl 2-((3,4,5-tris(octadecyloxy)benzoyl)oxy)acetate (3.00 g, 1.85 mmol) according to the procedure of Example 2-2.

$^1$H-NMR (400 MHz, $CDCl_3$): δ 0.88 (t, 9H, J=6.8 Hz), 1.11-1.40 (m, 84H), 1.44-1.50 (m, 6H), 1.71-1.85 (m, 7H), 2.53 (dd, 1H, J=5.6, 14.0 Hz), 3.21-3.28 (m, 1H), 3.89-3.96 (m, 1H), 3.98-4.06 (m, 6H), 4.36 (s, 1H), 4.87 (s, 2H), 5.70 (d, 1H, J=5.2 Hz), 5.91 (brs, 1H), 6.32 (dd, 1H, J=5.6, 10.0 Hz), 7.32 (s, 2H), 7.54 (dd, 2H, J=7.2, 8.0 Hz), 7.61-7.65 (m, 1H), 8.03 (d, 2H, J=7.2 Hz), 8.07 (s, 1H), 8.79 (s, 1H), 9.07 (s, 1H).

$^{13}$C-NMR (100 MHz, $CDCl_3$): δ 14.12, 22.70, 26.07, 26.11, 29.33, 29.37, 29.42, 29.59, 29.67, 29.73, 30.35, 31.94, 37.76, 61.20, 63.17, 69.28, 73.60, 87.18, 87.61, 108.39, 123.17, 124.66, 127.90, 128.96, 133.01, 133.39, 142.42, 143.17, 150.40, 150.68, 152.26, 153.00, 164.42, 165.97, 167.41.

TOF/MS (ESI): calcd for $C_{80}H_{131}N_5O_{10}Na$ $[M+Na]^+$ 1344.9794, found 1344.9828.

Example 3-3

(3) Synthesis of 5'-O-((2-Cyanoethoxy)(Thymidine-3'-Yl)Phosphoryl)-$N^6$-Benzoyldeoxyadenosine-3'-Yl 2-((3,4,5-Tris(Octadecyloxy)Benzoyl)Oxy)Acetate

[Chemical Formula 54]

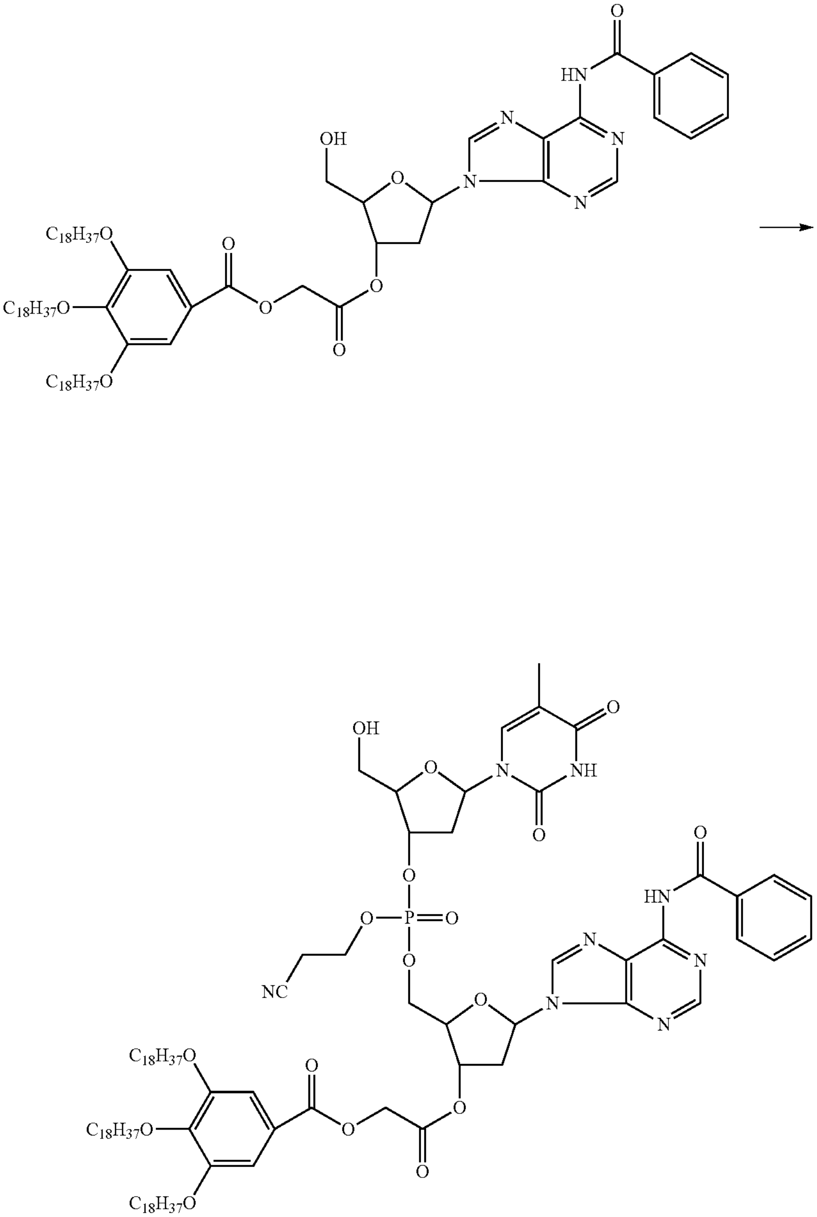

The title compound (2.50 g, 97%) was obtained from $N^6$-benzoyldeoxyadenosine-3'-yl 2-((3,4,5-tris(octadecyloxy)benzoyl)oxy)acetate (2.00 g, 1.51 mmol) and DMTr-dT-CE-phosphoroamidite (2.25 g, 3.02 mmol) according to the methods of Examples 2-3.

$^1$H-NMR (400 MHz, $CDCl_3$): δ 0.88 (t, 9H, J=6.8 Hz), 1.12-1.40 (m, 84H), 1.43-1.50 (m, 6H), 1.71-1.85 (m, 9H), 1.94 (s, 1H), 2.22-2.51 (m, 2H), 2.70-2.78 (m, 3H), 3.14-3.26 (m, 1H), 3.45-3.56 (m, 1H), 3.69-3.85 (m, 2H), 3.95-4.07 (m, 6H), 4.07-4.32 (m, 3H), 4.40-4.48 (m, 3H), 4.88 (s, 2H), 4.99-5.11 (m, 1H), 5.67-5.73 (m, 1H), 6.11-6.22 (m, 1H), 6.50-6.58 (m, 1H), 7.30 (s, 2H), 7.41-7.53 (m, 3H), 7.57-7.61 (m, 1H), 8.02-8.06 (m, 2H), 8.38 (m, 1H), 8.81 (m, 1H), 9.58-9.67 (m, 2H).

$^{13}$C-NMR (100 MHz, $CDCl_3$): δ 12.43, 14.14, 19.66, 19.73, 19.78, 22.71, 26.09, 26.15, 29.35, 29.38, 29.46, 29.61, 29.68, 29.74, 29.99, 30.38, 31.94, 36.57, 36.87, 38.35, 61.13, 61.84, 61.92, 62.45, 62.49, 62.58, 62.62, 67.39, 69.27, 73.61, 74.81, 75.06, 78.89, 79.19, 79.24, 82.98, 83.05, 83.12, 84.47, 84.54, 85.43, 85.48, 85.62, 85.67, 85.79, 85.93, 108.34, 111.22, 111.27, 116.52, 116.64, 123.01, 123.82, 124.08, 128.27, 128.31, 128.69, 128.72, 132.87, 132.94, 133.17, 133.41, 136.45, 141.68, 141.86, 143.18, 149.93, 150.00, 150.47, 151.84, 152.05, 152.67, 153.01, 163.81, 163.86, 165.43, 165.53, 165.99, 167.76.

TOF/MS (ESI): calcd for $C_{93}H_{147}N_8O_{17}PNa$ $[M+Na]^+$ 1702.0520, found 1702.0604.

Examples 3-4

(4) Synthesis of 5'-O-((2-Cyanoethoxy)(5'-O-((2-Cyanoethoxy)(5'-O-(4,4'-Dimethoxytrityl)-$N^2$-Isobutyryldeoxyguanosine-3'-Yl)Phosphoryl) Thymidine-3'-Yl)Phosphoryl-$N^6$-Benzoyldeoxyadenosine-3'-Yl 2-((3,4,5-Tris(Octadecyloxy)Benzoyl)Oxy)Acetate

[Chemical Formula 55]

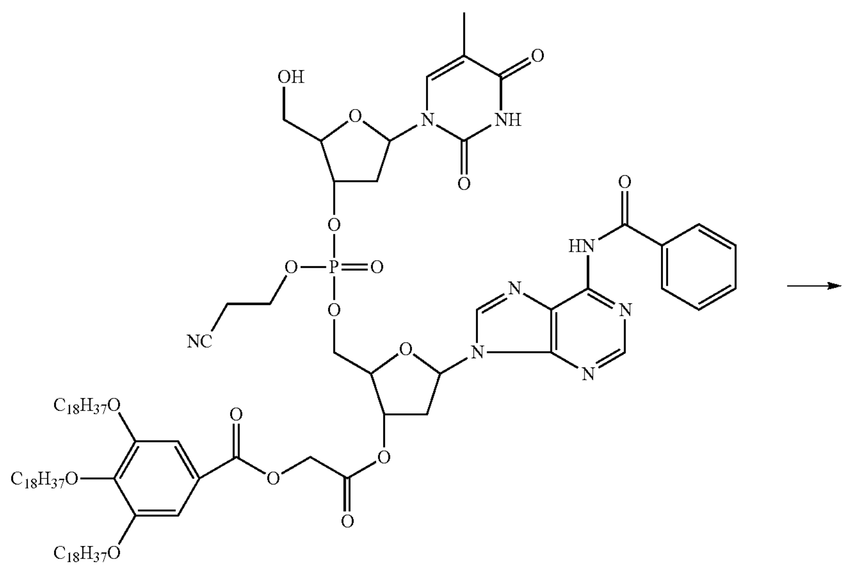

-continued

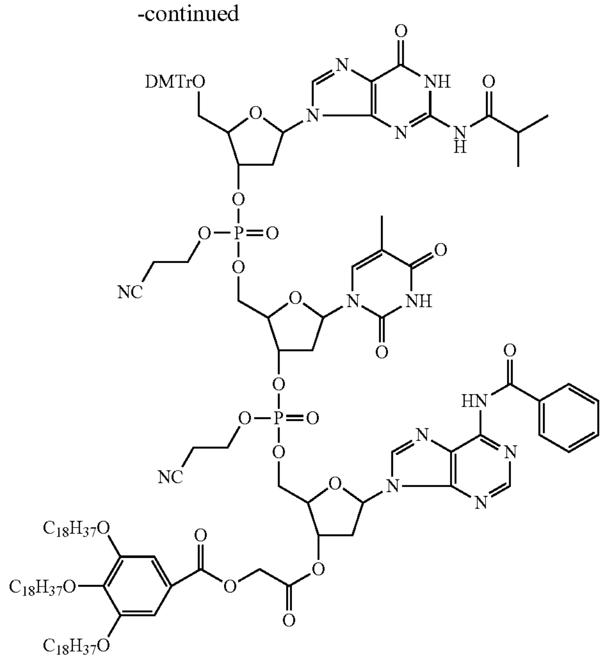

5-Benzylthio 1H tetrazole (2.74 g, 14.25 mmol) was added to a suspension of 5'-O-((2-cyanoethoxy)(thymidine-3'-yl)phosphoryl)-$N^6$-benzoyldeoxyadenosine-3'-yl 2-((3,4,5-tris(octadecyloxy)benzoyl)acetate (7.98 g, 4.75 mmol) and $N^2$-isobutyryl-DMTr-dG-CE phosphoroamidite (11.97 g, 14.25 mmol) in dichloromethane (90 ml), and then stirred at room temperature for 3 hours. Next, cumene hydroperoxide (content: 82%) (2.64 g, 14.25 mmol) was added, and then stirred at room temperature for 1 hours. The solid precipitated by dropping Acetone (120 mL) and acetonitrile (359 mL) to the reaction solution was filtered. The solid was washed with a mixture solvent of acetonitrile—acetone—dichloromethane, acetonitrile, and methanol, and then dried in vacuo at 50° C. to give the title compound (10.86 g, 94%).

$^1$H-NMR (400 MHz, $CDCl_3$): δ 0.88 (t, 9H, J=6.8 Hz), 1.12-1.40 (m, 90H), 1.43-1.50 (m, 6H), 1.71-1.93 (m, 9H), 1.95-2.16 (m, 2H), 2.35-2.87 (m, 9H), 3.16-3.37 (m, 3H), 3.76 (s, 6H), 3.99-4.05 (m, 6H), 4.09-4.43 (m, 10H), 4.86 (s, 2H), 5.07-5.26 (m, 2H), 5.65-5.71 (m, 1H), 5.91-6.22 (m, 2H), 6.49-6.54 (m, 1H), 6.78 (d, 4H, J=8.4 Hz), 7.15-7.27 (m, 8H), 7.30 (s, 2H), 7.34-7.36 (m, 2H), 7.43-7.48 (m, 2H), 7.54-7.59 (m, 1H), 7.69-7.71 (m, 1H), 7.98-8.02 (m, 2H), 8.30-8.41 (m, 1H), 8.75-8.82 (m, 1H), 9.43-9.58 (m, 1H), 9.88-10.27 (m, 1H), 12.09-12.22 (m, 1H).

$^{13}$C-NMR (100 MHz, $CDCl_3$): δ 12.23, 12.36, 14.13, 18.84, 19.00, 19.05, 19.65, 19.73, 22.70, 26.09, 26.15, 29.35, 29.37, 29.46, 29.61, 29.68, 29.74, 29.77, 30.38, 31.94, 35.89, 36.47, 36.63, 55.26, 61.13, 62.47, 62.63, 62.68, 63.42, 67.55, 69.28, 73.61, 74.86, 75.05, 79.76, 81.43, 83.08, 83.59, 84.68, 86.85, 108.33, 111.11, 111.17, 113.15, 113.26, 116.48, 116.75, 116.88, 121.42, 121.59, 123.03, 124.05, 127.07, 127.12, 127.78, 127.85, 127.98, 128.06, 128.74, 129.14, 130.05, 132.88, 133.37, 135.23, 139.48, 141.92, 142.01, 143.18, 144.23, 147.35, 148.11, 148.27, 148.49, 149.98, 150.09, 151.80, 152.60, 153.01, 155.40, 155.47, 158.62, 158.68, 164.77, 165.20, 165.96, 167.71, 167.74, 179.81, 180.21.

TOF/MS (ESI): calcd for $C_{131}H_{186}N_{14}O_{26}P_2Na$ $[M+Na]^+$ 2456.3036, found 2456.2988.

Synthesis of 5'-O-((2-Cyanoethoxy)(5'-O-((2-Cyanoethoxy)(5'-O-(4,4'-Dimethoxytrityl)Thymidine-3'-Yl)Phosphoryl)-$N^2$-Isobutyryldeoxyguanosine-3'-Yl) Phosphoryl)-$N^4$-Benzoyldeoxycytidine-3'-Yl 2-((3,4,5-Tris(Octadecyloxy)Benzoyl)Oxy)Acetate Example 3-5

(1) Synthesis of 5'-O-(4,4'-Dimethoxytrityl)-$N^4$-Benzoyldeoxycytidine-3'-Yl 2-((3,4,5-Tris(Octadecyloxy)Benzoyl)Oxy)Acetate

[Chemical Formula 56]

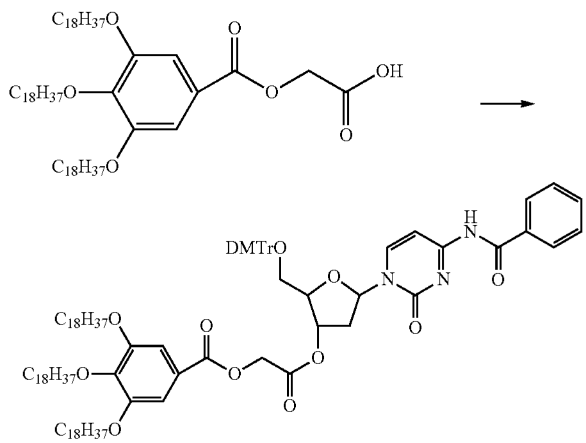

The title compound (3.10 g, 97%) was obtained from 2-((3,4,5-tris(octadecyloxy)benzoyl)oxy)acetic acid (1.97 g, 2.00 mmol) and 5'-O-(4,4'-dimethoxytrityl)-$N^4$-benzoyldeoxycytidine (1.52 g, 2.40 mmol) according to the procedure of Example 2-1.

$^1$H-NMR (400 MHz, $CDCl_3$): δ 0.88 (t, 9H, J=6.8 Hz), 1.12-1.53 (m, 90H), 1.71-1.85 (m, 6H), 2.36-2.43 (m, 1H), 2.83-2.95 (m, 1H), 3.49 (ddd, 2H, J=3.2, 10.4, 18.0 Hz), 3.78 (s, 3H), 3.79 (s, 3H), 3.95-4.07 (m, 6H), 4.30-4.35 (m, 1H), 4.83 (dd, 2H, J=16.0, 23.6 Hz), 5.51-5.58 (m, 1H), 6.33 (dd, 1H, J=6.0, 7.6 Hz), 6.86 (dd, 4H, J=2.4, 8.8 Hz), 7.20-7.38 (m, 11H), 7.50-7.54 (m, 2H), 7.60-7.64 (m, 1H), 7.88 (d, 2H, J=7.2 Hz), 8.14 (d, 1H, J=7.6 Hz), 8.40-8.60 (brs, 1H).
$^{13}$C-NMR (100 MHz, $CDCl_3$): δ 14.09, 22.70, 26.10, 26.15, 29.38, 29.46, 29.61, 29.68, 29.75, 30.40, 31.95, 39.47, 55.26, 61.10, 63.17, 69.33, 73.59, 75.77, 84.68, 87.32, 108.54, 113.46, 123.32, 127.22, 128.10, 128.13, 129.10, 130.04, 130.10, 133.20, 135.13, 135.30, 144.07, 153.01, 158.84, 165.81, 167.43.
TOF/MS (ESI): calcd for $C_{100}H_{149}N_3O_{13}Na$ [M+Na]$^+$ 1623.0988, found 1623.1069.
Examples 3-6
(2) Synthesis of N$^4$-Benzoyldeoxycytidine-3'-Yl 2-((3,4,5-Tris(Octadecyloxy)Benzoyl)Oxy)Acetate
[Chemical Formula 57]
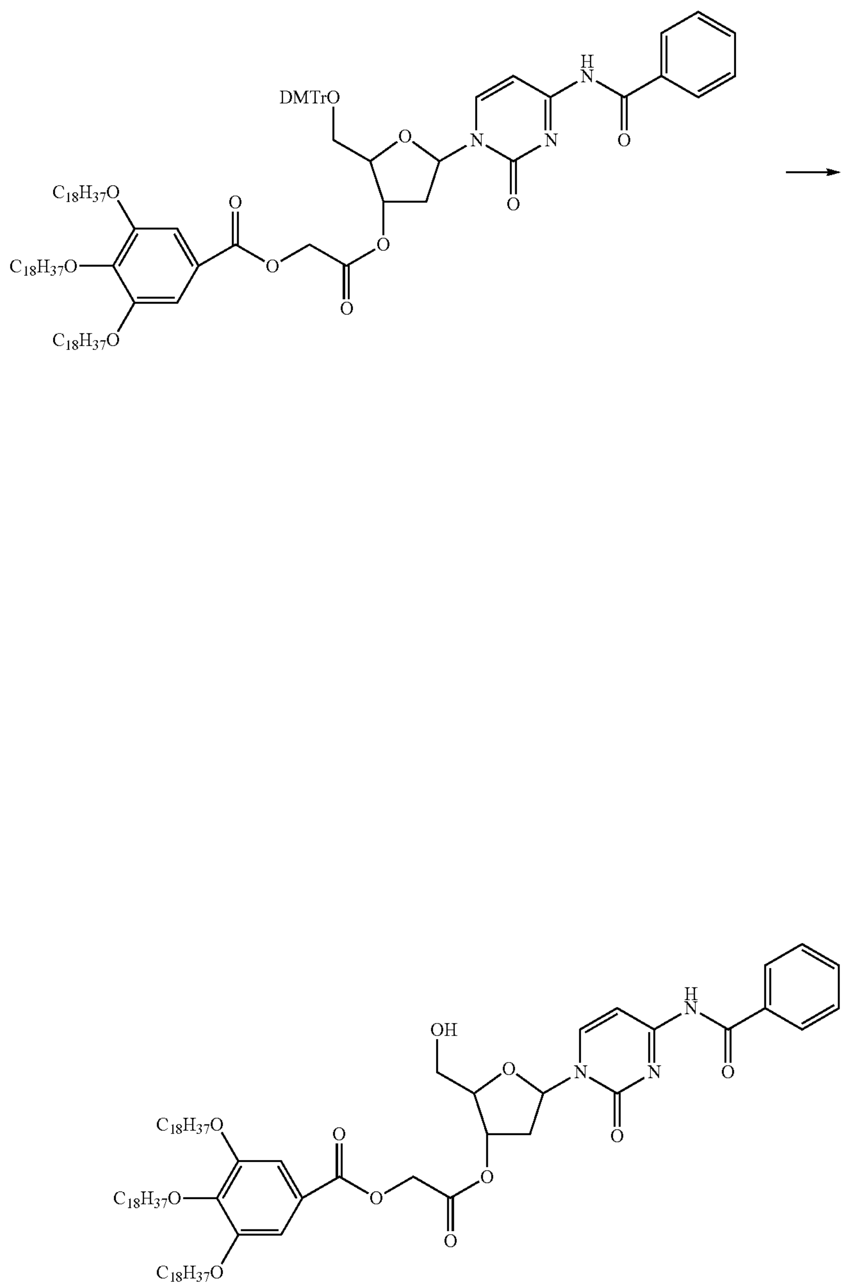

The title compound (2.39 g, 97%) was obtained from 5'-O-(4,4'-dimethoxytrityl)-$N^6$-benzoyldeoxycytidine-3'-yl 2-((3,4,5-tris(octadecyloxy)benzoyl)oxy)acetate (3.04 g, 1.90 mmol) according to the procedure of Example 2-2.

$^1$H-NMR (400 MHz, $CDCl_3$): δ 0.88 (t, 9H, J=6.8 Hz), 1.20-1.51 (m, 90H), 1.71-1.85 (m, 6H), 2.46-2.53 (m, 1H), 2.69-2.80 (m, 1H), 3.92-4.04 (m, 8H), 4.27 (d, 1H, J=2.4 Hz), 4.84 (dd, 2H, J=16.4, 20.4 Hz), 5.51-5.53 (m, 1H), 6.26 (dd, 1H, J=5.6, 7.6 Hz), 7.29 (s, 2H), 7.48-7.62 (m, 4H), 7.88 (d, 2H, J=7.6 Hz), 8.28 (d, 1H, J=7.2 Hz), 8.66-8.91 (brs, 1H).

$^{13}$C-NMR (100 MHz, $CDCl_3$): δ 14.10, 22.71, 26.10, 26.14, 29.38, 29.45, 29.61, 29.68, 29.75, 30.39, 31.95, 38.46, 61.15, 62.37, 69.34, 73.61, 75.80, 85.82, 88.44, 108.55, 123.25, 127.61, 129.07, 133.25, 143.25, 145.32, 153.01, 162.38, 165.89, 167.79.

TOF/MS (ESI): calcd for $C_{79}H_{131}N_3O_{11}Na$ $[M+Na]^+$ 1320.9681, found 1320.9723.

Examples 3-7

(3) Synthesis of 5'-O-((2-Cyanoethoxy)($N^2$-Isobutyryldeoxyguanosine-3'-Yl)Phosphoryl)-$N^4$-Benzoyldeoxycytidine-3'-Yl 2-((3,4,5-Tris(Octa Decyloxy) Benzoyl)Oxy)Acetate

[Chemical Formula 58]

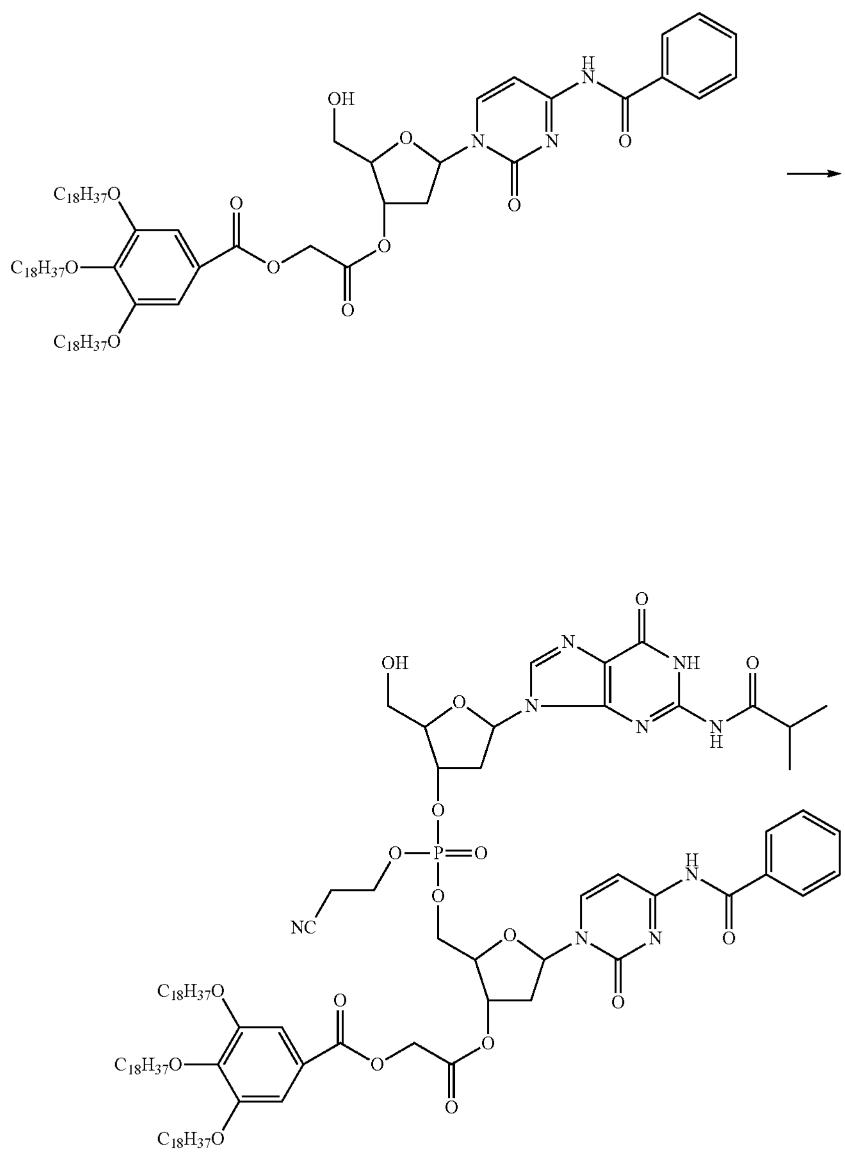

The title compound (3.02 g, 99%) was obtained from $N^4$-benzoyldeoxycytidine-3'-yl 2-((3,4,5-tris(octadecyloxy) benzoyl)oxy)acetate (2.27 g, 1.75 mmol) and $N^2$-isobutyryl-DMTr-dG-CE-phosphoroamidite (2.94 g, 3.50 mmol) according to the methods of Examples 2-3.

$^1$H-NMR (400 MHz, $CDCl_3$): δ 0.88 (t, 9H, J=6.8 Hz), 1.08-1.53 (m, 96H), 1.70-1.84 (m, 6H), 2.36-2.62 (m, 2H), 2.75-3.30 (m, 7H), 3.75-3.87 (m, 2H), 3.98-4.04 (m, 6H), 4.26-4.53 (m, 6H), 4.78-4.89 (m, 2H), 5.26-5.29 (m, 1H), 5.42-5.52 (m, 1H), 5.92-6.11 (m, 1H), 6.24-6.38 (m, 1H), 7.26-7.28 (m, 2H), 7.38-7.67 (m, 4H), 7.80-7.89 (m, 2H), 7.95-8.00 (m, 1H), 8.14-8.24 (m, 1H), 10.22-10.70 (m, 1H), 12.08-12.22 (m, 1H).

$^{13}$C-NMR (100 MHz, $CDCl_3$): δ 14.14, 18.96, 18.99, 19.05, 19.81, 19.87, 22.71, 26.08, 26.15, 29.34, 29.38, 29.46, 29.61, 29.68, 29.75, 30.37, 31.94, 36.01, 36.06, 38.37, 38.83, 39.11, 61.09, 62.01, 62.59, 62.64, 62.77, 62.82, 67.20, 67.51, 69.25, 73.60, 74.76, 75.03, 80.49, 83.50, 83.75, 84.57, 84.81, 86.32, 87.91, 88.04, 97.29, 97.50, 108.30, 116.55, 116.68, 120.72, 121.05, 123.01, 127.73, 127.80, 128.88, 128.93, 132.71, 132.81, 133.28, 138.19, 138.30, 143.13, 144.20, 144.42, 147.79, 147.99, 148.16, 148.33, 152.99, 155.25, 155.65, 162.86, 163.04, 165.92, 165.95, 167.77, 167.85, 179.77, 180.03.

TOF/MS (ESI): calcd for $C_{96}H_{152}N_9O_{18}PNa$ $[M+Na]^+$ 1773.0891, found 1773.0914.

Examples 3-8

(4) Synthesis of 5'-O-((2-Cyanoethoxy)(5'-O-((2-Cyanoethoxy)(5'-O-(4,4'-Dimethoxytrityl)Thymidine-3'-Yl)Phosphoryl)-$N^2$-Isobutyryldeoxyguanosine-3'-Yl)Phosphoryl)-$N^4$-Benzoyldeoxycytidine-3'-Yl 2-((3,4,5-Tris(Octadecyloxy)Benzoyl)Oxy) Acetate

[Chemical Formula 59]

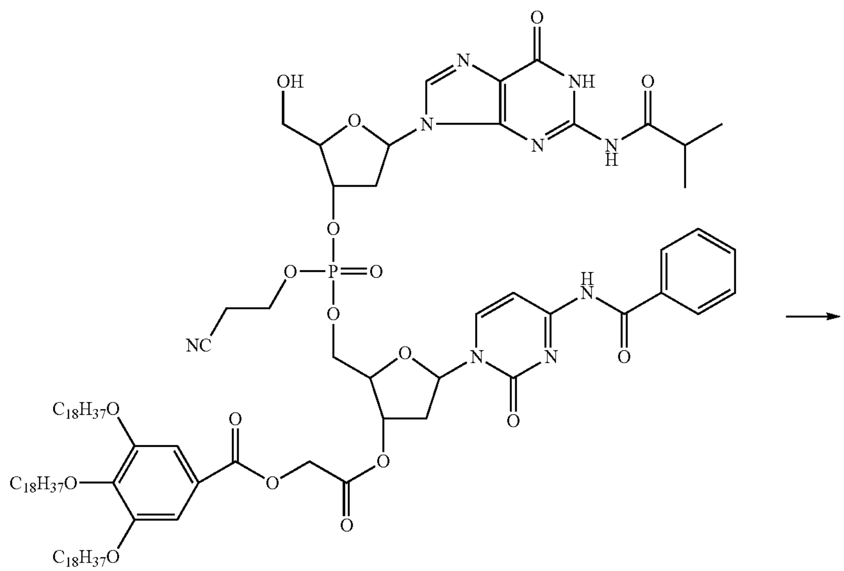

-continued

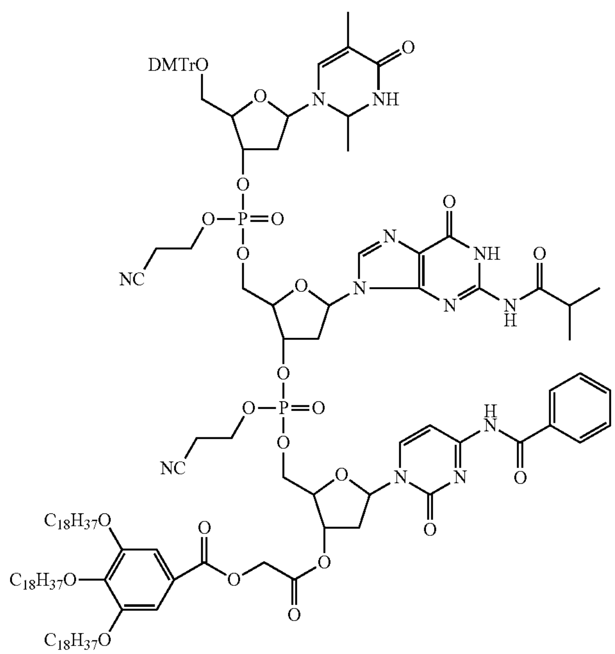

The title compound (3.44 g, 89%) was obtained from 5'-O-((2-cyanoethoxy)($N^2$-isobutyryldeoxyguanosine-3'-yl) phosphoryl)-$N^4$-benzoyldeoxycytidine-3'-yl 2-((3,4,5-tris (octadecyloxy)benzoyl)oxy)acetate (2.80 g, 1.60 mmol) and DMTr-dT-CE phosphoroamidite (3.58 g, 4.80 mmol) according to the methods of Examples 3-4.

$^1$H-NMR (400 MHz, $CDCl_3$): δ 0.88 (t, 9H, J=6.8 Hz), 1.13-1.55 (m, 99H), 1.71-1.84 (m, 6H), 1.95-2.14 (m, 2H), 2.27-2.95 (m, 9H), 3.00-3.55 (m, 3H), 3.73-3.81 (m, 6H), 3.99-4.04 (m, 6H), 4.14-4.48 (m, 11H), 4.82-4.85 (m, 2H), 5.05-5.53 (m, 3H), 6.00-6.46 (m, 3H), 6.76-6.87 (m, 4H), 7.20-7.36 (m, 11H), 7.44-7.64 (m, 4H), 7.72-7.88 (m, 3H), 8.11-8.22 (m, 1H), 9.00-9.15 (m, 1H), 10.29-10.49 (m, 1H), 12.14-12.17 (m, 1H).

$^{13}$C-NMR (100 MHz, $CDCl_3$): δ 11.67, 11.71, 14.13, 18.86, 18.90, 18.94, 18.98, 19.00, 19.59, 19.67, 19.81, 19.88, 22.70, 26.08, 26.15, 29.35, 29.37, 29.46, 29.61, 29.67, 29.74, 29.77, 30.37, 31.94, 35.88, 38.67, 55.29, 61.13, 62.66, 62.73, 62.87, 63.33, 69.25, 73.59, 84.20, 84.28, 85.31, 87.29, 108.31, 111.69, 111.73, 113.15, 113.35, 116.64, 116.79, 123.01, 127.31, 127.71, 127.77, 128.08, 128.99, 129.14, 130.09, 133.33, 134.93, 134.97, 135.01, 135.17, 143.14, 143.96, 144.04, 147.84, 147.93, 148.16, 150.40, 150.48, 152.99, 155.48, 158.83, 163.52, 165.96, 167.86, 179.65, 179.76.

TOF/MS (ESI): calcd for $C_{130}H_{186}N_{12}O_{27}P_2Na$ $[M+Na]^+$ 2432.2923, found 2432.2937.

Synthesis of 5'-O-((2-Cyanoethoxy)(5'-O-((2-Cyanoethoxy)(5'-O-(4,4'-Dimethoxytrityl)Thymidine-3'-Yl)Phosphoryl)Thymidine-3'-Yl)Phosphoryl)-$N^2$-Isobutyryldeoxyguanosine-3'-Yl 2-((3,4,5-Tris (Octadecyloxy)Benzoyl)Oxy)Acetate Examples 3-9

(1) Synthesis of 5'-O-(4,4'-Dimethoxytrityl)-$N^2$-Isobutyryldeoxyguanosine-3'-Yl 2-((3,4,5-Tris(Octadecyloxy)Benzoyl)Oxy)Acetate

[Chemical Formula 60]

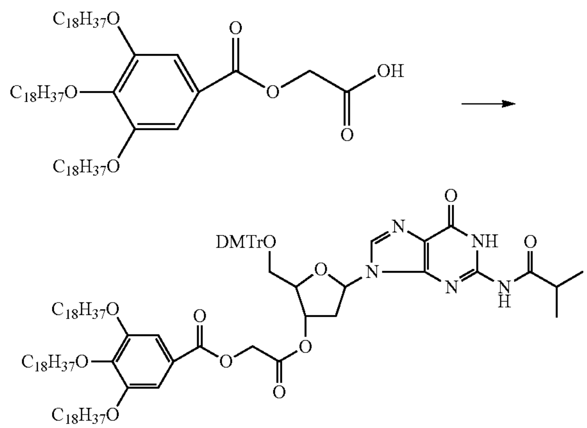

The title compound (3.14 g, 98%) was obtained from 2-((3,4,5-tris(octadecyloxy)benzoyl)oxy)acetic acid (1.97 g, 2.00 mmol) and 5'-O-(4,4'-dimethoxytrityl)-$N^2$-isobutyryldeoxyguanosine (1.54 g, 2.40 mmol) according to the procedure of Example 2-1.

$^1$H-NMR (400 MHz, $CDCl_3$): δ 0.86-0.89 (m, 12H), 1.03 (d, 3H, J=6.8 Hz), 1.11-1.40 (m, 84H), 1.42-1.50 (m, 6H), 1.70-1.83 (m, 6H), 1.95 (sept, 1H, J=6.8 Hz), 2.51 (dd, 1H, J=5.2, 12.4H z), 3.17-3.29 (m, 2H), 3.42 (dd, 1H, J=3.2, 10.4 Hz), 3.76 (s, 3H), 3.77 (s, 3H), 3.98-4.05 (m, 6H), 4.22 (s, 1H), 4.83 (s, 2H), 5.70 (d, 1H, J=6.0 Hz), 6.07 (dd, 1H, J=5.2, 9.2 Hz), 6.76-6.82 (m, 4H), 7.16-7.38 (m, 9H), 7.43-7.50 (m, 2H), 7.71 (s, 1H), 7.73 (s, 1H), 11.96 (s, 1H).

$^{13}$C-NMR (100 MHz, $CDCl_3$): δ 14.13, 18.64, 18.77, 22.71, 26.05, 26.11, 29.32, 29.37, 29.42, 29.60, 29.66, 29.68, 29.74, 29.75, 29.77, 30.33, 31.94, 36.17, 37.21, 55.24, 61.24, 63.48, 69.30, 73.64, 76.16, 83.94, 84.44, 86.49, 108.33, 113.27, 113.29, 122.34, 123.24, 127.15, 128.02, 129.99, 135.47, 135.77, 137.83, 143.04, 144.70, 147.18, 148.02, 152.94, 155.38, 158.74, 166.00, 167.35, 178.30.

TOF/MS (ESI): calcd for $C_{98}H_{151}N_5O_{13}Na$ $[M+Na]^+$ 1629.1206, found 1629.1240.

Examples 3-10

(2) Synthesis of $N^2$-Isobutyryldeoxyguanosine-3'-Yl 2-((3,4,5-Tris(Octadecyloxy)Benzoyl)Oxy)Acetate

[Chemical Formula 61]

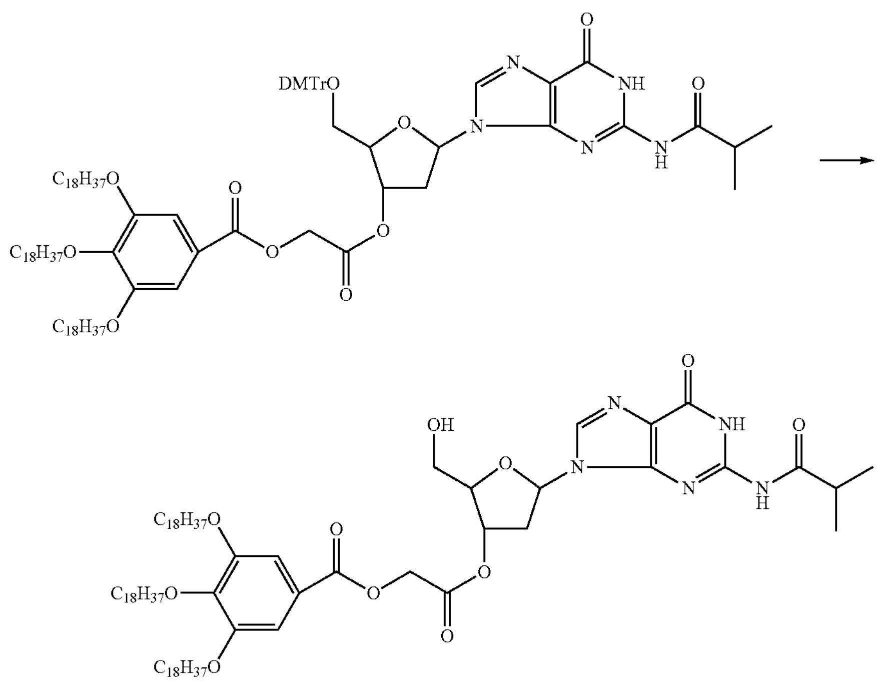

The title compound (2.42 g, 98%) was obtained from 5'-O-(4,4'-dimethoxytrityl)-$N^2$-isobutyryldeoxyguanosine-3'-yl 2-((3,4,5-tris(octadecyloxy)benzoyl)oxy)acetate (3.05 g, 1.90 mmol) according to the procedure of Example 2-2.

$^1$H-NMR (400 MHz, $CDCl_3$): δ 0.88 (t, 9H, J=6.8 Hz), 1.20-1.50 (m, 96H), 1.71-1.85 (m, 6H), 2.48 (dd, 1H, J=5.6, 14.0 Hz), 2.72 (sept, 1H, J=6.8 Hz), 2.97-3.05 (m, 1H), 3.49 (brs, 2H), 3.86-4.05 (m, 8H), 4.26 (s, 1H), 4.86 (s, 2H), 5.59 (d, 1H, J=6.0), 6.13 (dd, 1H, J=5.6, 9.2 Hz), 7.30 (s, 2H), 7.86 (s, 2H), 8.82 (s, 1H), 12.16 (s, 1H).

$^{13}$C-NMR (100 MHz, $CDCl_3$): δ 14.10, 18.94, 18.97, 22.71, 26.09, 26.15, 29.38, 29.45, 29.61, 29.69, 29.75, 30.39, 31.96, 36.50, 37.85, 61.26, 62.92, 69.43, 73.67, 86.27, 86.34, 108.59, 122.49, 123.26, 138.42, 143.34, 147.09, 147.73, 153.04, 155.01, 166.02, 167.52, 178.69.

TOF/MS (ESI): calcd for $C_{77}H_{133}N_5O_{11}Na$ $[M+Na]^+$ 1326.9899, found 1326.9879.

Example 3-11

(3) Synthesis of 5'-O-((2-Cyanoethoxy)(Thymidine-3'-Yl)Phosphoryl)-$N^2$-Isobutyryldeoxyguanosine-3'-Yl 2-((3,4,5-Tris(Octadecyloxy)Benzoyl)Oxy)Acetate

[Chemical Formula 62]

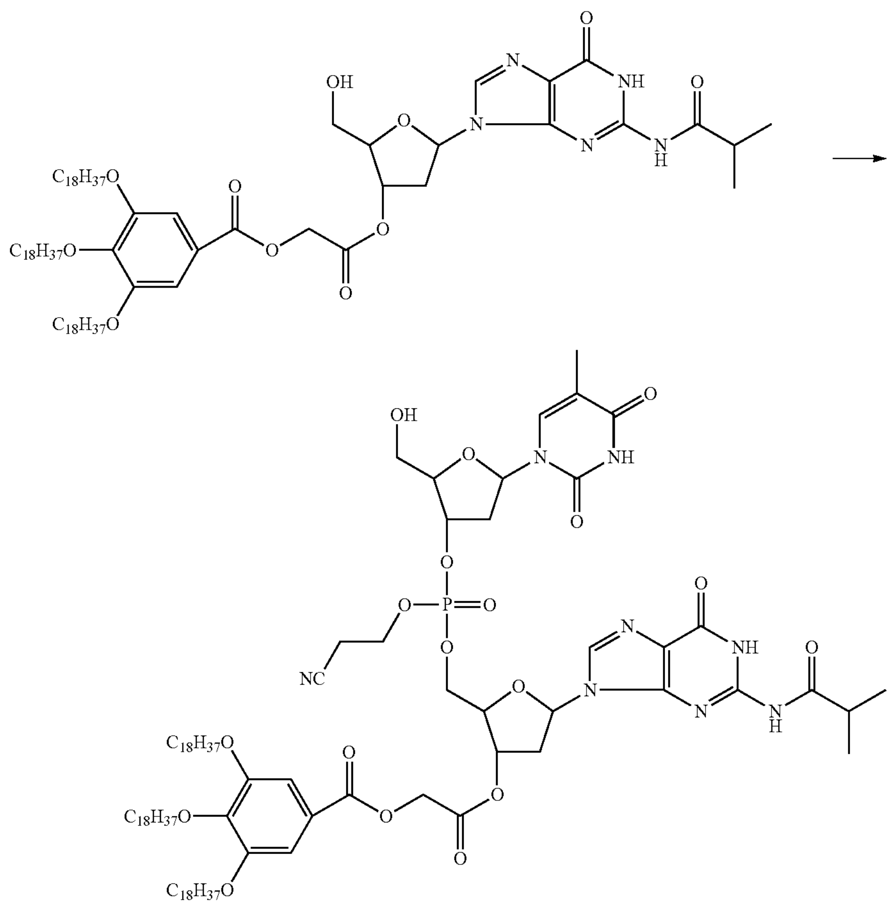

The title compound (2.68 g, 94%) was obtained from $N^2$-isobutyryldeoxyguanosine-3'-yl 2-((3,4,5-tris(octadecyloxy)benzoyl)oxy)acetate (2.25 g, 1.72 mmol) and DMTr-dT-CE-phosphoroamidite (2.57 g, 3.45 mmol) according to the methods of Examples 2-3.

$^1$H-NMR (400 MHz, $CDCl_3$): δ 0.88 (t, 9H, J=6.8 Hz), 1.05-1.52 (m, 96H), 1.71-1.89 (m, 9H), 2.24-2.78 (m, 8H), 3.38-3.49 (m, 1H), 3.69-4.05 (m, 8H), 4.17-4.89 (m, 7H), 5.20-5.29 (m, 1H), 5.55-5.66 (m, 1H), 6.08-6.24 (m, 2H), 7.30 (s, 2H), 7.42-7.54 (m, 1H), 7.68-7.73 (m, 1H), 8.64-8.83 (m, 1H), 10.20-10.32 (m, 1H), 12.11-12.22 (m, 1H).

$^{13}$C-NMR (100 MHz, $CDCl_3$): δ 12.46, 14.14, 18.59, 18.93, 19.06, 19.42, 19.66, 19.71, 19.73, 19.78, 22.71, 26.07, 26.14, 29.33, 29.38, 29.45, 29.61, 29.68, 29.74, 30.36, 31.94, 35.57, 35.93, 38.42, 61.12, 61.24, 61.71, 61.89, 62.56, 62.64, 62.69, 69.26, 73.62, 75.69, 75.81, 79.29, 82.80, 85.73, 86.04, 86.41, 108.29, 111.23, 111.32, 116.46, 116.51, 122.39, 122.98, 123.03, 136.55, 136.78, 139.04, 143.11, 143.18, 147.93, 147.98, 150.30, 150.37, 152.98, 155.39, 155.59, 163.53, 163.62, 166.00, 166.12, 167.69, 167.86, 179.92, 180.04.

TOF/MS (ESI): calcd for $C_{90}H_{149}N_8O_{18}PNa$ $[M+Na]^+$ 1684.0625, found 1684.0648.

Example 3-12

(4) Synthesis of 5'-O-((2-Cyanoethoxy)(5'-O-((2-Cyanoethoxy)(5'-O-(4,4'-Dimethoxytrityl)Thymidine-3'-Yl)Phosphoryl)Thymidine-3'-Yl)Phosphoryl)-$N^2$-Isobutyryldeoxyguanosine-3'-Yl 2-((3,4,5-Tris(Octadecyloxy)Benzoyl)Oxy)Acetate

[Chemical Formula 63]

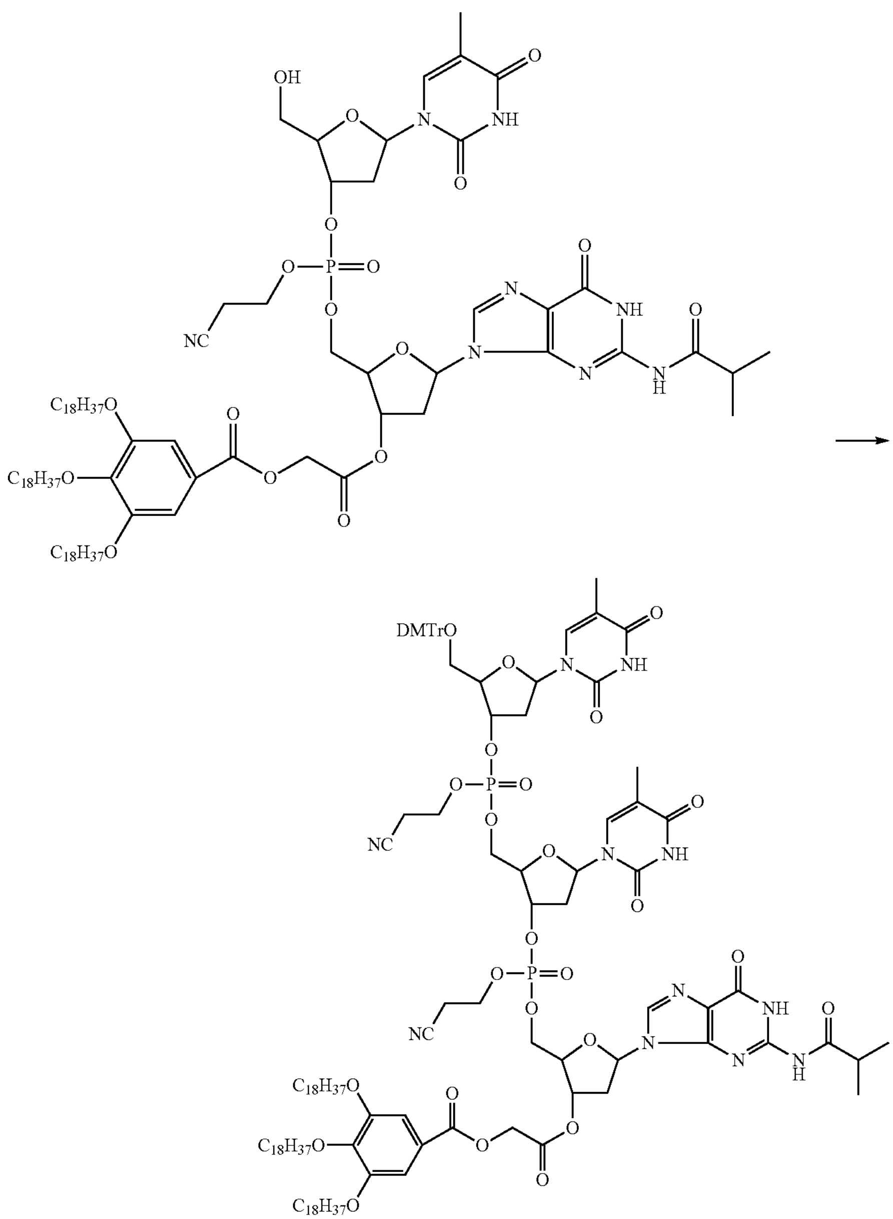

The title compound (3.11 g, 89%) was obtained from 5'-O-((2-cyanoethoxy)(thymidine-3'-yl)phosphoryl)-$N^2$-isobutyryldeoxyguanosine-3'-yl 2-((3,4,5-tris(octadecyloxy) benzoyl)oxy)acetate (2.50 g, 1.50 mmol) and DMTr-dT-CE phosphoroamidite (3.36 g, 4.51 mmol) according to the methods of Examples 3-4.

$^1$H-NMR (400 MHz, $CDCl_3$): δ 0.88 (t, 9H, J=6.4 Hz), 1.05-1.53 (m, 96H), 1.71-1.88 (m, 13H), 2.24-2.87 (m, 10H), 3.25-3.53 (m, 3H), 3.72-3.81 (m, 7H), 3.95-4.05 (m, 6H), 4.05-4.72 (m, 10H), 4.81-4.91 (m, 2H), 5.03-5.24 (m, 2H), 5.55-5.61 (m, 1H), 5.95-6.43 (m, 3H), 6.82-6.85 (m, 4H), 7.18-7.37 (m, 12H), 7.53 (s, 1H), 7.73 (s, 1H), 9.10-9.31 (m, 2H), 10.05-10.09 (m, 1H), 12.18 (s, 1H).

$^{13}$C-NMR (100 MHz, $CDCl_3$): δ 11.68, 11.72, 12.33, 12.37, 14.14, 18.78, 18.88, 19.13, 19.24, 19.58, 19.65, 19.70, 19.77, 22.70, 26.08, 26.16, 29.34, 29.38, 29.46, 29.62, 29.68, 29.74, 29.77, 30.36, 31.94, 35.84, 35.99, 37.65, 38.95, 55.29, 61.18, 62.62, 62.77, 62.83, 63.26, 67.10, 67.45, 69.27, 73.63, 75.55, 79.91, 82.62, 82.87, 84.27, 87.31, 108.29, 111.50, 111.80, 113.15, 113.35, 116.66, 116.74, 116.86, 122.51, 122.59, 123.07, 127.32, 128.08, 128.13, 129.13, 130.13, 134.95, 135.12, 136.32, 138.75, 143.10, 143.99, 147.93, 147.97, 148.04, 150.28, 150.37, 150.60, 150.69, 152.98, 155.49, 155.54, 158.81, 163.63, 163.68, 163.79, 166.02, 167.69, 167.71, 179.73, 179.77.

TOF/MS (ESI): calcd for $C_{124}H_{183}N_{11}O_{27}P_2Na$ $[M+Na]^+$ 2343.2658, found 2343.2742.

Synthesis of 5'-O-((2-Cyanoethoxy)(5'-O-((2-Cyanoethoxy)(5'-O-(4,4'-Dimethoxytrityl)Thymidine-3'-Yl)Phosphoryl)-$N^2$-Isobutyryldeoxyguanosine-3'-Yl) Phosphoryl)Thymidine-3'-Yl 2-((3,4,5-Tris (Octadecyloxy)Benzoyl)Oxy)Acetate

Example 3-13

(1) Synthesis of 5'-O-((2-Cyanoethoxy)($N^2$-Isobutyryldeoxyguanosine-3'-Yl)Phosphoryl)Thymidine-3'-Yl 2-((3,4,5-Tris(Octadecyloxy)Benzo Yl)Oxy) Acetate

[Chemical Formula 64]

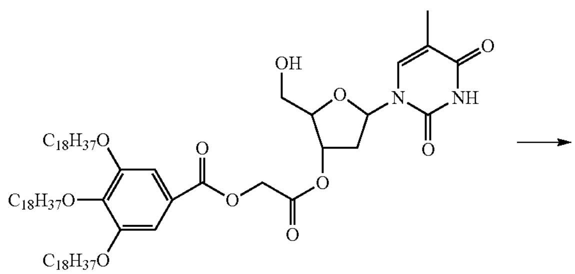

-continued

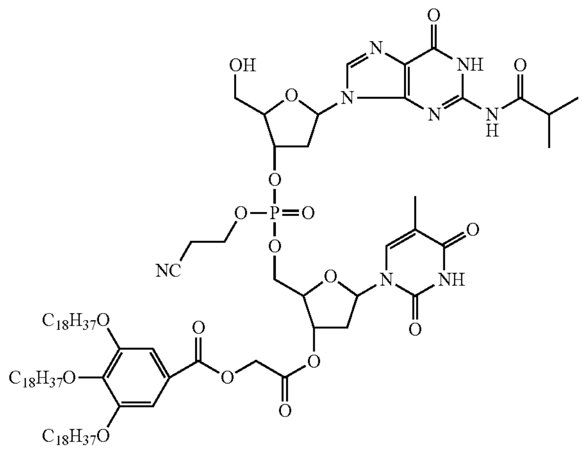

The title compound (2.43 g, 98%) was obtained from thymidine-3'-yl 2-((3,4,5-tris(octadecyloxy)benzoyl)oxy) acetate (1.82 g, 1.50 mmol) and $N^2$-isobutyryl-DMTr-dG-CE phosphoroamidite (2.52 g, 3.00 mmol) according to the methods of Examples 2-3.

$^1$H-NMR (400 MHz, $CDCl_3$): δ 0.88 (t, 9H, J=7.2 Hz), 1.00-1.41 (m, 90H), 1.41-1.54 (m, 6H), 1.71-1.85 (m, 6H), 1.92-2.00 (m, 3H), 2.24-2.97 (m, 6H), 3.68-4.08 (m, 8H), 4.14-4.54 (m, 6H), 4.78-4.92 (m, 2H), 5.14-5.78 (m, 2H), 5.95-6.24 (m, 2H), 7.27-7.43 (m, 3H), 7.87-7.95 (m, 1H), 10.19-10.49 (m, 2H), 12.24-12.38 (m, 1H).

$^{13}$C-NMR (100 MHz, $CDCl_3$): δ 12.35, 14.14, 19.01, 19.06, 19.10, 19.73, 19.80, 19.85, 22.70, 26.07, 26.14, 29.33, 29.38, 29.45, 29.61, 29.68, 29.74, 30.02, 30.36, 31.77, 31.94, 35.80, 35.92, 36.62, 38.19, 38.48, 61.05, 61.13, 62.26, 62.44, 62.49, 62.70, 62.75, 66.12, 67.37, 69.21, 73.58, 74.51, 80.47, 80.64, 82.33, 82.40, 85.33, 85.52, 86.12, 86.55, 86.84, 87.31, 108.24, 111.24, 112.18, 116.50, 116.83, 121.43, 121.59, 123.05, 123.08, 136.55, 137.73, 138.66, 138.99, 143.02, 143.06, 147.75, 147.78, 148.49, 150.42, 151.06, 152.96, 152.97, 155.23, 155.27, 164.76, 164.83, 165.92, 165.96, 167.73, 167.80, 180.26, 180.45.

TOF/MS (ESI): calcd for $C_{90}H_{149}N_8O_{18}PNa$ $[M+Na]^+$ 1684.0625, found 1684.0643.

Examples 3-14

(2) Synthesis of 5'-O-((2-Cyanoethoxy)(5'-O-((2-Cyanoethoxy)(5'-O-(4,4'-Dimethoxytrityl)Thymidine-3'-Yl)Phosphoryl)-$N^2$-Isobutyryldeoxyguanosine-3'-Yl)Phosphoryl)Thymidine-3'-Yl 2-((3,4,5-Tris(Octadecyloxy)Benzoyl)Oxy)Acetate

[Chemical Formula 65]

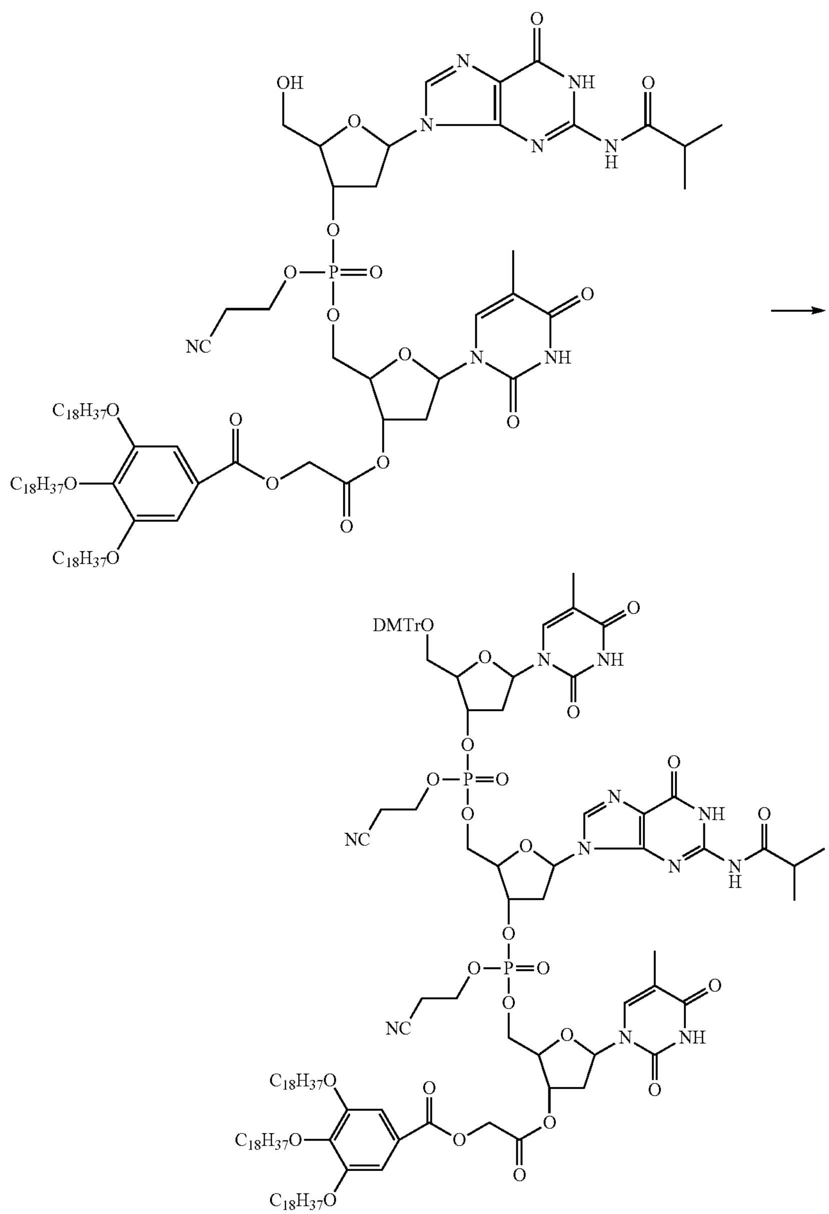

The title compound (2.76 g, 90%) was obtained from 5'-O-((2-cyanoethoxy)($N^2$-isobutyryldeoxyguanosine-3'-yl)phosphoryl)thymidine-3'-yl 2-((3,4,5-tris(octadecyloxy)benzoyl)oxy)acetate (2.20 g, 1.32 m mol) and DMTr-dT-CE-phosphoroamidite (2.96 g, 3.97 mmol) according to the methods of Examples 3-4.

$^1$H-NMR (400 MHz, $CDCl_3$): δ 0.88 (t, 9H, J=6.8 Hz), 1.13-1.47 (m, 96H), 1.71-2.01 (m, 15H), 2.35-2.85 (m, 10H), 3.31-3.51 (m, 2H), 3.78 (s, 6H), 3.96-4.04 (m, 6H), 4.05-4.59 (m, 10H), 4.84 (s, 2H), 5.13-5.55 (m, 3H), 6.11-6.42 (m, 3H), 6.83 (d, 4H, J=8.8 Hz), 7.16-7.37 (m, 12H), 7.45-7.55 (m, 1H), 7.72-7.80 (m, 1H), 9.23-10.39 (m, 3H), 12.15-12.21 (m, 1H).

$^{13}$C-NMR (100 MHz, $CDCl_3$): δ 11.70, 12.39, 12.45, 14.14, 18.82, 18.86, 19.04, 19.08, 19.58, 19.65, 19.74, 19.80, 22.70, 26.08, 26.15, 29.34, 29.38, 29.46, 29.61, 29.68, 29.74, 29.77, 30.37, 31.94, 35.89, 36.13, 36.52, 38.68, 55.29, 61.12, 62.74, 62.89, 63.22, 63.32, 67.12, 69.23, 73.60, 74.76, 79.03, 79.98, 82.49, 84.28, 85.14, 87.28, 108.26, 111.37, 111.49, 111.69, 111.72, 113.14, 113.34, 116.74, 116.84, 116.92, 121.89, 121.96, 123.02, 127.08, 127.31, 127.76, 127.85, 128.08, 129.13, 130.11, 134.94, 134.99, 135.03, 135.20, 135.30, 136.93, 138.26, 139.46, 143.07, 143.96, 144.04, 147.98, 148.02, 148.14, 148.23, 150.46, 150.57, 150.62, 152.97, 155.42, 158.60, 158.79, 163.79, 164.43, 164.50, 165.96, 167.79, 179.87, 179.95.

TOF/MS (ESI): calcd for $C_{124}H_{183}N_{11}O_{27}P_2Na$ $[M+Na]^+$ 2343.2658, found 2343.2693.

Examples 3-15

Synthesis of 5'-O-((2-Cyanoethoxy)(5'-O-(4,4'-Dimethoxytrityl)-Thymidine-3'-Yl)Phosphorothioyl)-Thymidine-3'-Yl 2-((3,4,5-Tris(Octadecyl Oxy)Benzoyl)Oxy)Acetate

[Chemical Formula 66]

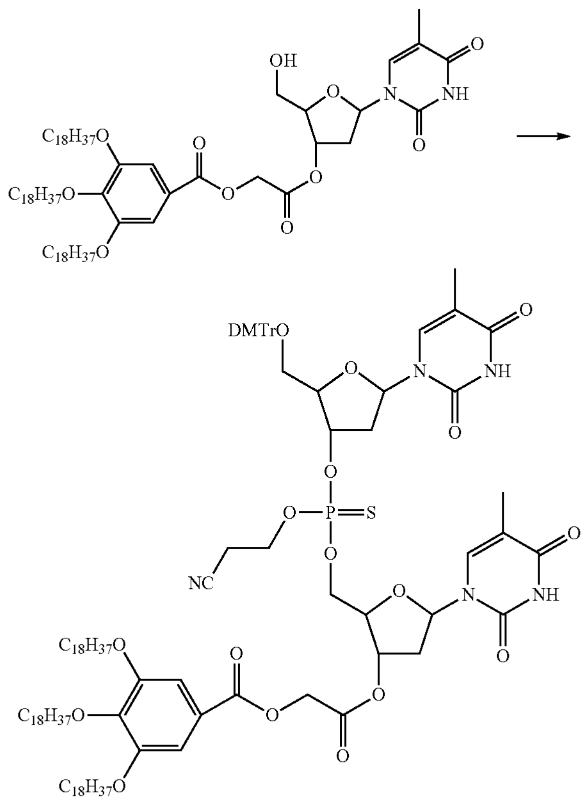

5-benzylthio-1H-tetrazole (0.58 g, 3.00 mmol) was added to a suspension of thymidine-3'-yl 2-((3,4,5-tris(octadecyloxy)benzoyl)oxy)acetate (1.82 g, 1.50 mmol) and DMTr-dT-CE phosphoroamidite (2.23 g, 3.00 mmol) in dichloromethane (27 mL), and then stirred at room temperature for 1.5 hours. Next, ((N,N-dimethylaminomethylidene)amino)-3H-1,2,4-dithiazoline-3-thione (1.13 g, 4.50 mmol) and pyridine (0.87 g, 9.00 mmol) were added, and then stirred at room temperature for 1.5 hours. The solid precipitated by dropping acetonitrile (109 mL) to the reaction solution was filtered. The solid was washed with acetonitrile-dichloromethane mixture solvent, acetonitrile, and methanol, and then dried in vacuo at 50° C. to give the title compound (2.71 g, 96%).

$^1H$-NMR (400 MHz, $CDCl_3$): δ 0.88 (t, 9H, J=6.8 Hz), 1.11-1.53 (m, 93H), 1.72-1.84 (m, 6H), 1.92-1.95 (m, 3H), 2.28-2.49 (m, 3H), 2.57-2.66 (m, 2H), 2.77 (dd, 1H, J=6.0, 7.2 Hz), 3.39-3.50 (m, 2H), 3.79 (s, 6H), 3.97-4.04 (m, 6H), 4.09-4.40 (m, 6H), 4.83 (d, 2H, J=6.8 Hz), 5.31-5.43 (m, 2H), 6.27-6.32 (m, 1H), 6.35-6.41 (m, 1H), 6.82-6.86 (m, 4H), 7.22-7.32 (m, 10H), 7.37-7.39 (m, 2H), 7.56 (s, 1H), 8.69-8.91 (m, 2H).

$^{13}C$-NMR (100 MHz, $CDCl_3$): δ 11.79, 12.58, 14.14, 19.31, 19.40, 19.47, 19.55, 22.70, 26.07, 26.13, 29.32, 29.38, 29.44, 29.60, 29.68, 29.73, 30.35, 31.94, 36.78, 39.00, 55.29, 61.06, 62.65, 62.69, 62.90, 62.94, 63.21, 67.63, 69.19, 73.56, 75.01, 75.09, 80.18, 82.27, 82.36, 84.40, 84.53, 84.91, 85.39, 87.31, 108.25, 111.74, 111.90, 113.37, 116.15, 116.39, 123.06, 127.28, 128.05, 128.11, 130.09, 134.97, 135.03, 135.06, 135.30, 143.01, 144.04, 150.22, 150.27, 150.35, 152.94, 158.78, 163.36, 163.46, 165.86, 165.88, 167.71, 167.76.

TOF/MS (ESI): calcd for $C_{107}H_{162}N_5O_{19}PSNa$ $[M+Na]^+$ 1907.1220, found 1907.1223.

4. Synthesis of $N^4$-Benzoyl-5'-O-((2-Cyanoethoxy)(5'-O-(4,4'-Dimethoxytrityl)-2'-O-Methyluridine-3'-Yl)Phosphoryl)-2'-O-Methylcytidine-3'-Yl 2-((3,4,5-Tris(Octadecyloxy)Benzoyl)Oxy)Acetate Example 4-1

(1) Synthesis of $N^4$-Benzoyl-5'-O-(4,4'-Dimethoxytrityl)-2'-O-Methylcytidine-3'-Yl 2-((3,4,5-Tris(Octadecyloxy)Benzoyl)Oxy)Acetate

[Chemical Formula 67]

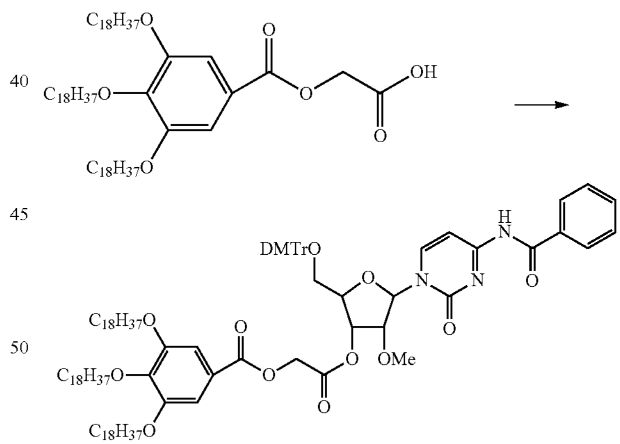

The title compound (2.96 g, 91%) was obtained from 2-((3,4,5-tris(octadecyloxy)benzoyl)oxy)acetic acid (1.97 g, 2.00 mmol) and $N^4$-benzoyl-5'-O-(4,4'-dimethoxytrityl)-2'-O-methylcytidine (1.59 g, 2.40 mmol) according to the procedure of Example 2-1.

$^1H$-NMR (400 MHz, $CDCl_3$): δ 0.88 (t, 9H, J=6.8 Hz), 1.10-1.38 (m, 84H), 1.42-1.50 (m, 6H), 1.70-1.85 (m, 6H), 3.48 (d, 1H, J=11.6 Hz), 3.62 (s, 3H), 3.69 (d, 1H, J=11.2 Hz), 3.71 (s, 1H), 3.83 (s, 5H), 3.97-4.04 (m, 6H), 4.18 (d, 1H, J=4.8 Hz), 4.36 (d, 1H, J=8.4 Hz), 4.80-4.89 (m, 2H), 5.29 (dd, 1H, J=4.8 Hz, 8.4 Hz), 6.11 (d, 1H, J=1.6 Hz), 6.90 (dd, 4H, J=2.0, 8.8 Hz), 7.27-7.42 (m, 11H), 7.52 (t, 2H,

J=7.6 Hz), 7.62 (t, 1H, J=7.6 Hz), 7.89 (d, 2H, J=7.6 Hz), 8.55 (d, 1H, J=6.4 Hz), 8.61-8.72 (brs, 1H).
$^{13}$C-NMR (100 MHz, $CDCl_3$): δ 14.14, 22.70, 26.07, 26.09, 26.11, 29.31, 29.38, 29.43, 29.59, 29.66, 29.68, 29.73, 30.34, 31.94, 52.31, 55.24, 59.15, 60.47, 60.72, 61.06, 69.14, 70.07, 73.53, 80.42, 82.21, 87.49, 88.91, 108.22, 113.43, 123.33, 123.50, 127.27, 127.49, 128.17, 129.06, 130.06, 130.08, 133.17, 135.07, 135.22, 142.85, 143.86, 152.87, 152.90, 158.75, 165.64, 165.84, 167.17, 168.42.
TOF/MS (ESI): calcd for $C_{101}H_{151}N_3O_{14}Na$ $[M+Na]^+$ 1653.1094, found 1653.1171.
Example 4-2
(2) Synthesis of N$^4$-Benzoyl-2'-O-Methylcytidine-3'-Yl 2-((3,4,5-Tris(Octadecyloxy) Benzoyl)Oxy) Acetate
[Chemical Formula 68]
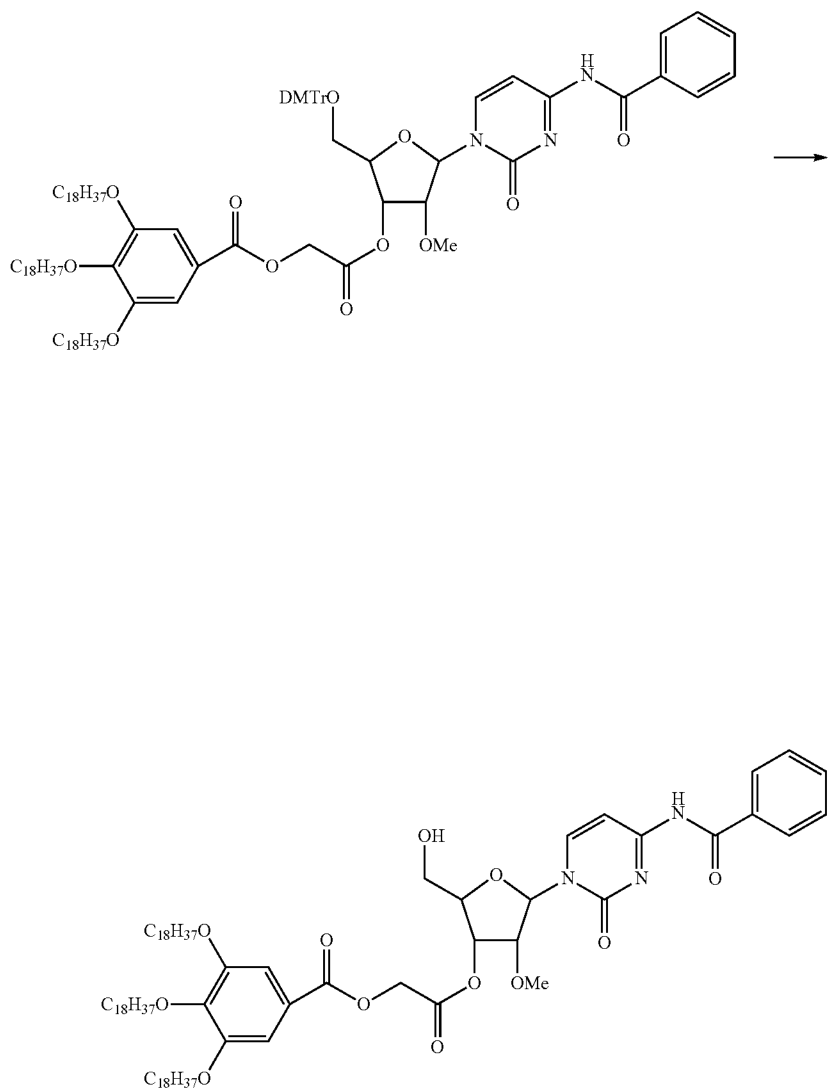

The title compound (2.26 g, 99%) was obtained from $N^4$-benzoyl-5'-O-(4,4'-dimethoxytrityl)-2'-O-methylcytidine-3'-yl 2-((3,4,5-tris (octadecyloxy)benzoyl)oxy)acetate (2.80 g, 1.72 mmol) according to the methods of Examples 2-2.

$^1$H-NMR (400 MHz, $CDCl_3$): δ 0.88 (t, 9H, J=6.8 Hz), 1.10-1.55 (m, 90H), 1.70-1.85 (m, 6H), 3.51 (s, 3H), 3.79-3.83 (m, 2H), 3.95-4.08 (m, 7H), 4.34 (d, 1H, J=4.8 Hz), 4.50 (t, 1H, J=4.8H z), 4.83-4.90 (m, 2H), 5.44 (t, 1H, J=4.8 Hz), 5.73 (d, 1H, J=4.4 Hz), 7.29-7.30 (m, 2H), 7.47-7.66 (m, 3H), 7.90 (d, 2H, J=7.6 Hz), 8.16 (d, 1H, J=7.6 Hz), 8.75-9.00 (brs, 1H).

$^{13}$C-NMR (100 MHz, $CDCl_3$): δ 14.14, 22.71, 26.07, 26.11, 29.30, 29.38, 29.42, 29.59, 29.66, 29.68, 29.73, 30.34, 31.94, 52.32, 59.19, 60.97, 61.07, 61.24, 69.15, 69.20, 71.18, 73.56, 80.58, 83.43, 92.64, 108.28, 123.20, 123.50, 127.61, 129.09, 132.80, 133.36, 142.99, 147.07, 152.87, 152.93, 162.63, 165.85, 167.66, 168.43.

TOF/MS (ESI): calcd for $C_{80}H_{133}N_3O_{12}Na$ $[M+Na]^+$ 1350.9787, found 1350.9855.

Example 4-3

(3) Synthesis of $N^4$-Benzoyl-5'-O-((2-Cyanoethoxy)(5'-O-(4,4'-Dimethoxytrityl)-2'-O-Methyluridine-3'-Yl)Phosphoryl)-2'-O-Methylcytidine-3'-Yl 2-((3,4,5-Tris(Octadecyloxy)Benzoyl)Oxy)Acetate

[Chemical Formula 69]

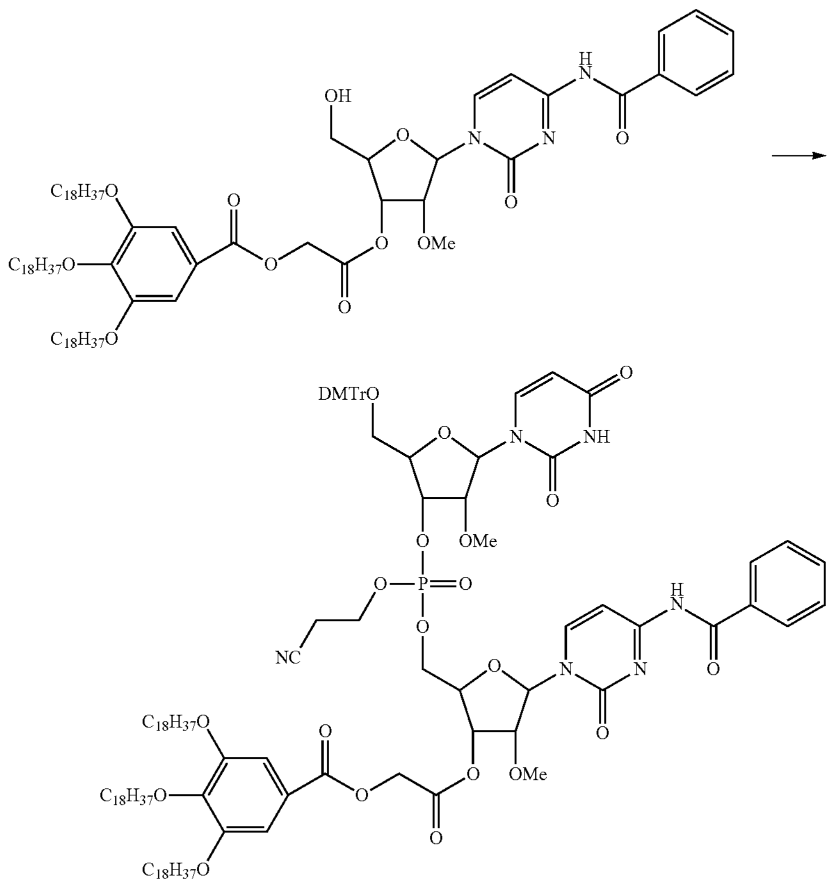

A crude compound (2.80 g) was obtained from $N^4$-benzoyl-2'-O-methylcytidine-3'-yl 2-((3,4,5-tris(octadecyloxy)benzoyl)oxy)acetate (2.10 g, 1.58 mmol) and 5'-O-DMTr-2'-O-methyluridine-CE phosphoro amidite (2.40 g, 3.16 mmol) according to the methods of Examples 3-4. The crude compound was purified by column chromatography (spherical neutral silica gel, eluent: dichloromethane—methanol) to give the title compound (2.21 g, 70%).

$^1$H-NMR (400 MHz, $CDCl_3$): δ 0.88 (t, 9H, J=6.8 Hz), 1.10-1.53 (m, 90H), 1.71-1.83 (m, 6H), 2.50-2.74 (m, 1H), 2.79 (t, 1H, J=6.4 Hz), 3.46-3.76 (m, 8H), 3.77 (s, 3H), 3.79 (s, 3H), 3.97-4.04 (m, 6H), 4.11-4.58 (m, 7H), 4.82-4.95 (m, 2H), 5.13-5.30 (m, 3H), 5.86-6.08 (m, 2H), 6.82-6.88 (m, 4H), 7.23-7.36 (m, 11H), 7.51 (t, 2H, 8.0 Hz), 7.61 (t, 1H, J=7.2 Hz), 7.82-8.05 (m, 4H), 8.69-8.96 (m, 2H).

$^{13}$C-NMR (100 MHz, $CDCl_3$): δ 14.14, 19.52, 19.58, 22.70, 26.07, 26.13, 29.33, 29.38, 29.45, 29.60, 29.68, 29.73, 30.35, 31.94, 55.25, 55.30, 58.84, 59.27, 60.82, 61.14, 62.35, 62.40, 62.68, 62.73, 65.55, 66.16, 69.19, 69.90, 70.16, 73.56, 74.28, 74.38, 79.38, 79.46, 79.52, 79.60, 81.32, 81.38, 81.52, 82.19, 86.71, 86.87, 87.46, 90.07, 90.64, 102.58, 102.62, 108.24, 113.34, 113.36, 116.36, 116.43, 123.19, 127.39, 127.44, 127.64, 128.10, 128.12, 128.26, 128.29, 129.04, 130.21, 130.27, 130.30, 133.28, 134.64, 134.73, 139.53, 139.75, 142.96, 143.82, 143.90, 150.02, 150.07, 152.93, 158.81, 158.84, 158.86, 162.70, 162.73, 165.77, 165.81, 167.22, 167.26.

TOF/MS (ESI): calcd for $C_{114}H_{167}N_6O_{22}PNa$ $[M+Na]^+$ 2026.1769, found 2026.1764.

Synthesis of 5'-O-((2-Cyanoethoxy)(5'-O-(4,4'-Dimethoxytrityl)-2'-Fluorodeoxyuridine-3'-Yl)Phosphoryl)-2'-Fluoro-$N^2$-Isobutyryldeoxyguanosine-3'-Yl 2-((3,4,5-Tris(Octadecyloxy)Benzoyl)Oxy)Acetate

Example 4-4

(1) Synthesis of 5'-O-(4,4'-Dimethoxytrityl)-2'-Fluoro-$N^2$-Isobutyryldeoxyguanosine-3'-Yl 2-((3,4,5-Tris(Octadecyloxy)Benzoyl)Oxy)Acetate

[Chemical Formula 70]

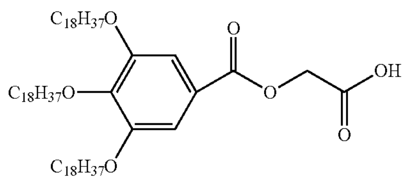

-continued

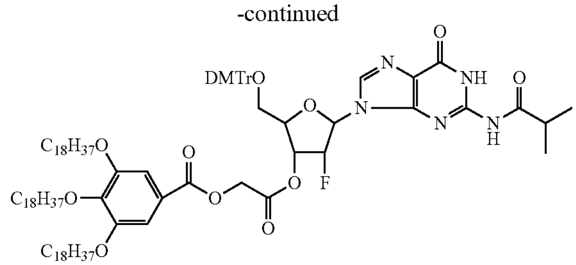

The title compound (3.13 g, 96%) was obtained from 2-((3,4,5-tris(octadecyloxy)benzoyl)oxy)acetic acid (1.97 g, 2.00 mmol) and 5'-O-(4,4'-dimethoxytrityl)-2'-fluoro-$N^2$-isobutyryldeoxyguanosine (1.58 g, 2.40 mmol) according to the procedure of Example 2-1.

$^1$H-NMR (400 MHz, $CDCl_3$): δ 0.81 (d, 3H, J=6.8 Hz), 0.88 (t, 9H, J=6.8 Hz), 0.94 (d, 3H, J=7.2 Hz), 1.10-1.53 (m, 90H), 1.70-1.87 (m, 6H), 1.93 (sept, 1H, J=6.8 Hz), 3.17 (d, 1H, J=11.2H z), 3.59 (d, 1H, J=11.2 Hz), 3.77 (s, 6H), 3.97-4.05 (m, 6H), 4.32-4.34 (m, 1H), 4.85 (d, 1H, J=16.0 Hz), 4.92 (d, 1H, J=16.0 Hz), 5.92-6.07 (m, 2H), 6.18-6.24 (m, 1H), 6.78 (dd, 4H, J=5.2, 8.8 Hz), 7.16-7.29 (m, 7H), 7.30 (s, 2H), 7.36 (d, 2H, J=8.0 Hz), 7.79 (s, 1H), 8.01 (s, 1H), 11.92 (s, 1H).

$^{13}$C-NMR (100 MHz, $CDCl_3$): δ 14.14, 18.39, 18.47, 18.88, 18.91, 22.70, 25.61, 26.06, 26.11, 29.30, 29.38, 29.42, 29.59, 29.66, 29.68, 29.73, 30.34, 31.94, 36.25, 36.43, 55.24, 55.25, 60.68, 60.84, 61.24, 67.98, 69.25, 70.85, 71.00, 73.61, 79.97, 81.44, 83.15, 86.36, 86.47, 86.67, 90.96, 108.26, 113.15, 113.22, 122.23, 123.17, 127.08, 127.13, 127.76, 127.85, 127.89, 127.98, 129.13, 129.85, 129.92, 135.20, 135.66, 138.43, 138.70, 139.43, 143.05, 144.47, 147.30, 147.34, 147.47, 147.90, 152.93, 152.96, 155.04, 155.31, 158.62, 158.69, 165.65, 165.89, 167.23, 167.60, 178.18, 178.76.

TOF/MS (ESI): calcd for $C_{98}H_{150}N_5O_{13}F$ $[M+H]^+$ 1623.1136, found 1623.1160.

Example 4-5

(2) Synthesis of 2'-Fluoro-$N^2$-Isobutyryldeoxyguanosine-3'-Yl 2-((3,4,5-Tris(Octadecyloxy)Benzoyl)Oxy)Acetate

[Chemical Formula 71]

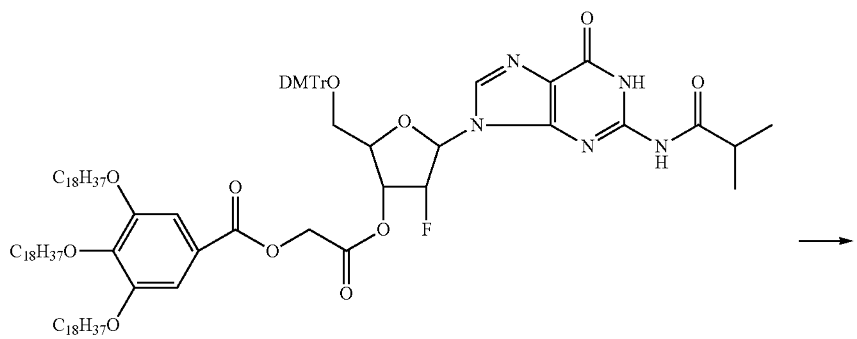

-continued

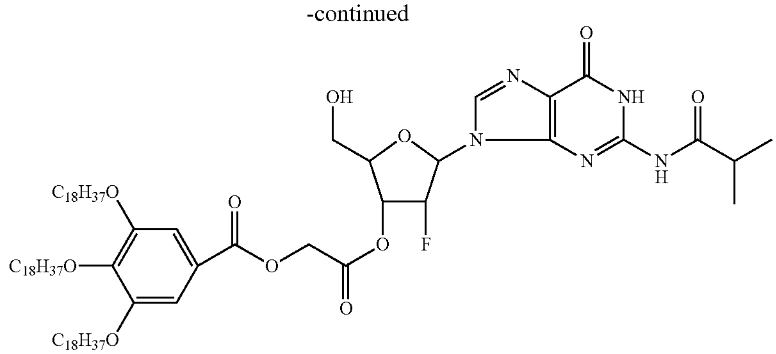

The title compound (2.40 g, 98%) was obtained from 5'-O-(4,4'-dimethoxytrityl)-2'-fluoro-$N^2$-isobutyryldeoxyguanosine-3'-yl 2-((3,4,5-tris(octadecyloxy)benzoyl)oxy) acetate (3.00 g, 1.85 mmol) according to the procedure of Example 2-2.

$^1$H-NMR (400 MHz, $CDCl_3$): δ 0.88 (t, 9H, J=6.8 Hz), 1.10-1.55 (m, 96H), 1.70-1.85 (m, 6H), 2.71 (sept, 1H, J=6.8 Hz), 3.37-3.72 (brs, 2H), 3.80 (d, 1H, J=11.6 Hz), 3.99-4.05 (m, 7H), 4.34 (d, 1H, J=4.0 Hz), 4.94 (s, 2H), 5.69 (dt, 1H, J=4.4, 52.0 Hz), 5.78-5.84 (m, 1H), 5.97 (dd, 1H, J=4.0, 16.0 Hz), 7.31 (s, 2H), 7.90 (s, 1H), 9.22 (s, 1H), 12.15 (s, 1H).

$^{13}$C-NMR (100 MHz, $CDCl_3$): δ 14.14, 18.85, 18.95, 22.70, 26.06, 26.11, 29.30, 29.38, 29.43, 29.60, 29.68, 29.74, 30.33, 31.94, 36.32, 60.86, 69.24, 71.25, 71.39, 73.60, 82.89, 87.22, 87.55, 89.60, 91.55, 108.27, 121.56, 123.15, 138.45, 142.99, 147.29, 148.08, 152.91, 155.03, 165.91, 167.26, 179.15.

TOF/MS (ESI): calcd for $C_{77}H_{132}N_5O_{11}FNa$ $[M+Na]^+$ 1344.9805, found 1344.9834.

Examples 4-6

(3) Synthesis of 5'-O-((2-Cyanoethoxy)(5'-O-(4,4'-Dimethoxytrityl)-2'-Fluorodeoxyuridine-3'-Yl)Phosphoryl)-2'-Fluoro-$N^2$-Isobutyryldeoxyguanosine-3'-Yl 2-((3,4,5-Tris(Octadecyloxy)Benzoyl)Oxy) Acetate

[Chemical Formula 72]

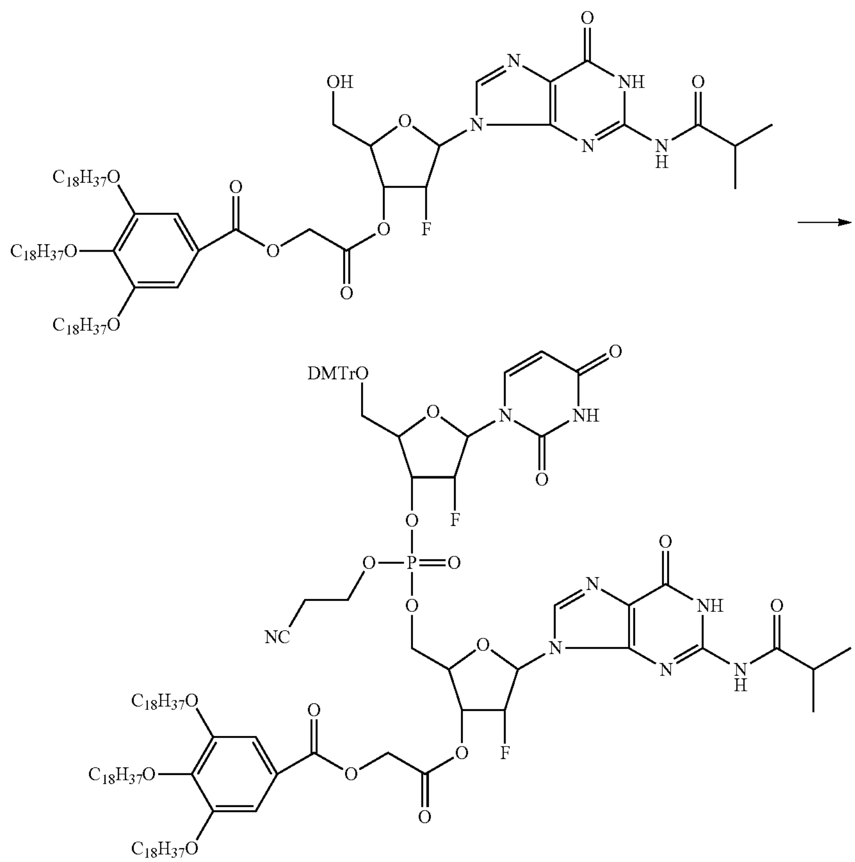

The title compound (3.07 g, 93%) was obtained from 2'-fluoro-$N^2$-isobutyryldeoxyguanosine-3'-yl 2-((3,4,5-tris (octadecyloxy)benzoyl)oxy)acetate (2.20 g, 1.66 mmol) and 5'-O-DMTr-2'-fluoro-deoxyuridine-CE phosphoroamidite (2.49 g, 3.33 mmol) according to the methods of Examples 3-4.

$^1$H-NMR (400 MHz, $CDCl_3$): 0.88 (t, 9H, J=7.2 Hz), 0.97-1.53 (m, 96H), 1.71-1.83 (m, 6H), 2.56-2.75 (m, 3H), 3.37-3.66 (m, 2H), 3.74-3.79 (m, 6H), 3.97-4.55 (m, 12H), 4.78-5.08 (m, 2H), 5.08-5.50 (m, 3H), 5.70-6.01 (m, 4H), 6.80-6.84 (m, 4H), 7.17-7.40 (m, 11H), 7.57-7.73 (m, 2H), 8.94-9.07 (m, 1H), 10.00 (s, 1H), 12.18-12.26 (m, 1H).

$\delta^{13}$C-NMR (100 MHz, $CDCl_3$): δ 14.14, 18.51, 18.76, 18.92, 19.20, 19.55, 19.62, 22.70, 26.07, 26.14, 29.33, 29.38, 29.45, 29.60, 29.68, 29.74, 30.36, 31.94, 35.90, 35.99, 55.23, 55.30, 60.70, 60.88, 62.85, 69.26, 73.61, 79.54, 79.63, 87.17, 87.21, 102.93, 108.31, 113.31, 116.34, 116.52, 122.55, 122.61, 122.95, 122.98, 127.25, 127.31, 128.07, 128.10, 130.14, 134.79, 134.88, 134.92, 138.65, 140.55, 143.15, 143.19, 143.92, 144.02, 147.71, 147.74, 148.30, 148.43, 149.68, 149.98, 152.98, 152.99, 155.30, 155.48, 158.74, 158.79, 162.67, 165.89, 166.00, 167.20, 179.68.

TOF/MS (ESI): calcd for $C_{110}H_{163}N_8O_{20}F_2PNa$ $[M+Na]^+$ 2008.1587, found 2008.1593.

Synthesis of 5'-O-((2-Cyanoethoxy)(5'-O-(4,4'-Dimethoxytrityl)-2'-O-(Tert-Butyldimethylsilyl)Uridine-3'-Yl)Phosphoryl)-2'-O-(Tert-Butyldimethylsilyl) Uridine-3'-Yl 2-((3,4,5-Tris(Octadecyloxy) Benzoyl)Oxy)Acetate

Examples 4-7

(1) Synthesis of 5'-O-(4,4'-Dimethoxytrityl)-2'-O-(Tert-Butyldimethylsilyl)Uridine-3'-Yl 2-((3,4,5-Tris (Octadecyloxy)Benzoyl)Oxy)Acetate

[Chemical Formula 73]

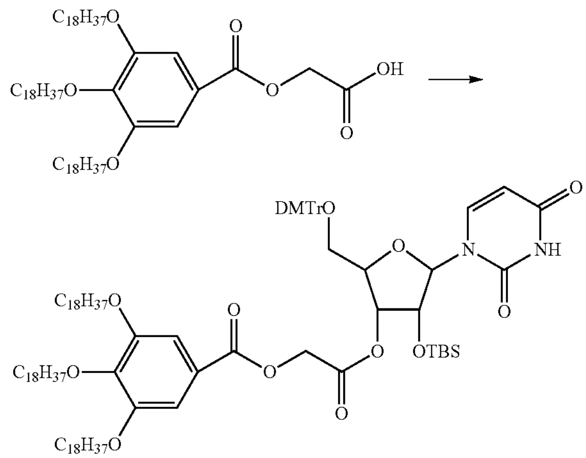

4-dimethylaminopyridine (0.03 g, 0.25 mmol) and 1-(3-dimethylaminopropyl)-3-ethylcarbodiimide hydrochloride (0.58 g, 3.00 mmol) was added to a suspension of 2-((3,4,5-tris(octadecyloxy)benzoyl)oxy) acetic acid (2.46 g, 2.50 mmol) and 5'-O-(4,4'-dimethoxytrityl)-2'-O-(tert-butyldimethylsilyl)uridine (1.98 g, 3.00 mmol) in dichloromethane (25 mL), and then stirred at room temperature for 5 hours. The solid precipitated by dropping acetonitrile (148 mL) to the reaction solution was filtered. The solid was washed with acetonitrile—dichloromethane mixture solvent, and then dried under reduced pressure at 50° C. to obtain a crude compound (2.89 g). The crude compound was purified by column chromatography (spherical neutral silica gel, eluent: dichloromethane—THF) to give the title compound (2.76 g, 68%) as a white solid.

$^1$H-NMR (400 MHz, $CDCl_3$): δ 0.08 (s, 3H), 0.11 (s, 3H), 0.81-0.92 (m, 18H), 1.04-1.53 (m, 90H), 1.70-1.84 (m, 6H), 3.49 (dd, 2H, J=10.8, 27.6 Hz), 3.79 (s, 6H), 3.79-4.04 (m, 6H), 4.26-4.27 (m, 1H), 4.56 (t, 1H, J=5.2 Hz), 4.81 (d, 1H, J=16.0 Hz), 4.96 (d, 1H, 16.4 Hz), 5.30 (d, 1H, J=8.0 Hz), 5.47 (t, 1H, J=4.0 Hz), 6.02 (d, 1H, J=5.6 Hz), 6.85 (d, 4H, J=8.4 Hz), 7.23-7.37 (m, 11H), 7.85 (d, 1H, J=8.4 Hz), 8.37 (s, 1H).

$^{13}$C-NMR (100 MHz, $CDCl_3$): δ −5.22, −5.09, 14.14, 17.87, 22.71, 25.51, 26.07, 26.11, 29.30, 29.38, 29.43, 29.59, 29.67, 29.74, 30.34, 31.94, 55.25, 60.75, 62.47, 69.14, 73.36, 73.54, 74.40, 81.20, 87.58, 88.03, 102.56, 108.25, 113.40, 113.43, 123.33, 127.33, 128.03, 128.14, 130.03, 130.17, 134.71, 134.83, 140.00, 142.87, 144.10, 150.14, 152.89, 158.78, 158.83, 162.59, 165.67, 167.10.

TOF/MS (ESI): calcd for $C_{99}H_{158}N_2O_{14}SiNa$ $[M+Na]^+$ 1650.1380, found 1650.1455.

Examples 4-8

(2) Synthesis of 2'-O-(Tert-Butyldimethylsilyl)Uridine-3'-Yl 2-((3,4,5-Tris(Octadecyloxy)Benzoyl) Oxy)Acetate

[Chemical Formula 74]

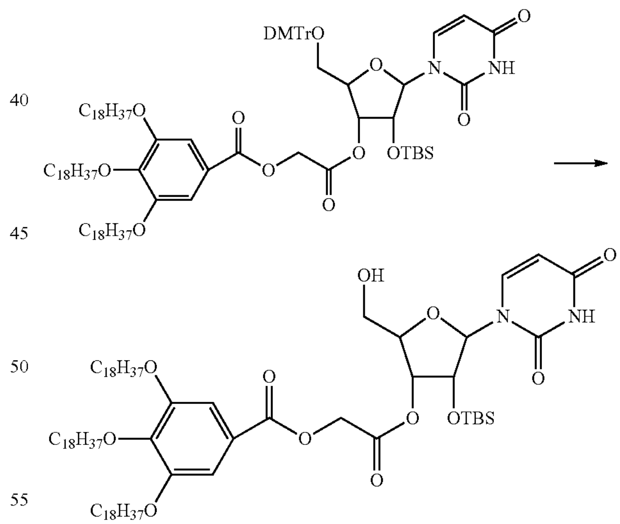

The title compound (2.05 g, 97%) was obtained from 5'-O-(4,4'-dimethoxytrityl)-2'-O-(tert-butyldimethylsilyl) uridine-3'-yl 2-((3,4,5-tris (octadecyloxy)benzoyl)oxy)acetate (2.60 g, 1.60 mmol) according to the procedure of Example 2-2.

$^1$H-NMR (400 MHz, $CDCl_3$): δ 0.04 (s, 3H), 0.07 (s, 3H), 0.81-0.92 (m, 18H), 1.11-1.53 (m, 90H), 1.70-1.85 (m, 6H), 2.95-3.10 (brs, 1H), 3.77-3.82 (m, 1H), 3.93-4.04 (m, 7H), 4.25-4.28 (m, 1H), 4.67 (t, 1H, J=5.2 Hz), 4.81 (d, 1H, 16.0 Hz), 4.96 (d, 1H, 16.0 Hz), 5.34 (dd, 1H, J=3.2, 4.8 Hz), 5.60

(d, 1H, J=5.6 Hz), 5.76 (d, 1H, J=8.0 Hz), 7.29 (s, 2H), 7.63 (d, 1H, J=8.0 Hz), 8.71 (s, 1H).

$^{13}$C-NMR (100 MHz, $CDCl_3$): δ −5.22, −5.19, 14.14, 17.88, 22.71, 25.52, 26.07, 26.10, 29.30, 29.38, 29.42, 29.59, 29.66, 29.68, 29.73, 30.34, 31.94, 60.84, 61.84, 69.20, 72.78, 73.24, 73.57, 82.99, 92.46, 102.70, 108.32, 123.24, 141.88, 142.99, 150.17, 152.92, 162.72, 1 65.78, 167.38.

TOF/MS (ESI): calcd for $C_{78}H_{140}N_2O_{12}SiNa$ [M+Na]$^+$ 1348.0073, found 1348.0115.

Examples 4-9

(3) Synthesis of 5'-O-((2-Cyanoethoxy)(5'-O-(4,4'-Dimethoxytrityl)-2'-O-(Tert-Butyldimethylsilyl)Uridine-3'-Yl)Phosphoryl)-2'-O-(Tert-Butyldimethylsilyl) Uridine-3'-Yl 2-((3,4,5-Tris(Octadecyloxy) Benzoyl)Oxy)Acetate

[Chemical Formula 75]

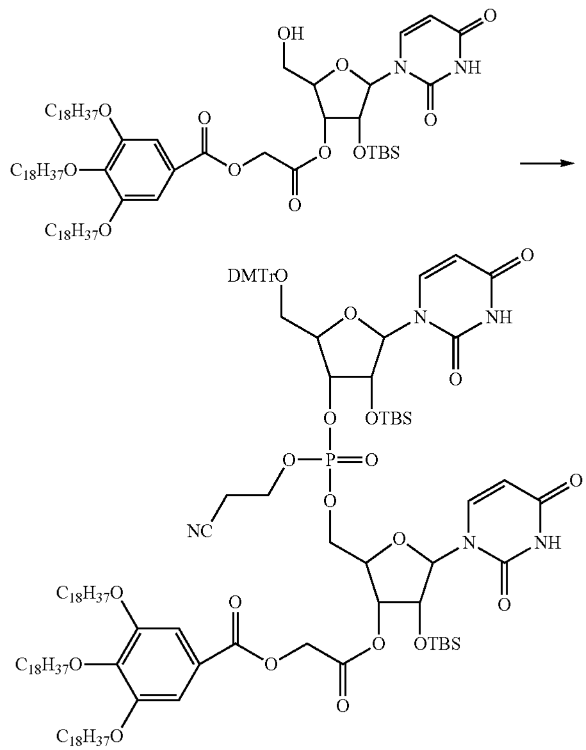

The title compound (2.84 g, 92%) was obtained from 2'-O-(tert-butyldimethylsilyl) uridine-3'-yl 2-((3,4,5-tris(octadecyloxy)benzoyl)oxy)acetate (1.95 g, 1.47 mmol) and 5'-O-DMTr-2'-O-(tert-butyldimethylsilyl) uridine-CE phosphoroamidite (2.53 g, 2.94 mmol) according to the methods of Examples 3-4.

$^1$H-NMR (400 MHz, $CDCl_3$): δ 0.03-0.13 (m, 12H), 0.86-0.90 (m, 27H), 1.02-1.53 (m, 90H), 1.68-1.84 (m, 6H), 2.45-2.69 (m, 1H), 2.73 (t, 1H, J=6.0 Hz), 3.48 (d, 1H, J=10.8 Hz), 3.60-3.68 (m, 1H), 3.76-3.84 (m, 6H), 3.97-4.04 (m, 6H), 4.10-4.58 (m, 8H), 4.73-4.84 (m, 1H), 4.90-5.03 (m, 2H), 5.20-5.25 (m, 2H), 5.67-5.78 (m, 2H), 5.95-6.03 (m, 1H), 6.80-6.89 (m, 4H), 7.21-7.44 (m, 12H), 7.84 (d, 1H, J=8.0 Hz), 8.72-8.83 (m, 2H).

$^{13}$C-NMR (100 MHz, $CDCl_3$): δ −5.27, −5.24, −5.07, −4.94, −4.92, 14.14, 17.86, 18.06, 19.50, 19.57, 19.65, 22.70, 25.50, 25.55, 25.60, 26.07, 26.13, 29.32, 29.38, 29.44, 29.60, 29.68, 29.74, 30.35, 31.94, 55.27, 55.30, 60.69, 61.96, 62.37, 62.42, 62.58, 62.63, 69.19, 71.39, 71.60, 72.86, 73.00, 73.57, 74.47, 79.43, 79.51, 81.75, 87.65, 87.68, 87.99, 88.18, 90.56, 91.22, 102.54, 102.64, 103.05, 103.13, 108.28, 113.39, 116.31, 116.40, 123.21, 127.43, 128.13, 128.21, 128.25, 130.25, 130.27, 130.32, 134.56, 134.65, 134.70, 134.73, 139.84, 140.05, 140.15, 142.97, 143.01, 143.92, 143.97, 149.95, 150.19, 150.40, 152.92, 158.83, 158.87, 162.53, 162.58, 162.69, 165.64, 165.68, 167.05, 167.12.

TOF/MS (ESI): calcd for $C_{117}H_{186}N_5O_{22}Si_2PNa$ [M+Na]$^+$ 2123.2763, found 2123.2769.

5. Synthesis of 3-((3,4,5-Tris(Octadecyloxy)Benzoyl)Oxy)Propionic Acid

Example 5-1

(1) Synthesis of Tert-Butyl 3-((3,4,5-Tris(Octadecyloxy)Benzoyl)Oxy) Propionate

[Chemical Formula 76]

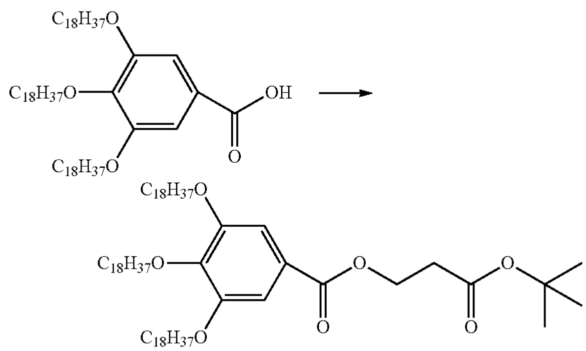

1-(3-Dimethylaminopropyl)-3-ethylcarbodiimide hydrochloride (0.86 g, 4.5 mmol) was added to a suspension of 3,4,5-tris(octadecyloxy)benzoic acid (2.78 g, 3.0 mmol), 4-dimethylaminopyridine (0.04 g, 0.3 mmol), tert-butyl 3-hydroxypropionate (4.39 g, 30.0 mmol), and triethylamine (0.46 g, 4.5 mmol) in dichloromethane (60 mL), and then stirred at room temperature for 20 hours. The solid precipitated by dropping acetonitrile (180 mL) to the reaction solution was filtered. The solid was washed with acetonitrile—dichloromethane mixture solvent, and then dried under reduced pressure at 50° C. to obtain a crude compound (3.07 g). The crude compound was purified by column chromatography (spherical neutral silica gel, eluent: dichloromethane) to afford the title compound (1.90 g, 60%) as a white solid.

$^1$H-NMR (400 MHz, $CDCl_3$): δ 0.88 (t, 9H, J=7.0 Hz), 1.15-1.55 (m, 99H), 1.70-1.85 (m, 6H), 2.68 (t, 2H, J=6.4 Hz), 3.95-4.05 (m, 6H), 4.53 (t, 2H, J=6.4 Hz), 7.23 (s, 2H). $^{13}$C-NMR (100 MHz, $CDCl_3$): δ 14.08, 22.68, 26.08, 28.09, 29.35, 29.40, 29.57, 29.65, 29.71, 30.35, 31.93, 35.42, 60.72, 69.25, 73.51, 80.97, 108.19, 124.57, 152.84, 166.14, 169.93.

TOF/MS (ESI): calcd for $C_{68}H_{126}O_7Na$ [M+Na]$^+$ 1077.9401, found 1077.9427.

Example 5-2

(2) Synthesis of 3-((3,4,5-Tris(Octadecyloxy)Benzoyl)Oxy)Propionic Acid

[Chemical Formula 77]

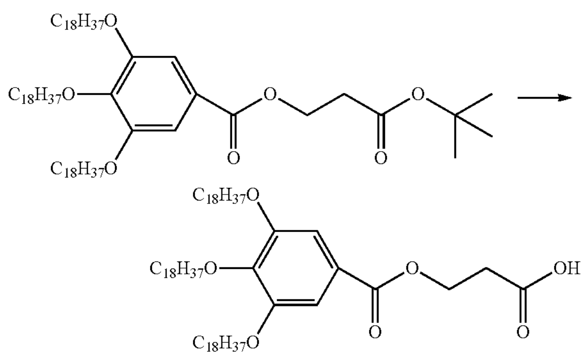

Methanesulfonic acid (3.75 g, 39.0 mmol) was added to a solution of tert-butyl 3-((3,4,5-tris(octadecyloxy)benzoyl)oxy)propionate (2.75 g, 2.6 mmol) in dichloromethane (52 mL), and then stirred at room temperature for 20 hours. The solid precipitated by dropping acetonitrile (156 mL) to the reaction solution was filtered. The solid was washed with acetonitrile—dichloromethane mixture solvent and acetonitrile, and then dried in vacuo at 50° C. to give the title compound (2.54 g, 98%) as a white solid.

$^1$H-NMR (400 MHz, $CDCl_3$): δ 0.88 (t, 9H, J=7.0 Hz), 1.15-1.55 (m, 90H), 1.70-1.85 (m, 6H), 2.85 (t, 2H, J=6.6 Hz), 3.95-4.10 (m, 6H), 4.57 (t, 2H, J=6.4 Hz), 7.23 (s, 2H).

$^{13}$C-NMR (100 MHz, $CDCl_3$): δ 14.10, 22.71, 26.10, 26.13, 29.38, 29.45, 29.61, 29.68, 29.75, 30.38, 31.96, 33.54, 59.99, 69.34, 73.57, 108.35, 124.32, 142.88, 152.91, 166.17.

TOF/MS (ESI): calcd for $C_{64}H_{118}O_7Na$ $[M+Na]^+$ 1021.8775, found 1021.8817.

Synthesis of 2-(N-Methyl-3,4,5-Tris(Octadecyloxy) Benzamide)Acetic Acid

Example 5-3

(1) Synthesis of Tert-Butyl 2-(N-Methyl-3,4,5-Tris (Octadecyloxy)Benzamido)Acetate

[Chemical Formula 78]

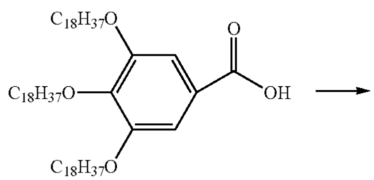

-continued

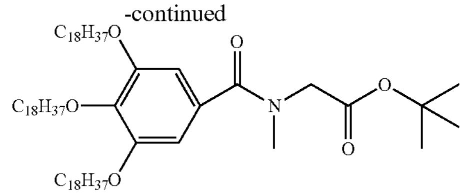

1-(3-dimethylaminopropyl)-3-ethylcarbodiimide hydrochloride (0.86 g, 4.5 mmol) was added to a suspension of 3,4,5-tris(octadecyloxy)benzoic acid (2.78 g, 3.0 mmol), 4-dimethylaminopyridine (0.04 g, 0.3 mmol), tert-butyl sarcosinate hydrochloride (2.73 g, 15.0 mmol), and triethylamine (1.52 g, 15.0 mmol) in dichloromethane (60 mL), and then stirred at room temperature for 20 hours. The solid precipitated by dropping acetonitrile (180 mL) to the reaction solution was filtered. The solid was washed with acetonitrile—dichloromethane mixture solvent, and then dried under reduced pressure at 50° C. to obtain a crude compound (3.07 g). The crude compound was purified by column chromatography (spherical neutral silica gel, eluent: dichloromethane—THF) to give the title compound (2.66 g, 84%) as a white solid.

$^1$H-NMR (400 MHz, $CDCl_3$): δ 0.88 (t, 9H, J=7.0 Hz), 1.15-1.55 (m, 99H), 1.70-1.85 (m, 6H), 3.04 (s, 3H), 3.80-4.20 (m, 8H), 6.63 (s, 2H).

$^{13}$C-NMR (100 MHz, $CDCl_3$): δ 14.01, 22.66, 26.13, 26.15, 28.16, 29.35, 29.42, 29.48, 29.65, 29.71, 30.39, 31.93, 69.51, 73.52, 82.02, 106.19, 130.61, 139.93, 153.25, 168.33, 172.01.

TOF/MS (ESI): calcd for $C_{68}H_{127}NO_6Na$ $[M+Na]^+$ 1076.9561, found 1076.9591.

Example 5-4

(2) Synthesis of 2-(N-Methyl-3,4,5-Tris(Octadecyloxy)Benzamide) Acetic Acid

[Chemical Formula 79]

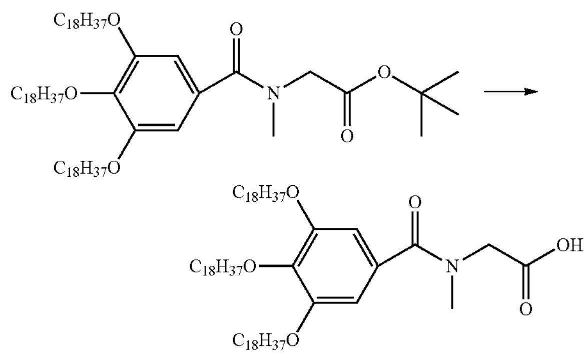

The title compound (2.38 g, 99%) was obtained from tert-butyl 2-(N-methyl-3,4,5-tris(octadecyloxy)benzamido) acetate (2.53 g, 2.4 mmol) as white solids according to the procedure of Examples 5-2.

$^1$H-NMR (400 MHz, $CDCl_3$): δ 0.88 (t, 9H, J=7.0 Hz), 1.15-1.55 (m, 90H), 1.70-1.85 (m, 6H), 3.11 (s, 3H), 3.85-4.35 (m, 8H), 6.15-6.30 (brs, 1H), 6.66 (s, 2H).

$^{13}$C-NMR (100 MHz, $CDCl_3$): δ 14.05, 22.67, 26.12, 29.36, 29.43, 29.61, 29.66, 29.72, 29.98, 30.36, 31.93, 39.20, 50.02, 69.49, 73.56, 106.47, 129.16, 140.27, 152.97, 153.24, 172.11, 172.92.

TOF/MS (ESI): calcd for $C_{64}H_{118}NO_6$ $[M-H]^-$ 996.8959, found 996.8947.

Synthesis of 3-(3,4,5-Tris(Octadecyloxy)Benzamide)Propionic Acid

Example 5-5

(1) Synthesis of Tert-Butyl 3-(3,4,5-Tris(Octadecyloxy)Benzamide) Propionate

[Chemical Formula 80]

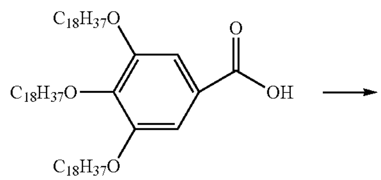

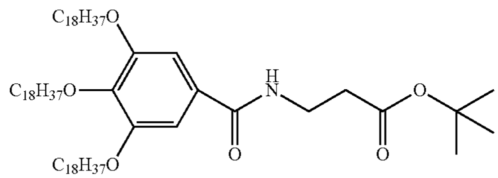

1-(3-Dimethylaminopropyl)-3-ethylcarbodiimide hydrochloride (0.86 g, 4.5 mmol) was added to a suspension of 3,4,5-tris(octadecyloxy)benzoic acid (2.78 g, 3.0 mmol), 4-dimethylaminopyridine (0.04 g, 0.3 mmol), R-alanine tert-butyl ester hydrochloride (2.73 g, 15.0 mmol), and triethylamine (1.52 g, 15.0 mmol) in dichloromethane (60 mL), and then stirred at room temperature for 19.5 hours. The solid precipitated by dropping acetonitrile (180 mL) to the reaction solution was filtered. The solid was washed with acetonitrile—dichloromethane mixture solvent, and then dried under reduced pressure at 50° C. to obtain a crude compound (3.12 g). The crude compound was purified by column chromatography (spherical neutral silica gel, eluent: dichloromethane—THF) to give the title compound (2.75 g, 87%) as a white solid.

$^1$H-NMR (400 MHz, $CDCl_3$): δ 0.88 (t, 9H, J=7.0 Hz), 1.15-1.55 (m, 99H), 1.70-1.85 (m, 6H), 2.55 (t, 2H, J=5.8 Hz), 3.66 (q, 2H, J=6.0 Hz), 3.95-4.05 (m, 6H), 6.72 (t, 1H, J=6.0 Hz), 6.94 (s, 2H).

$^{13}$C-NMR (100 MHz, $CDCl_3$): δ 14.09, 22.71, 26.11, 28.16, 29.38, 29.43, 29.61, 29.68, 29.74, 30.36, 31.95, 35.18, 35.58, 69.45, 73.53, 81.19, 105.86, 129.57, 141.32, 153.14, 167.20, 172.27.

TOF/MS (ESI): calcd for $C_{68}H_{127}NO_6Na$ $[M+Na]^+$ 1076.9561, found 1076.9579.

Example 5-6

(2) Synthesis of 3-(3,4,5-Tris(Octadecyloxy)Benzamide)Propionic Acid

[Chemical Formula 81]

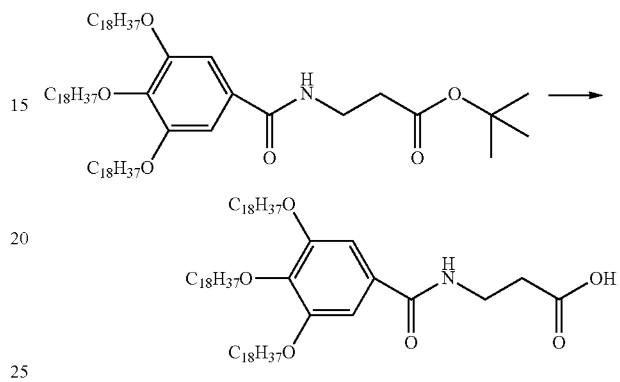

The title compound (2.52 g, 101%) was obtained from tert-butyl 3-(3,4,5-tris(octadecyloxy)benzamido)propionate (2.64 g, 2.5 mmol) as white solids according to the procedure of Examples 5-2.

$^1$H-NMR (400 MHz, $CDCl_3$): δ 0.88 (t, 9H, J=7.0 Hz), 1.15-1.55 (m, 90H), 1.65-1.85 (m, 6H), 2.74 (t, 2H, J=5.8 Hz), 3.72 (t, 2H, J=5.8 Hz), 3.90-4.05 (m, 6H), 6.95 (s, 2H).

$^{13}$C-NMR (100 MHz, $CDCl_3$): δ 14.06, 22.71, 26.16, 26.19, 29.40, 29.50, 29.53, 29.65, 29.71, 29.77, 30.44, 31.98, 33.68, 35.85, 39.37, 69.77, 73.67, 106.51, 128.33, 142.29, 153.35, 168.43, 175.46.

TOF/MS (ESI): calcd for $C_{64}H_{118}NO_6$ $[M-H]^-$ 996.8959, found 996.8912.

Synthesis of 5'-O-((2-Cyanoethoxy)(5'-O-(4,4'-Dimethoxytrityl)Thymidine-3'-Yl)Phosphoryl)Thymidine-3'-Yl 3-((3,4,5-Tris(Octadecyloxy)Benzoyl) Oxy)Propionate Examples 5-7

(1) Synthesis of Thymidine-3'-Yl 3-((3,4,5-Tris(Octadecyloxy)Benzoyl)Oxy)Propionate

[Chemical Formula 82]

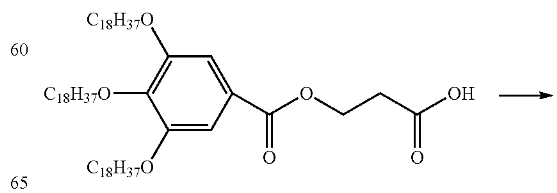

-continued

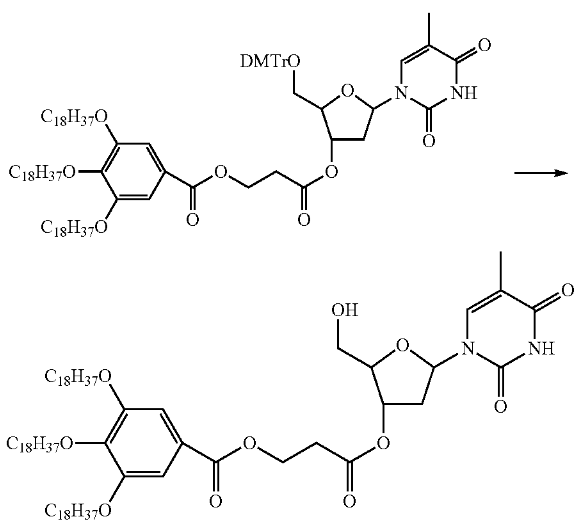

COMU (2.06 g, 4.80 mmol) was added to a suspension of 3-((3,4,5-tris(octadecyloxy)benzoyl)oxy)propionic acid (2.40 g, 2.40 mmol), 5'-O-(4,4'-dimethoxytrityl)thymidine (1.57 g, 2.88 mmol), and 1-methylimidazole (0.99 g, 12.00 mmol) in THF (24 mL), and then stirred at room temperature for 6.5 hours. Further, COMU (0.21 g, 0.48 mmol) was added, and then stirred at room temperature for 17.5 hours. The solid precipitated by dropping acetonitrile (120 mL) to the reaction solution was filtered. The solid was washed with acetonitrile—THF mixture solvent, and then dried under reduced pressure at 50° C. to obtain a crude compound (2.76 g). The crude compound was used for the next reaction without purification.

Pyrrole (0.57 g, 8.50 mmol) and trifluoroacetic acid (0.24 g, 2.13 mmol) were added to a dichloromethane solution (68 mL) of the crude compound (2.60 g), and then stirred at room temperature for 3.5 hours. Further, trifluoroacetic acid (0.05 g, 0.43 mmol) was added, and then stirred at room temperature for 1.5 hours. The solid precipitated by dropping acetone (20 mL) and acetonitrile (61 mL) to the reaction solution was filtered. The solid was washed with acetonitrile-acetone-dichloromethane mixture solvent and acetonitrile, and then dried under reduced pressure at 50° C. to obtain a crude compound (2.44 g). The crude compound was purified by column chromatography (spherical neutral silica gel, eluent: dichloromethane—THF) to give the title compound (0.52 g, 18%) as a white solid.

$^{1}$H-NMR (400 MHz, $CDCl_3$): δ 0.88 (t, 9H, J=6.8 Hz), 1.15-1.55 (m, 90H), 1.65-1.85 (m, 7H), 1.92 (s, 3H), 2.30-2.40 (m, 1H), 2.45-2.55 (m, 1H), 2.60-2.70 (m, 1H), 2.80-2.90 (m, 2H), 3.85-3.95 (m, 2H), 3.95-4.05 (m, 6H), 4.05-4.10 (m, 1H), 4.55-0.65 (m, 2H), 5.40-5.55 (m, 1H), 6.10-6.20 (m, 1H), 7.22 (s, 2H), 7.41 (s, 1H), 8.58-8.64 (m, 1H).

$^{13}$C-NMR (100 MHz, $CDCl_3$): δ 12.57, 14.14, 22.71, 26.07, 26.11, 29.33, 29.38, 29.43, 29.59, 29.67, 29.74, 30.02, 30.34, 31.94, 34.16, 36.90, 60.05, 62.58, 69.24, 73.54, 75.25, 85.10, 86.67, 108.06, 111.42, 124.14, 136.56, 142.69, 150.26, 152.87, 163.40, 166.10, 170.43.

TOF/MS (ESI): calcd for $C_{74}H_{130}N_2O_{11}Na$ $[M+Na]^+$ 1245.9572, found 1245.9548.

Example 5-8

(2) Synthesis of 5'-O-((2-Cyanoethoxy)(5'-O-(4,4'-Dimethoxytrityl) Thymidine-3'-Yl)Phosphoryl)Thymidine-3'-Yl 3-((3,4,5-Tris(Octadecyloxy)Benzoyl) Oxy)Propionate

[Chemical Formula 83]

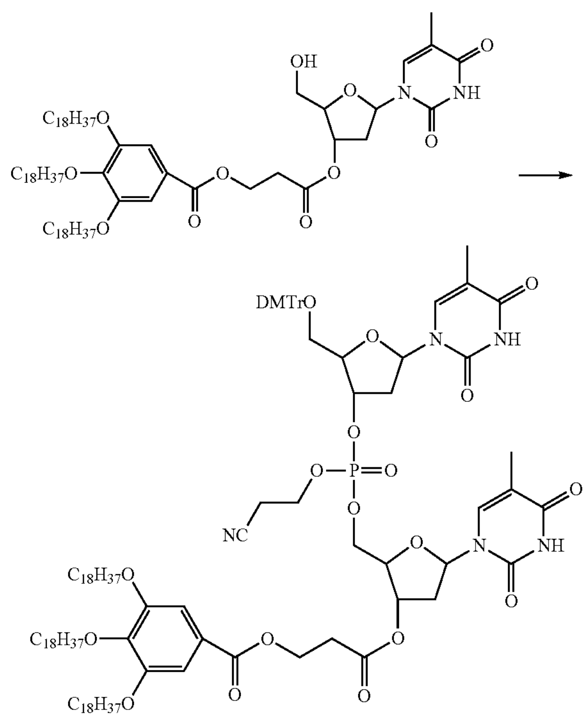

The title compound (2.22 g, 96%) was obtained as a white solid from thymidine-3'-yl 3-((3,4,5-tris((octadecyloxy)benzoyl)oxy)propionate (1.50 g, 1.23 mmol) and DMTr-dT-CE phosphoroamidite (1.83 g, 2.45 mmol) according to the methods of Examples 3-4.

$^{1}$H-NMR (400 MHz, $CDCl_3$): δ 0.88 (t, 9H, J=6.8 Hz), 1.10-1.38 (m, 84H), 1.41-1.50 (m, 9H), 1.70-1.83 (m, 7H), 1.91 (s, 3H), 2.30-2.46 (m, 3H), 2.62-2.68 (m, 2H), 2.75 (t, 1H, J=6.0 Hz), 2.84 (dd, 2H, J=4.8, 6.4 Hz), 3.37-3.42 (m, 1H), 3.50-3.55 (m, 1H), 3.79 (s, 6H), 3.98-4.02 (m, 6H), 4.12-4.38 (m, 6H), 4.56 (dd, 2H, J=4.8, 7.2 Hz), 5.16-5.20 (m, 1H), 5.28-5.35 (m, 1H), 6.21-6.26 (m, 1H), 6.38-6.44 (m, 1H), 6.84 (d, 4H, J=7.6 Hz), 7.21-7.32 (m, 10H), 7.34-7.37 (m, 2H), 7.50-7.59 (m, 1H), 8.91-9.06 (m, 2H).

$^{13}$C-NMR (100 MHz, $CDCl_3$): δ 11.72, 12.46, 14.13, 19.59, 19.66, 19.75, 22.70, 26.08, 26.15, 29.37, 29.46, 29.61, 29.67, 29.74, 30.36, 31.94, 33.94, 36.62, 38.95, 55.29, 59.89, 59.93, 62.39, 62.45, 62.54, 62.59, 63.23, 67.62, 69.27, 73.55, 74.09, 79.77, 79.82, 79.87, 79.92, 82.52, 84.29, 84.34, 84.46, 84.53, 85.36, 85.57, 87.34, 108.14, 111.70, 111.82, 113.36, 116.17, 116.36, 124.17, 127.34, 128.08, 128.14, 130.13, 134.94, 135.03, 135.07, 135.35, 135.49, 142.74, 143.97, 143.99, 150.23, 150.27, 150.38, 150.46, 152.89, 158.84, 163.40, 163.50, 166.14, 170.29, 170.34.

TOF/MS (ESI): calcd for $C_{108}H_{164}N_5O_{20}PNa$ $[M+Na]^+$ 1905.1605, found 1905.1636.

Synthesis of 5'-O-((2-Cyanoethoxy)(5'-O-(4,4'-Dimethoxytrityl)Thymidine-3'-Yl)Phosphoryl)Thymidine-3'-Yl 2-(N-Methyl-3,4,5-Tris(Octadecyloxy) Benzamide)Acetate Examples 5-9

(1) Synthesis of 5'-O-(4,4'-Dimethoxytrityl)Thymidine-3'-Yl 2-(N-Methyl-3,4,5-Tris(Octadecyloxy) Benzamide)Acetate

[Chemical Formula 84]

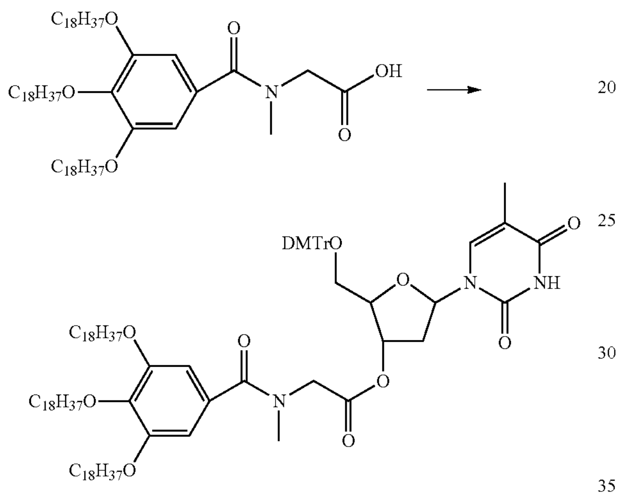

COMU (1.80 g, 4.20 mmol) was added to a suspension of 2-(N-methyl 3,4,5-tris(octadecyloxy)benzamide)acetic acid (2.10 g, 2.10 m mol), 5'-O-(4,4'-dimethoxytrityl)thymidine (1.37 g, 2.52 mmol) and 1-methylimidazole (0.86 g, 10.50 mmol) in THF (32 mL), and stirred at room temperature for 3.5 hours. Further, COMU (0.27 g, 0.63 mmol) was added, and then stirred at room temperature for 20 hours. The solid precipitated by dropping acetonitrile (158 mL) to the reaction solution was filtered. The solid was washed with acetonitrile—THF mixture solvent, and then dried under reduced pressure at 50° C. to obtain a crude compound (2.96 g). The crude compound was purified by column chromatography (spherical neutral silica gel, eluent: dichloro methane—THF) to give the title compound (2.51 g, 78%) as a white solid.

$^{1}$H-NMR (400 MHz, $CDCl_3$): δ 0.88 (t, 9H, J=6.8 Hz), 1.15-1.55 (m, 93H), 1.65-1.90 (m, 6H), 2.35-2.60 (m, 2H), 3.08 (s, 3H), 3.45-3.55 (m, 2H), 3.79 (s, 6H), 3.85-4.00 (m, 6H), 4.10-4.40 (m, 3H), 5.50-5.60 (m, 1H), 6.40-6.50 (m, 1H), 6.65 (s, 2H), 6.80-6.90 (m, 4H), 7.20-7.40 (m, 9H), 7.62 (s, 1H), 8.36 (s, 1H).

$^{13}$C-NMR (100 MHz, $CDCl_3$): δ 11.64, 14.07, 22.71, 26.17, 29.38, 29.48, 29.65, 29.70, 29.75, 30.41, 31.97, 38.01, 55.30, 63.79, 69.54, 73.58, 76.72, 84.09, 84.54, 87.42, 106.36, 111.64, 113.49, 127.31, 128.09, 128.26, 129.90, 130.15, 135.30, 135.38, 140.18, 144.29, 150.20, 153.29, 159.01, 163.21, 168.70, 172.20.

TOF/MS (ESI): calcd for $C_{95}H_{149}N_3O_{12}Na$ $[M+Na]^+$ 1547.1039, found 1547.1042.

Example 5-10

(2) Synthesis of Thymidine-3'-Yl 2-(N-Methyl-3,4,5-Tris(Octadecyloxy)Benzamide)Acetate

[Chemical Formula 85]

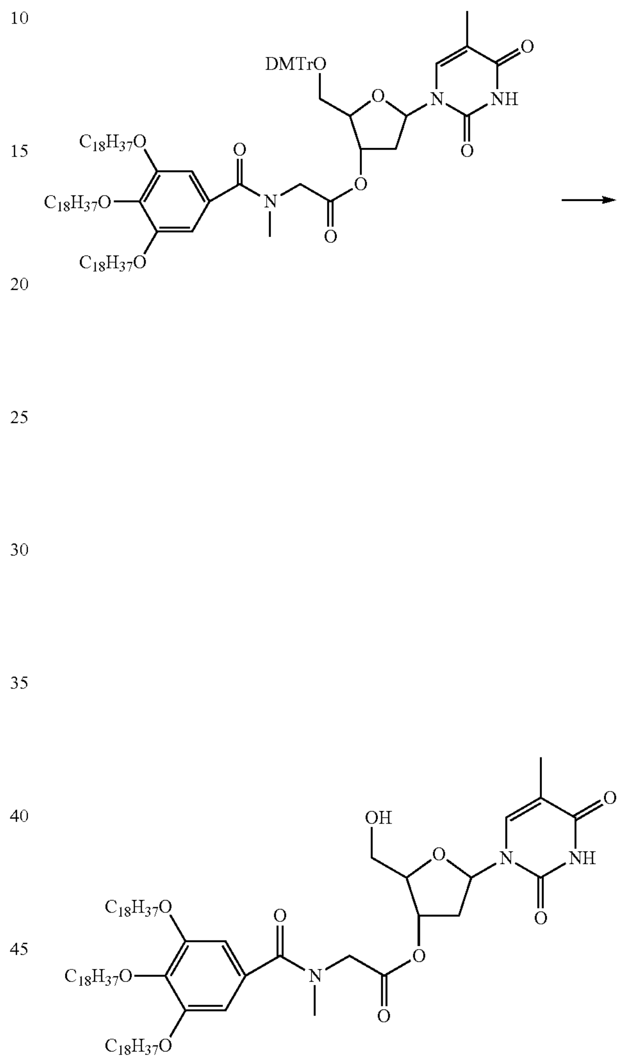

The title compound (1.86 g, 98%) was obtained as a white solid from 5'-O-(4,4'-dimethoxytrityl)thymidine-3'-yl 2-(N-methyl-3,4,5-tris (octadecyloxy)benzamide)acetate (2.36 g, 1.55 mmol) according to the method of Example 2-2.

$^{1}$H-NMR (400 MHz, $CDCl_3$): δ 0.88 (t, 9H, J=6.8 Hz), 1.05-1.55 (m, 90H), 1.65-1.85 (m, 6H), 1.92 (s, 3H), 2.30-2.60 (m, 3H), 3.09 (s, 3H), 3.85-4.05 (m, 8H), 4.05-4.35 (m, 3H), 5.45 (s, 1H), 6.05-6.30 (brs, 1H), 6.64 (s, 2H), 7.44 (s, 1H), 8.28 (s, 1H).

$^{13}$C-NMR (100 MHz, $CDCl_3$): δ 12.50, 14.08, 22.71, 26.17, 29.38, 29.47, 29.51, 29.65, 29.70, 29.75, 30.41, 31.97, 37.20, 39.06, 62.67, 69.59, 73.60, 75.74, 85.09, 86.62, 106.33, 111.45, 129.86, 136.38, 140.23, 150.26, 153.33, 163.22, 168.96, 172.29.

TOF/MS (ESI): calcd for $C_{74}H_{131}N_3O_{10}Na$ $[M+Na]^+$ 1244.9732, found 1244.9786.

Example 5-11

(3) Synthesis of 5'-O-((2-Cyanoethoxy)(5'-O-(4,4'-Dimethoxytrityl) Thymidine-3'-Yl)Phosphoryl)Thymidine-3'-Yl 2-(N-Methyl-3,4,5-Tris(Octadecyloxy) Benzamide)Acetate

[Chemical Formula 86]

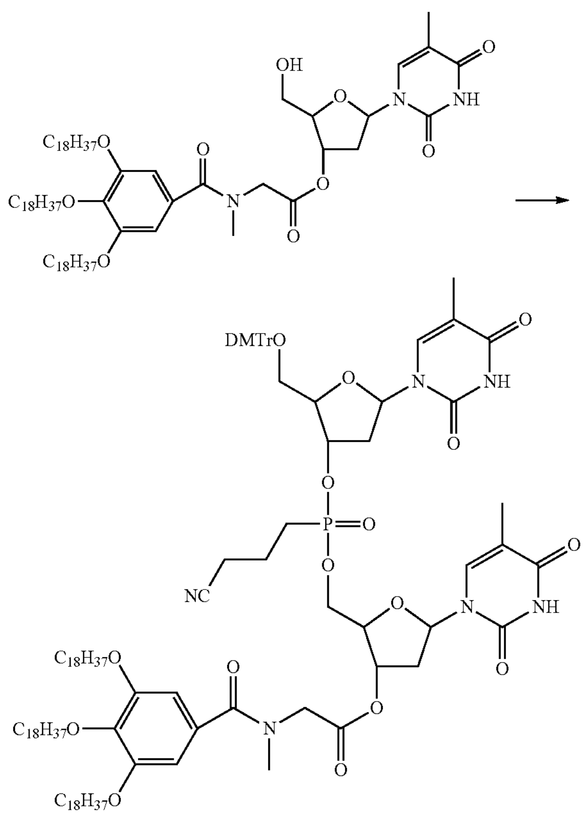

The title compound (2.54 g, 96%) was obtained from thymidine-3'-yl 2-(N-methyl-3,4,5-tris(octadecyloxy)benzamide)acetate (1.71 g, 1.40 mmol) and DMTr-dT-CE-phosphoroamidite (2.09 g, 2.80 mmol) as white solids according to the methods of Examples 3-4.

$^1$H-NMR (400 MHz, $CDCl_3$): δ 0.88 (t, 9H, J=6.6 Hz), 1.05-1.55 (m, 93H), 1.65-1.85 (m, 6H), 1.91 (s, 3H), 2.30-2.55 (m, 3H), 2.60-2.80 (m, 3H), 3.08 (s, 3H), 3.35-3.45 (m, 1H), 3.50-3.60 (m, 1H), 3.78 (s, 3H), 3.79 (s, 3H), 3.90-4.05 (m, 6H), 4.10-4.45 (m, 8H), 5.10-5.20 (m, 1H), 5.30-5.45 (m, 1H), 6.10-6.30 (brs, 1H), 6.35-6.45 (m, 1H), 6.64 (s, 2H), 6.75-6.90 (m, 4H), 7.15-7.40 (m, 10H), 7.49 (d, 1H, J=6.4 Hz), 8.50-8.75 (m, 2H).

$^{13}$C-NMR (100 MHz, $CDCl_3$): δ 11.76, 12.41, 12.46, 14.07, 19.63, 19.70, 19.78, 19.85, 22.70, 26.20, 29.37, 29.50, 29.52, 29.70, 29.75, 29.79, 30.43, 31.96, 36.86, 38.50, 39.03, 55.30, 55.34, 61.99, 62.10, 62.50, 62.55, 62.63, 63.33, 67.69, 69.61, 69.64, 73.60, 74.61, 79.78, 81.51, 82.43, 84.41, 84.52, 84.57, 85.65, 85.88, 86.36, 87.47, 106.43, 111.40, 111.78, 111.83, 111.89, 113.31, 113.50, 116.07, 116.42, 127.09, 127.38, 127.86, 128.11, 128.27, 129.21, 130.20, 135.07, 135.18, 135.45, 135.54, 136.37, 139.66, 140.30, 144.12, 147.51, 150.16, 150.21, 150.26, 150.38, 153.30, 158.81, 159.03, 163.33, 168.90, 172.25, 172.43.

TOF/MS (ESI): calcd for $C_{108}H_{165}N_6O_{19}PNa$ [M+Na]$^+$ 1904.1765, found 1904.1780.

Synthesis of 5'-O-((2-Cyanoethoxy)(5'-O-(4,4'-Dimethoxytrityl)Thymidine-3'-Yl)Phosphoryl)Thymidine-3'-Yl 3-(3,4,5-Tris(Octadecyloxy)Benzamide) Propionate Example 5-12

(1) Synthesis of 5'-O-(4,4'-Dimethoxytrityl)Thymidine-3'-Yl 3-(3, 4,5-Tris(Octadecyloxy)Benzamide) Propionate

[Chemical Formula 87]

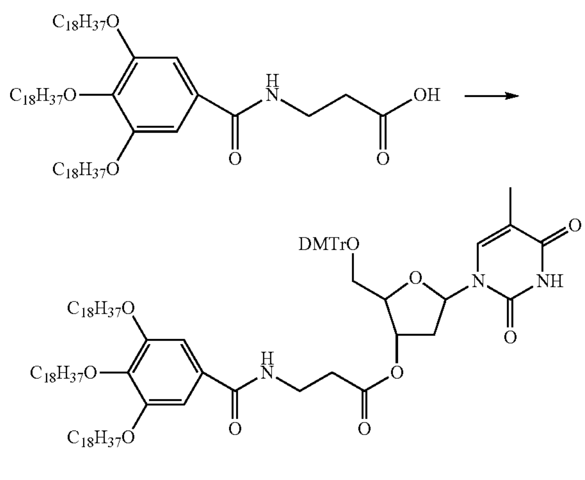

COMU (1.88 g, 4.40 mmol) was added to a suspension of 3-(3,4,5-tris(octadecyloxy)benzamide)propionic acid (2.20 g, 2.20 mmol), 5'-O-(4,4'-dimethoxytrityl)thymidine (1.44 g, 2.64 mmol), and 1-methylimidazole (0.90 g, 11.00 mmol) in THF (44 mL), and stirred at room temperature for 3.5 hours. Further, 1-methylimidazole (0.36 g, 4.4 mmol) and COMU (0.94 g, 2.20 mmol) were added, and the mixture was stirred at room temperature for 68 hours. The solid precipitated by dropping acetonitrile (220 mL) to the reaction solution was filtered. The solid was washed with acetonitrile—THF mixture solvent and methanol, and then dried under reduced pressure at 50° C. to obtain a crude compound (3.07 g). The crude compound was purified by column chromatography (spherical neutral silica gel, eluent: dichloromethane—THF) to give the title compound (2.01 g, 60%) as a white solid.

$^1$H-NMR (400 MHz, $CDCl_3$): δ 0.88 (t, 9H, J=6.8 Hz), 1.15-1.55 (m, 93H), 1.60-1.85 (m, 6H), 2.40-2.55 (m, 2H), 2.65-2.75 (m, 2H), 3.40-3.55 (m, 2H), 3.65-3.75 (m, 2H), 3.78 (s, 6H), 3.95-4.05 (m, 6H), 4.14 (d, 1H, J=1.6 Hz), 5.47 (d, 1H, J=4.8 Hz), 6.42 (t, 1H, J=6.2 Hz), 6.59 (t, 1H, J=6.0 Hz), 6.80-6.90 (m, 4H), 6.94 (s, 2H), 7.20-7.45 (m, 9H), 7.60 (s, 1H), 8.43 (s, 1H).

$^{13}$C-NMR (100 MHz, $CDCl_3$): δ 11.62, 14.14, 22.71, 26.11, 29.38, 29.45, 29.61, 29.68, 29.74, 30.33, 31.94, 34.05, 35.35, 37.92, 55.24, 63.65, 69.36, 73.51, 75.85, 83.94, 84.34, 87.24, 105.67, 111.65, 113.15, 113.32, 127.26, 127.76, 127.85, 128.06, 128.10, 129.12, 130.04, 130.08, 135.03, 135.24, 135.35, 141.26, 144.12, 150.23, 153.10, 158.78, 163.39, 167.36, 172.25.

TOF/MS (ESI): calcd for $C_{95}H_{149}N_3O_{12}Na$ [M+Na]$^+$ 1547.1039, found 1547.1014.

Example 5-13

(2) Synthesis of Thymidine-3'-Yl 3-(3,4,5-Tris(Octadecyloxy)Benz Amide)Propionate

[Chemical Formula 88]

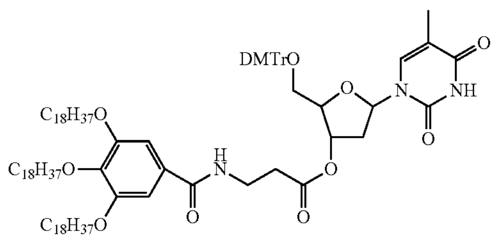

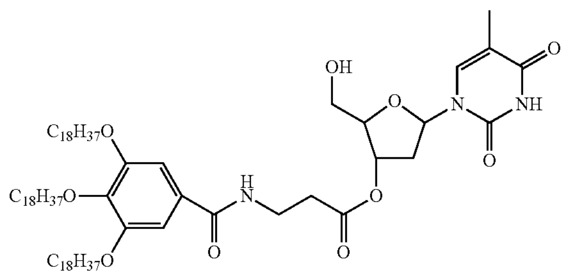

The title compound (1.51 g, 99%) was obtained as a white solid from 5'-O-(4,4'-dimethoxytrityl)thymidine-3'-yl 3-(3,4,5-tris(octadecyloxy)benzamide)propionate (1.91 g, 1.25 mmol) according to the method of Example 2-2.

$^{1}$H-NMR (400 MHz, $CDCl_3$): δ 0.88 (t, 9H, J=6.8 Hz), 1.15-1.55 (m, 90H), 1.65-1.85 (m, 6H), 1.91 (s, 3H), 2.30-2.55 (m, 2H), 2.55-2.75 (m, 3H), 3.65-3.75 (m, 2H), 3.85-3.95 (m, 2H), 3.95-4.05 (m, 6H), 4.05-4.10 (m, 1H), 5.35-5.40 (m, 1H), 6.16 (dd, 1H, J=6.0, 8.4 Hz), 6.55-6.65 (m, 1H), 6.95 (s, 2H), 7.43 (s, 1H), 8.25-8.55 (m, 1H).

$^{13}$C-NMR (100 MHz, $CDCl_3$): δ 12.51, 14.09, 22.71, 26.13, 26.16, 29.38, 29.47, 29.62, 29.69, 29.75, 29.99, 30.38, 31.96, 34.26, 35.57, 37.12, 62.57, 69.57, 73.59, 75.09, 85.06, 86.65, 106.04, 111.41, 129.08, 136.51, 141.64, 150.33, 153.20, 163.40, 167.46, 172.39.

TOF/MS (ESI): calcd for $C_{74}H_{131}N_3O_{10}Na$ $[M+Na]^+$ 1244.9732, found 1244.9789.

Examples 5-14

(3) Synthesis of 5'-O-((2-Cyanoethoxy)(5'-O-(4,4'-Dimethoxytrityl) Thymidine-3'-Yl)Phosphoryl)Thymidine-3'-Yl 3-(3,4,5-Tris(Octadecyloxy)Benzamide)Propionate

[Chemical Formula 89]

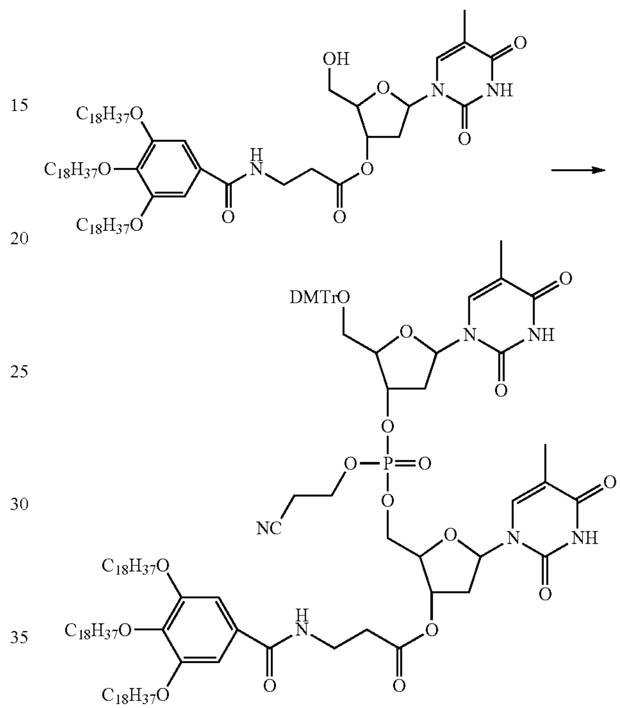

The title compound (2.07 g, 95%) was obtained as white solids from thymidine-3'-yl 3-(3,4,5-tris(octadecyloxy)benzamide)propionate (1.41 g, 1.15 mmol) and DMTr-dT-CE-phosphoroamidite (1.71 g, 2.30 mmol) according to the methods of Examples 3-4.

$^{1}$H-NMR (400 MHz, $CDCl_3$): δ 0.88 (t, 9H, J=6.8 Hz), 1.15-1.55 (m, 93H), 1.65-1.85 (m, 7H), 1.90 (d, 3H, J=1.2 Hz), 2.25-2.55 (m, 3H), 2.55-2.80 (m, 5H), 3.30-3.45 (m, 1H), 3.50-3.60 (m, 1H), 3.60-3.75 (m, 2H), 3.78 (s, 3H), 3.79 (s, 3H), 3.90-4.05 (m, 6H), 4.05-4.40 (m, 6H), 5.10-5.25 (m, 1H), 5.30-5.40 (m, 1H), 6.15-6.25 (m, 1H), 6.40-6.50 (m, 1H), 6.75-6.90 (m, 4H), 6.99 (d, 2H, J=3.6 Hz), 7.20-7.40 (m, 9H), 7.50-7.60 (m, 1H), 8.95-9.05 (m, 1H), 9.05-9.15 (m, 1H).

$^{13}$C-NMR (100 MHz, $CDCl_3$): δ 11.72, 12.49, 14.14, 19.59, 19.67, 19.75, 22.71, 26.11, 26.14, 29.38, 29.47, 29.63, 29.69, 29.75, 29.78, 30.35, 31.94, 34.03, 35.53, 35.58, 36.64, 38.95, 55.29, 62.36, 62.41, 62.52, 62.57, 63.24, 67.60, 69.38, 73.53, 73.84, 79.90, 82.35, 82.44, 84.25, 84.32, 84.39, 85.48, 85.67, 87.35, 105.86, 111.64, 111.74, 111.88, 113.14, 113.35, 116.25, 116.44, 127.34, 127.76, 127.85, 128.09, 129.03, 129.13, 130.13, 134.91, 134.95, 135.00, 135.07, 135.48, 135.61, 141.22, 143.93, 143.97, 150.21, 150.26, 150.46, 150.49, 153.03, 158.83, 163.48, 163.53, 167.47, 167.51, 172.19.

TOF/MS (ESI): calcd for $C_{108}H_{165}N_6O_{19}PNa$ $[M+Na]^+$ 1904.1765, found 1904.1807.

6. Synthesis of (4-(((6-($N^6$-Benzoyladenine-9-Yl)-4-Tritylmorpholin-2-Yl)Methoxy)(Dimethylamino) Phosphoryl)-6-(Thymine-1-Yl)Morpholin-2-Yl) Methyl 2-((3,4,5-Tris(Octadecyloxy)Benzoyl)Oxy) Acetate

Example 6-1

(1) Synthesis of (6-(Thymine-1-Yl)-4-Tritylmorpholin-2-Yl)Methyl 2-((3,4,5-Tris(Octadecyloxy)Benzoyl)Oxy)Acetate

[Chemical Formula 90]

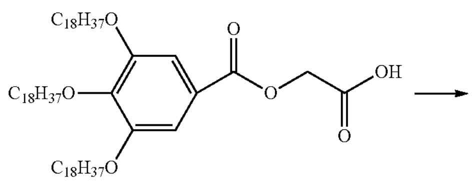

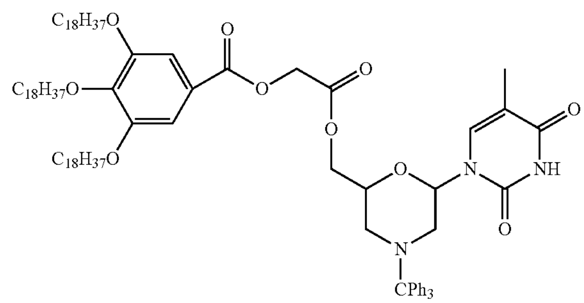

The title compound (2.85 g, 98%) was obtained from 2-((3,4,5-tris(octadecyloxy)benzoyl)oxy)acetic acid (1.97 g, 2.00 mmol) and 6-(hydroxymethyl)-4-tritylmorpholin-2-yl)-5-methylpyrimidine-2,4-(1H, 3H)-dione (1.16 g, 2.40 mmol) according to the procedure of Example 2-1.

$^1$H-NMR (400 MHz, $CDCl_3$): δ 0.88 (t, 9H, J=6.8 Hz), 1.11-1.53 (m, 91H), 1.68-1.83 (m, 6H), 1.84 (s, 3H), 3.13 (d, 1H, J=12.0 Hz), 3.37 (d, 1H, J=11.2 Hz), 3.98-4.04 (m, 6H), 4.17 (d, 2H, J=5.2 Hz), 4.37-4.41 (m, 1H), 4.78 (s, 2H), 6.13 (dd, 1H, J=2.0, 9.6 Hz), 7.00 (s, 1H), 7.15-7.26 (m, 3H), 7.26-7.38 (m, 8H), 7.34-7.58 (m, 6H), 8.34 (s, 1H).

$^{13}$C-NMR (100 MHz, $CDCl_3$): δ 12.45, 14.13, 22.70, 26.07, 26.11, 29.32, 29.38, 29.42, 29.59, 29.66, 29.68, 29.73, 30.35, 31.94, 49.01, 51.85, 60.89, 65.08, 69.19, 73.55, 74.58, 80.50, 108.31, 110.68, 123.33, 126.64, 127.97, 129.13, 135.33, 142.95, 149.63, 152.91, 163.23, 165.75, 167.64.

TOF/MS (ESI): calcd for $C_{92}H_{143}N_3O_{10}Na$ $[M+Na]^+$ 1473.0671, found 1473.0629.

Example 6-2

(2) Synthesis of (6-(Thymine-1-Yl)Morpholin-2-Yl) Methyl 2-((3,4,5-Tris(Octadecyloxy)Benzoyl)Oxy) Acetate Trifluoroacetic Acid Salt

[Chemical Formula 91]

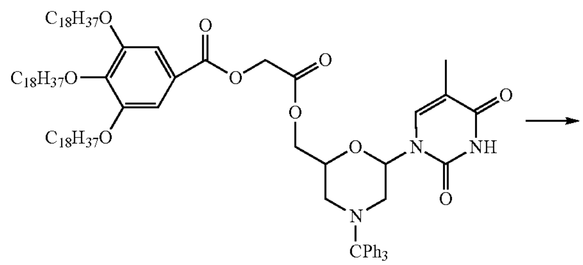

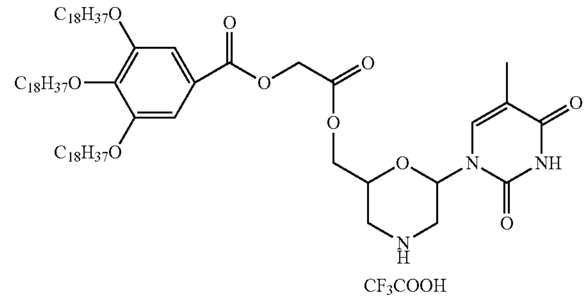

The title compound (2.44 g, 97%) was obtained from (6-(thy mine-1-yl)-4-tritylmorpholin-2-yl)methyl 2-((3,4,5-tris(octadecyloxy)benzoyl)oxy)acetate (2.76 g, 1.90 mmol) according to the method of Ex ample 2-2.

$^1$H-NMR (400 MHz, $CDCl_3$): δ 0.88 (t, 9H, J=6.8 Hz), 1.10-1.39 (m, 84H), 1.42-1.50 (m, 6H), 1.70-1.83 (m, 6H), 1.87 (s, 3H), 2.95-3.16 (m, 2H), 3.42 (d, 1H, J=11.2 Hz), 3.62-3.75 (m, 1H), 3.95-4.05 (m, 6H), 4.31 (d, 1H, J=8.4 Hz), 4.46 (d, 2H, J=10.0 Hz), 4.86 (s, 2H), 6.17 (d, 1H, J=9.6 Hz), 7.25 (s, 1H), 7.30 (s, 2H), 10.15-10.75 (brs, 1H).

$^{13}$C-NMR (100 MHz, $CDCl_3$): δ 12.48, 14.13, 22.71, 26.09, 26.15, 29.35, 29.39, 29.47, 29.63, 29.69, 29.75, 29.78, 30.38, 31.94, 43.24, 44.99, 60.87, 63.56, 69.21, 72.38, 73.57, 108.30, 112.18, 114.99, 117.90, 123.12, 134.33, 143.10, 150.40, 152.99, 162.55, 162.90, 163.78, 166.02, 167.45.

TOF/MS (ESI): calcd for $C_{73}H_{129}N_3O_{10}$—$CF_3COOH$ $[M-H]^-$ 1320.9528, found 1320.9517.

Example 6-3

(3) Synthesis of (4-(((6-($N^6$-Benzoyladenine-9-Yl)-4-Tritylmorpholin-2-Yl)Methoxy)(Dimethylamino)Phosphoryl)-6-(Thymine-1-Yl)Morpholin-2-Yl)Methyl 2-((3,4,5-Tris(Octadecyloxy)Benzoyl)Oxy)Acetate

[Chemical Formula 92]

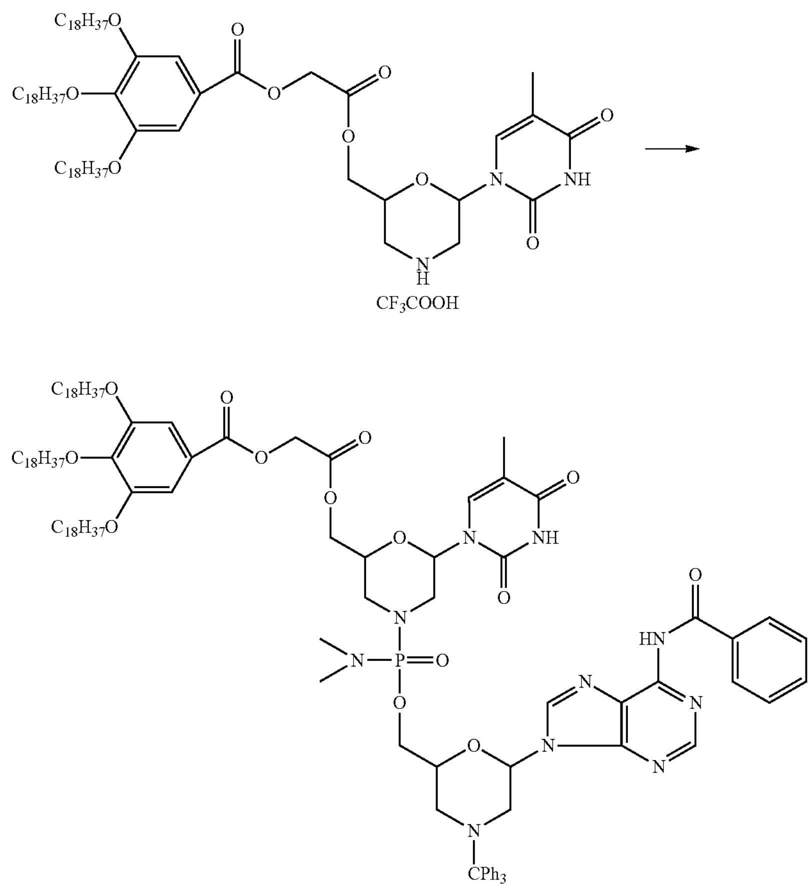

(6-($N^6$-benzoyladenine-9-yl)-4-tritylmorpholin-2-yl)methyldimethylphosphoramidechloridate (3.81 g, 5.27 mmol) was added to a solution of (6-(thymine-1-yl)morpholin-2-yl)methyl 2-((3,4,5-tris(octadecyloxy)benzoyl)oxy)acetate trifluoroacetic acid salt (2.32 g, 1.76 mmol) and N,N-diisopropylethylamine (4.16 g, 32.16 mmol) in 1,3-dimethyl-2-imidazolidinone (16 mL)—THF (18 mL), and then stirred at room temperature for 2.5 hours. The slurry liquid by adding methanol (93 mL) to the reaction solution was obtained, and then was concentrated under reduced pressure. The slurry liquid obtained by adding methanol to the concentrated residue was stirred at room temperature for 30 minutes, and then filtered. The solid was washed with methanol, and then dried under reduced pressure at 50° C. to obtain a crude compound (3.23 g). The crude compound was purified by column chromatography (spherical neutral silica gel, eluent: dichloromethane—methanol) to give the title compound (1.96 g, 59%) as a white solid.

$^1$H-NMR (400 MHz, $CDCl_3$): δ 0.88 (t, 9H, J=6.8 Hz), 1.10-1.53 (m, 90H), 1.55-1.97 (m, 12H), 2.46 (d, 3H, J=10.4 Hz), 2.63 (d, 3H, J=9.6 Hz), 2.46-2.63 (m, 1H), 3.12-3.60 (m, 4H), 3.75-4.07 (m, 10H), 4.15-4.50 (m, 2H), 4.78-4.91 (m, 2H), 5.41-5.53 (m, 1H), 6.42 (d, 1H, J=10.4 Hz), 7.12-7.20 (m, 4H), 7.20-7.32 (m, 9H), 7.40-7.58 (m, 8H), 8.05 (d, 2H, J=7.6 Hz), 8.07-8.10 (m, 1H), 8.68-8.80 (m, 1H), 9.50-9.76 (m, 2H).

$^{13}$C-NMR (100 MHz, $CDCl_3$): δ 12.44, 12.53, 14.14, 22.70, 26.08, 26.12, 29.32, 29.38, 29.43, 29.60, 29.68, 29.73, 30.35, 31.94, 36.47, 36.51, 36.63, 36.67, 44.56, 44.84, 47.02, 48.64, 48.78, 52.81, 53.10, 60.93, 64.23, 65.34, 65.69, 69.19, 73.56, 74.90, 74.97, 75.34, 79.53, 79.61, 79.97, 80.79, 108.27, 110.92, 111.25, 122.82, 123.26, 126.65, 128.00, 128.22, 128.29, 128.57, 128.63, 129.16, 132.47, 132.57, 133.49, 133.92, 134, 74, 134.80, 140.75, 140.78, 142.97, 143.00, 149.31, 149.68, 149.82, 150.12, 150.89, 151.40, 152.65, 152.77, 152.92, 152.94, 163.62, 165.02, 165.23, 165.82, 165.84, 167.56, 167.63.

TOF/MS (ESI): calcd for $C_{111}H_{165}N_{10}O_{14}PNa$ $[M+Na]^+$ 1916.2142, found 1916.2216.

Synthesis of (4-(((6-(N[4]-Benzoylcytosine-1-Yl)-4-Tritylmorpholin-2-Yl)Methoxy)(Dimethylamino) Phosphoryl)-6-(N[2]-Isobutyrylguanine-9-Yl) Morpholin-2-Yl)Methyl 2-((3,4,5-Tris(Octadecyloxy) Benzoyl)Oxy)Acetate Example 6-4

(1) Synthesis of (6-(N[2]-Isobutyrylguanine-9-Yl)-4-Tritylmorpholin-2-Yl)Methyl 2-((3,4,5-Tris(Octadecyloxy)Benzoyl)Oxy)Acetate

[Chemical Formula 93]

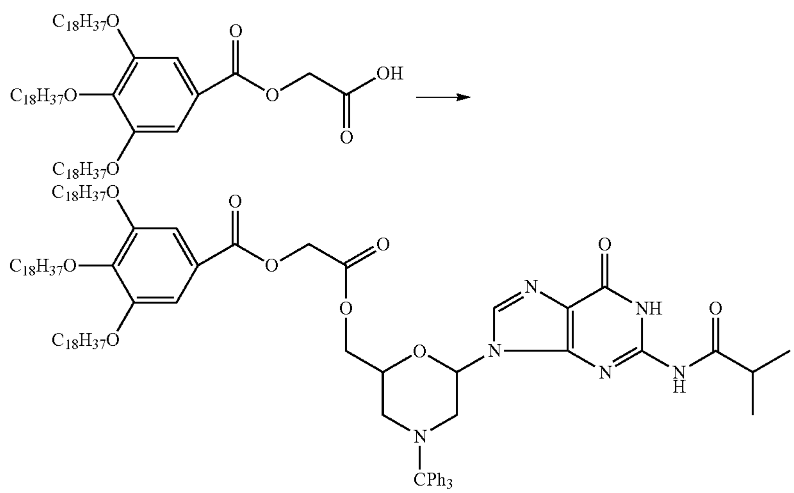

The title compound (3.00 g, 97%) was obtained from 2-((3,4,5-tris(octadecyloxy)benzoyl)oxy)acetic acid (1.97 g, 2.00 mmol) and N-(9-(6-(hydroxymethyl)-4-tritylmorpholin-2-yl))-6-oxo-6,9-dihydro-1H-purine-2-yl)isobutylamide (1.51 g, 2.60 mmol) according to the procedure of Example 2-1.

$^{1}$H-NMR (400 MHz, $CDCl_3$): δ 0.88 (t, 9H, J=6.8 Hz), 1.10-1.60 (m, 97H), 1.70-1.90 (m, 7H), 2.64 (sept, 1H), 3.18 (d, 1H, J=12.0 Hz), 3.45 (d, 1H, J=11.6 Hz), 3.95-4.15 (m, 6H), 4.13-4.25 (m, 2H), 4.37-4.46 (m, 1H), 4.72 (d, 1H, J=16.0 Hz), 4.84 (d, 1H, J=16.0 Hz), 5.89 (dd, 1H, J=2.2, 9.8 Hz), 7.06-7.37 (m, 12H), 7.39-7.55 (m, 5H), 7.61 (s, 1H), 8.18 (s, 1H), 11.92 (s, 1H).

$^{13}$C-NMR (100 MHz, $CDCl_3$): δ 14.14, 18.93, 19.03, 22.71, 26.07, 26.12, 29.33, 29.37, 29.42, 29.60, 29.67, 29.74, 30.35, 31.94, 36.64, 49.04, 52.24, 60.90, 65.03, 69.25, 73.58, 74.22, 80.36, 108.38, 121.30, 123.27, 126.69, 127.96, 129.18, 136.12, 143.08, 147.32, 147.42, 152.95, 155.36, 165.98, 167.61, 177.85.

TOF/MS (ESI): calcd for $C_{96}H_{148}N_6O_{10}Na$ $[M+Na]^+$ 1568.1155, found 1568.1176.

Example 6-5

(2) Synthesis of (6-(N[2]-Isobutyrylguanine-9-Yl) Morpholin-2-Yl)Methyl 2-((3,4,5-Tris(Octadecyloxy)Benzoyl)Oxy)Acetate Trifluoroacetic Acid Salt

[Chemical Formula 94]

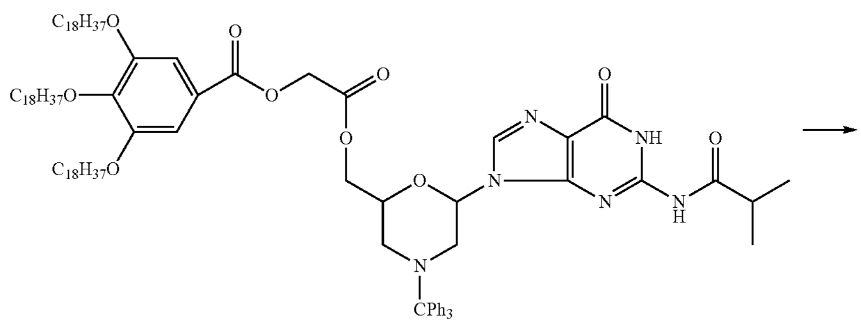

-continued

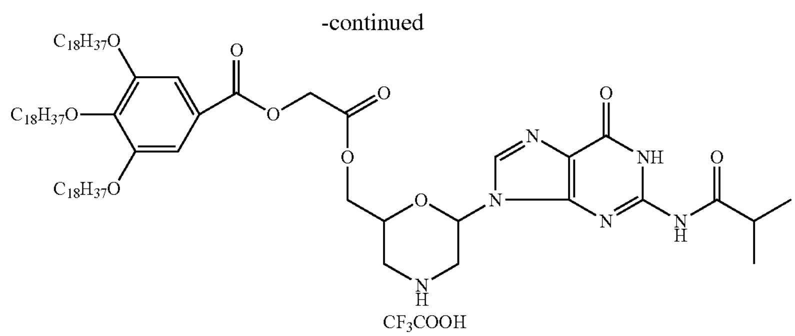

The title compound (2.45 g, 96%) was obtained from (6-($N^2$-isobutyrylguanine-9-yl)-4-tritylmorpholin-2-yl) methyl 2-((3,4,5-tris(octadecyloxy)benzoyl)oxy)acetate (2.78 g, 1.80 mmol) according to the procedure of Example 2-2.

$^1$H-NMR (400 MHz, $CDCl_3$): δ 0.87 (t, 9H, J=6.8 Hz), 1.00-1.53 (m, 96H), 1.69-1.88 (m, 6H), 2.72-2.88 (m, 1H), 3.19-3.38 (m, 1H), 3.44-3.63 (m, 1H), 3.75-4.13 (m, 8H), 4.25-4.63 (m, 3H), 4.69-4.94 (m, 2H), 6.06-6.31 (m, 1H), 7.20-7.30 (m, 3H), 7.87-8.06 (m, 1H), 10.19-10.63 (brs, 1H), 12.19-12.63 (brs, 1H).

$^{13}$C-NMR (100 MHz, $CDCl_3$): δ 14.12, 18.92, 22.70, 26.09, 26.16, 29.35, 29.38, 29.47, 29.63, 29.68, 29.75, 29.79, 30.04, 30.38, 31.94, 36.17, 42.86, 60.73, 63.62, 69.21, 71.44, 73.57, 108.29, 115.13, 118.04, 123.10, 143.09, 148.28, 152.95, 156.00, 165.93, 167.50, 180.39.

TOF/MS (ESI): calcd for $C_{77}H_{134}N_6O_{10}$—$CF_3COOH$ $[M-H]^-$ 1416.0012, found 1415.9960.

Example 6-6

(3) Synthesis of (4-(((6-($N^4$-Benzoylcytosine-1-Yl)-4-Tritylmorpholin-2-Yl)Methoxy)(Dimethylamino) Phosphoryl)-6-($N^2$-Isobutyrylguanine-9-Yl)Morpholin-2-Yl)Methyl 2-((3,4,5-Tris(Octadecyloxy) Benzoyl)Oxy)Acetate

[Chemical Formula 95]

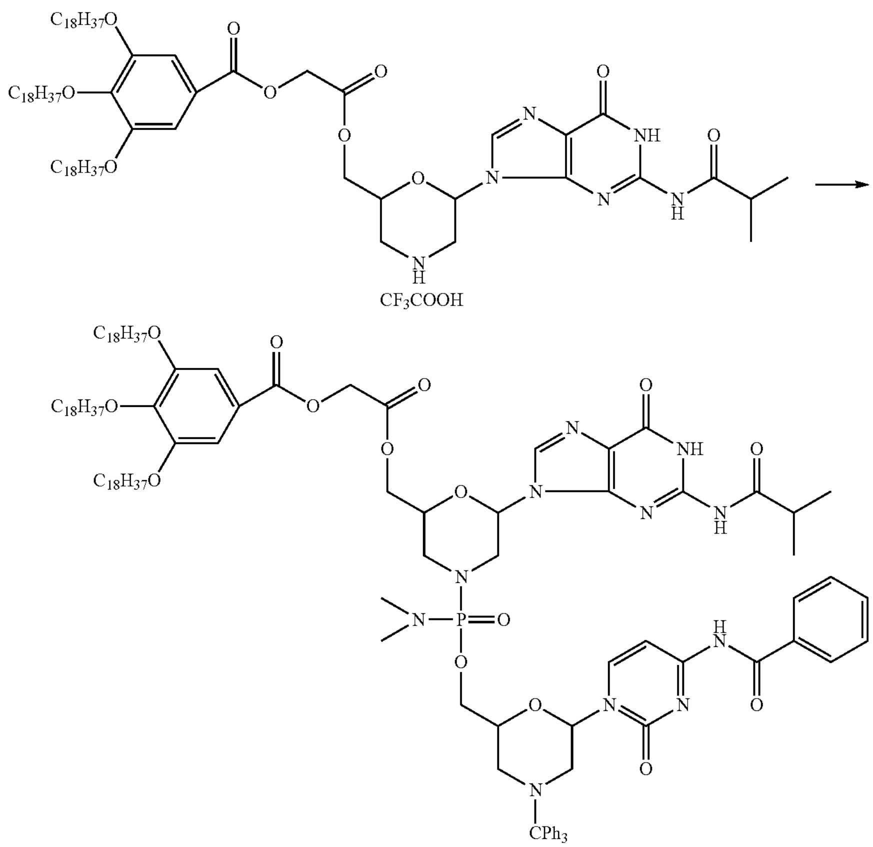

The title compound (2.87 g, 91%) was obtained from (6-($N^2$-isobutyrylguanine-9-yl)morpholin-2-yl)methyl 2-((3,4,5-tris(octadecyloxy)benzoyl)oxy)acetate trifluoroacetic acid salt (2.27 g, 1.60 mmol) and (6-($N^4$-benzoylcytosine-1-yl)-4-tritylmorpholin-2-yl)methyldimethylphosphoramidochloridate (3.35 g, 4.80 mmol) according to the procedure of Example 6-3.

$^1$H-NMR (400 MHz, $CDCl_3$): δ 0.88 (t, 9H, J=6.8 Hz), 1.00-1.56 (m, 96H), 1.69-1.88 (m, 9H), 2.38-2.97 (m, 8H), 3.06-3.69 (m, 5H), 3.75-4.56 (m, 12H), 4.69-4.94 (m, 2H), 5.34-5.63 (m, 1H), 6.28-6.50 (m, 1H), 7.13-8.00 (m, 23H), 8.69-8.94 (brs, 1H), 9.31-9.63 (brs, 1H), 10.06-10.31 (brs, 1H), 12.13-12.31 (m, 1H).

$^{13}$C-NMR (100 MHz, $CDCl_3$): δ 14.13, 19.01, 19.04, 19.17, 19.22, 22.70, 26.07, 26.12, 29.32, 29.37, 29.43, 29.60, 29.67, 29.73, 29.98, 30.35, 31.94, 36.17, 36.27, 36.64, 36.68, 36.74, 36.78, 45.00, 45.08, 46.96, 47.43, 48.25, 48.76, 52.48, 60.82, 60.90, 64.27, 65.84, 69.20, 69.22, 73.57, 74.31, 74.51, 75.41, 79.30, 80.47, 81.36, 81.59, 108.31, 121.25, 122.00, 123.26, 123.33, 126.67, 126.73, 127.73, 127.99, 128.80, 128.98, 132.71, 133.07, 133.27, 136.19, 137.10, 142.90, 143.01, 147.88, 148.00, 148.09, 152.89, 152.93, 155.79, 155.90, 165.79, 165.91, 167.56, 167.58, 178.67, 179.37.

TOF/MS (ESI): calcd for $C_{114}H_{170}N_{11}O_{15}PNa$ $[M+Na]^+$ 1987.2513, found 1987.2521.

7. Confirmation of Tag Removal

Example 7-1

Synthesis of 5'-O-((2-Cyanoethoxy)(5'-O-((2-Cyanoethoxy)(5'-O-(4,4'-Dimethoxytrityl)Thymidine-3'-Yl)Phosphoryl)-$N^2$-Isobutyryldeoxyguanosine-3'-Yl) Phosphoryl)Thymidine

[Chemical Formula 96]

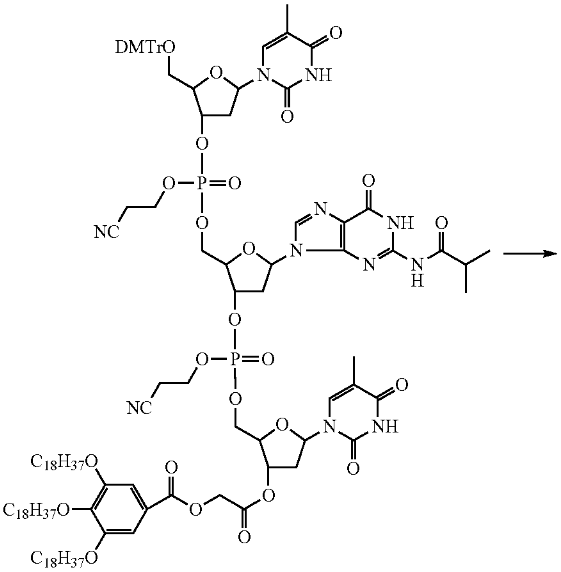

-continued

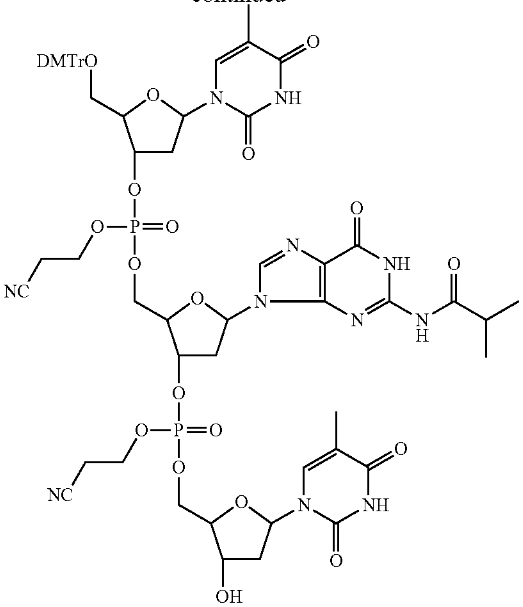

A mixture solution of 5'-O-((2-cyanoethoxy)(5'-O-((2-cyanoethoxy) (5'-O-(4,4'-dimethoxytrityl)thymidine-3'-yl) phosphoryl)-$N^2$-isobutyryl deoxyguanosine-3'-yl)phosphoryl)thymidine-3'-yl 2-((3,4,5-tris(octadecyloxy)benzoyl) oxy)acetate (233 mg, 0.10 mmol) in THF (9 mL)—2-propanol (1 mL) was cooled to 0° C. In cool, 4 mol/L—lithium borohydride—THF solution (0.125 m L, 0.50 mmol) was added and stirred at the same temperature for 30 min. An aqueous ammonium chloride solution was added to the reaction solution, and then extracted 3 times with dichloromethane. The organic layer was washed with brine, dried over anhydrous sodium sulfate, filtered to remove sodium sulfate, and then the filtrate was concentrated. The solid precipitated by suspending the concentrated residue in acetonitrile was removed by filtration, and the filtrate was concentrated. A portion (2.5 mL) of the dimethyl sulfoxide—methanol mixture solution (1:1, 5 mL) of the concentrated residue was purified by preparative chromatography in 5 portions to give the title compound (64 mg, 95%) as a white solid.

Preparative chromatographic conditions: Column MightysilRP-18 GP (5 μm, 20 Φ×250 mm) manufactured by Kanto Chemical Co., Lt d., flow rate 5 mL/min, mobile phase acetonitrile-water (gradient 0-30 min (ratio of acetonitrile 50→60%)

$^1$H-NMR (600 MHz, DMSO-$d_6$): δ 1.12 (d, 6H, J=6.0 Hz), 1.42 (d, 3H, J=7.2 Hz), 1.74 (d, 3H, J=2.8 Hz), 2.07 (s, 1H), 2.30-2.41 (m, 3H), 2.60-2.90 (m, 6H), 3.18-3.29 (m, 2H), 3.73 (d, 6H, J=4.2 Hz), 4.00-4.43 (m, 12H), 4.97 (s, 1H), 5.10 (s, 1H), 5.51-5.52 (m, 1H), 6.15-6.25 (m, 3H), 6.88 (d, 4H, J=9.0 Hz), 7.20-7.50 (m, 11H), 8.17 (q, 1H, J=1.8 Hz), 11.33-12.07 (m, 3H).

$^{13}$C-NMR (151 MHz, DMSO-$d_6$): δ 10.56, 10.88, 17.66, 33.65, 35.78, 52.00, 53.86, 56.34, 61.48, 61.80, 65.49, 66.58, 68.73, 76.58, 77.11, 81.63, 82.11, 82.52, 82.87, 84.98, 90.73, 108.72, 112.08, 116.98, 119.14, 125.69, 126.46, 126.77, 128.53, 133.81, 134.00, 134.26, 134.70, 136.15, 143.26, 147.04, 147.32, 149.14, 153.53, 156.99, 162.50, 168.14, 178.89.

TOF/MS (ESI): calcd for $C_{61}H_{69}N_{11}O_{21}P_2Na$ $[M+Na]^+$ 1376.4, found 1376.6.

Example 7-2

Synthesis of 5'-O-((2-Cyanoethoxy)(5'-O-((2-Cyanoethoxy)(5'-O-(4,4'-Dimethoxytrityl)-$N^2$-Isobutyryldeoxyguanosine-3'-Yl)Phosphoryl)Thymidine-3'-Yl)Phosphoryl)-$N^6$-Benzoyldeoxyadenosine

[Chemical Formula 97]

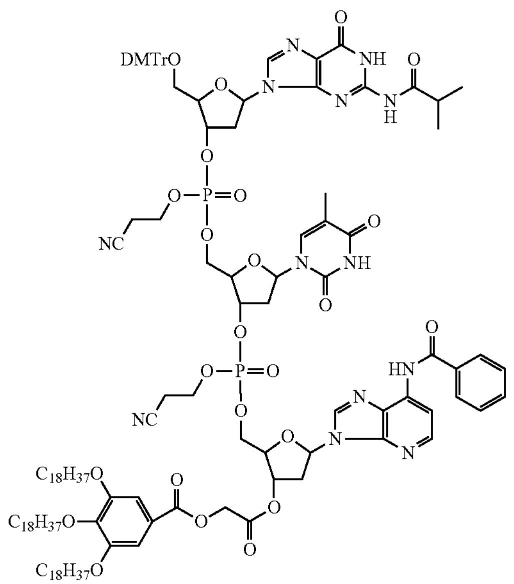

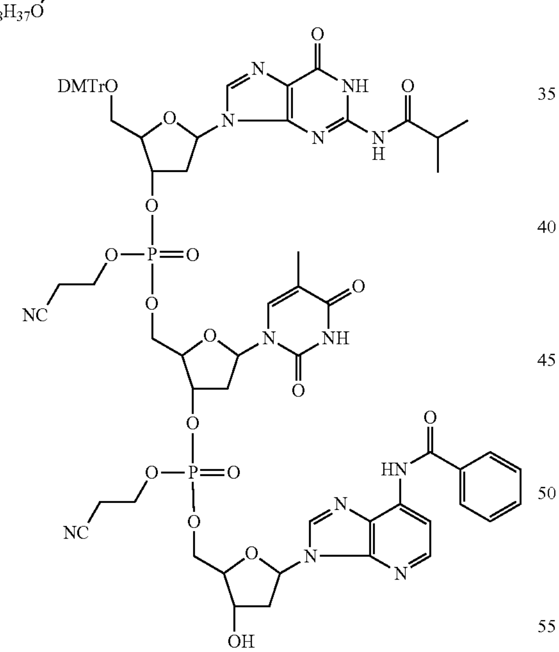

The title compound (55 mg, 75%) was obtained as a yellow solid from 5'-O-((2-cyanoethoxy)(5'-O-((2-cyanoethoxy)(5'-O-(4,4'-dimethoxytrityl)-$N^2$-isobutyldeoxyguanosine-3'-yl)phosphoryl)thymidine-3'-yl)phosphoryl)-$N^6$-benzoyldeoxyadenosine-3'-yl 2-((3,4,5-tris(octadecyloxy) benzoyl)oxy)acetate (244 mg, 0.10 mmol) according to the procedure of Example 7-1.

$^1$H-NMR (600 MHz, DMSO-$d_6$): δ 1.17-1.30 (m, 7H), 1.74-1.79 (m, 3H), 1.97-2.30 (m, 2H), 2.45-2.51 (m, 2H), 2.68-2.76 (m, 1H), 2.79-2.83 (m, 1H), 2.96 (dt, 4H, J=6.4, 12.4 Hz), 3.03-3.12 (m, 1H), 3.22 (t, 1H, J=11.3 Hz), 3.77 (s, 6H), 3.93 (s, 1H), 4.07-4.38 (m, 11H), 5.07-5.45 (m, 5H), 6.05-6.45 (m, 3H), 6.85 (t, 4H, J=10.7 Hz), 7.24 (d, 5H, J=8.9 Hz), 7.29 (t, 2H, J=7.6 Hz), 7.36 (d, 2H, J=7.6 Hz), 7.49-7.56 (m, 3H), 7.65 (t, 1H, J=7.2 Hz), 7.90 (dt, 1H, J=3.0, 8.1 Hz), 8.07 (d, 2H, J=7.6 Hz), 8.13-8.16 (m, 1H), 10.89-12.13 (m, 3H).

$^{13}$C-NMR (151 MHz, DMSO-$d_6$): δ 12.52, 14.58, 19.33, 35.33, 36.13, 37.02, 55.48, 60.34, 62.73, 63.24, 64.06, 67.31, 68.33, 70.66, 77.30, 79.12, 82.64, 83.37, 84.09, 84.74, 86.25, 113.58, 118.69, 121.00, 123.54, 127.24, 128.19, 128.72, 128.94, 130.23, 132.68, 133.50, 134.55, 135.77, 136.46, 137.81, 139.68, 145.08, 148.56, 149.12, 150.82, 155.31, 158.56, 161.08, 164.11, 165.03, 180.61.

TOF/MS (ESI): calcd for $C_{68}H_{72}N_{14}O_{20}P_2Na$ $[M+Na]^+$ 1489.4, found 1489.4.

Example 7-3

Synthesis of 5'-O-((2-Cyanoethoxy)(5'-O-((2-Cyanoethoxy)(5'-O-(4,4'-Dimethoxytrityl)Thymidine-3'-Yl)Phosphoryl)-$N^2$-Isobutyryldeoxyguanosine-3'-Yl) Phosphoryl)-$N^4$-Benzoyldeoxycytidine

[Chemical Formula 98]

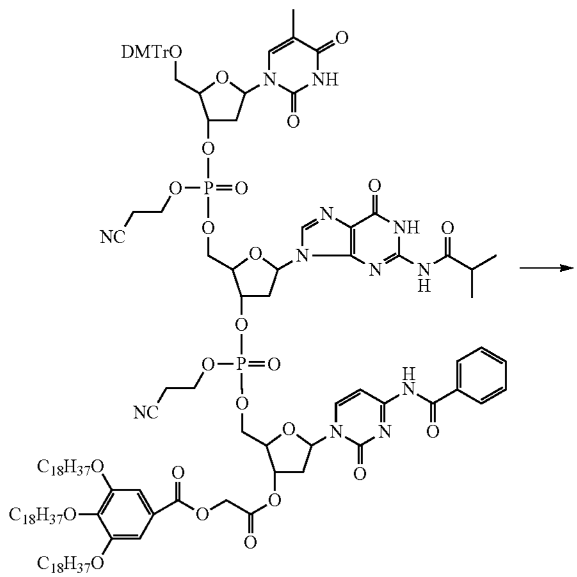

-continued

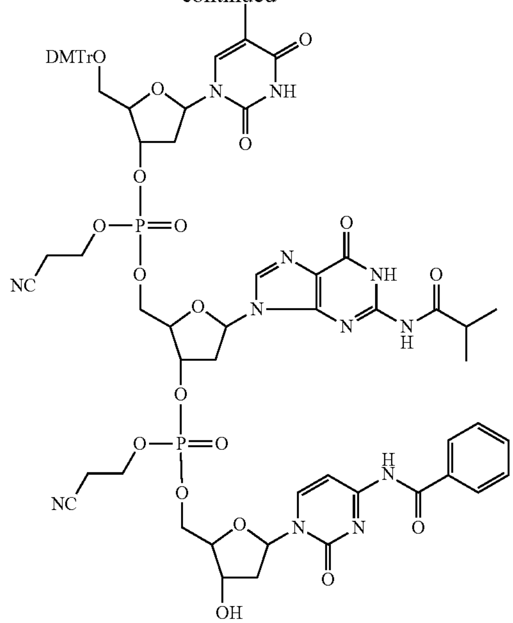

The title compound (57 mg, 79%) was obtained as a white solid from 5'-O-((2-cyanoethoxy)(5'-O-((2-cyanoethoxy)(5'-O-(4,4'-dimethoxytrityl) thymidine-3'-yl)phosphoryl)-$N^2$-isobutyryldeoxyguanosine-3'-yl)phosphoryl)-$N^4$-benzoyldeoxycytidine-3'-yl 2-((3,4,5-tris(octadecyloxy)benzoyl)oxy)acetate (243 mg, 0.10 mmol) according to the procedure of Example 7-1.

$^1$H-NMR (600 MHz, DMSO-$d_6$): δ 1.09-1.12 (m, 6H), 1.42 (s, 3H), 1.75-2.10 (m, 4H), 2.61-2.95 (m, 7H), 3.15-3.25 (m, 3H), 3.70-3.77 (m, 7H), 4.08-4.36 (m, 11H), 5.09 (d, 2H, J=41.9 Hz), 5.32 (d, 2H, J=44.0 Hz), 6.18-6.29 (m, 3H), 6.85-6.88 (m, 4H), 7.20-7.22 (m, 5H), 7.29 (q, 2H, J=6.9 Hz), 7.34 (d, 2H, J=7.6 Hz), 7.41-7.53 (m, 4H), 7.86 (d, 2H, J=7.6 Hz), 8.19 (dt, 1H, J=4.4, 8.2 Hz), 8.84 (q, 1H, J=6.4 Hz), 11.34-12.05 (m, 3H).

$^{13}$C-NMR (151 MHz, DMSO-$d_6$): δ 12.17, 19.35, 27.86, 35.35, 55.56, 57.07, 63.19, 63.61, 67.29, 68.60, 70.86, 78.19, 78.93, 82.62, 83.40, 83.86, 84.14, 86.67, 110.47, 113.78, 118.59, 118.88, 120.91, 127.38, 128.02, 128.69, 130.24, 131.86, 134.55, 135.51, 135.97, 137.92, 144.97, 148.76, 149.02, 150.84, 154.36, 155.25, 158.69, 164.09, 165.95, 166.18, 180.60.

TOF/MS (ESI): calcd for $C_{67}H_{72}N_{12}O_{21}P_2Li$ $[M+Li]^+$ 1449.5, found 1449.6.

Example 7-4

Synthesis of 5'-O-((2-Cyanoethoxy)(5'-O-((2-Cyanoethoxy)(5'-O-(4,4'-Dimethoxytrityl)Thymidine-3'-Yl)Phosphoryl)Thymidine-3'-Yl)Phosphoryl)-$N^2$-Isobutyryldeoxyguanosine

[Chemical Formula 99]

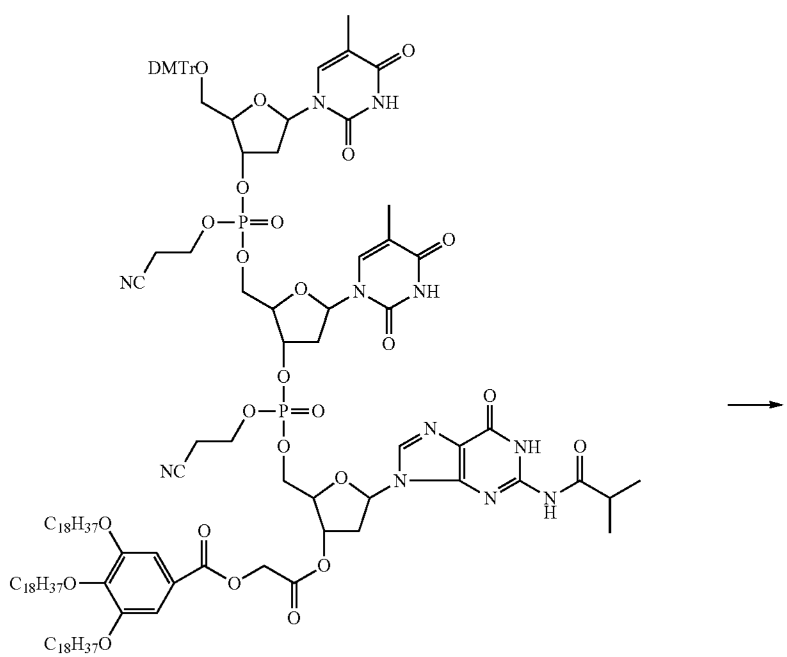

-continued

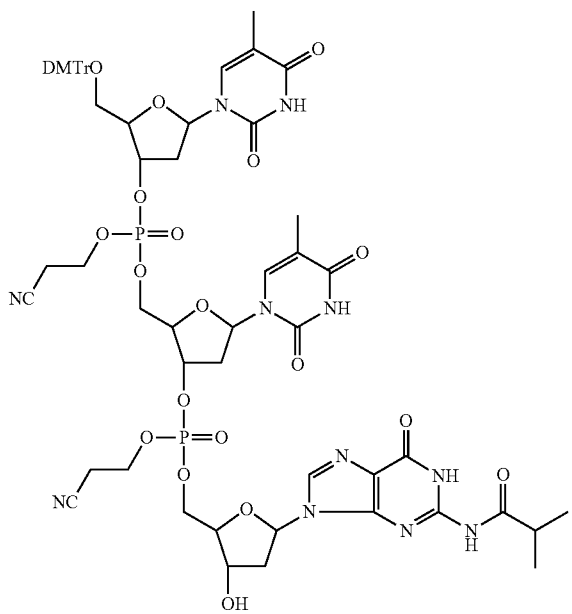

The title compound (63 mg, 93%) was obtained as a white solid from 5'-O-((2'-cyanoethoxy)(5'-O-(2'-cyanoethoxy)(5'-O-(4,4'-dimethoxytrityl) thymidine-3'-yl)phosphoryl) thymidine-3'-yl)phosphoryl)-$N^2$-isobutyldeoxianosine-3'-yl 2-((3,4,5-tris(octadecyloxy)benzoyl)oxy)acetate (232 m g, 0.10 mmol) according to the method of Example 7-1.

$^1$H-NMR (600 MHz, DMSO-$d_6$): δ 1.12 (d, 6H, J=6.2 Hz), 1.42 (d, 3H, J=7.6 Hz), 1.73 (d, 3H, J=2.7 Hz), 2.07 (s, 1H), 2.32-2.43 (m, 3H), 2.61-2.91 (m, 6H), 3.20-3.29 (m, 2H), 3.73 (d, 6H, J=3.8 Hz), 4.04-4.43 (m, 12H), 4.97 (s, 1H), 5.10 (s, 1H), 5.51-5.52 (m, 1H), 6.13-6.26 (m, 3H), 6.88 (d, 4H, J=8.9 Hz), 7.23 (d, 5H, J=7.6 Hz), 7.30 (t, 2H, J=6.2 Hz), 7.36 (d, 2H, J=8.2 Hz), 7.43-7.47 (m, 2H), 7.89-8.18 (m, 1H), 11.33-12.07 (m, 3H).

$^{13}$C-NMR (151 MHz, DMSO-$d_6$): δ 10.46, 10.84, 17.69, 17.83, 33.61, 35.32, 36.22, 53.86, 61.50, 61.98, 65.53, 66.44, 68.89, 75.88, 77.15, 80.92, 81.78, 82.16, 82.47, 82.92, 83.51, 85.00, 108.75, 108.90, 112.08, 116.92, 119.11, 125.71, 126.48, 126.77, 128.55, 133.80, 134.02, 134.33, 134.53, 136.24, 143.27, 146.96, 147.20, 149.17, 153.63, 157.01, 162.41, 178.92.

TOF/MS (ESI): calcd for $C_{61}H_{69}N_{11}O_{21}P_2Na$ [M+Na]$^+$ 1376.4, found 1376.6.

Example 7-5

Synthesis of 5'-O-((2-Cyanoethoxy)(5'-O-(4,4'-Dimethoxytrityl)-Thymidine-3'-Yl)Phosphorothioyl)-Thymidine

[Chemical Formula 100]

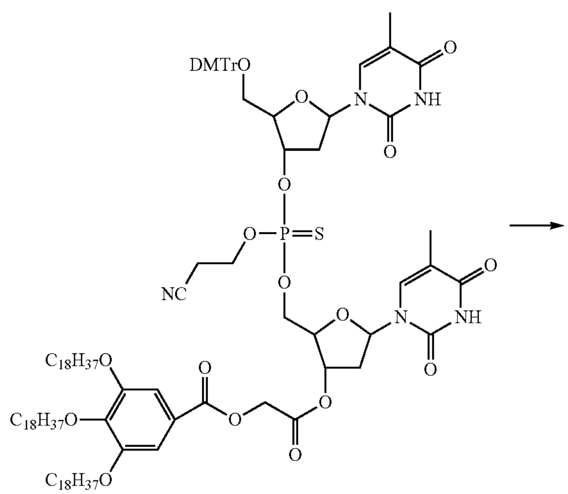

-continued

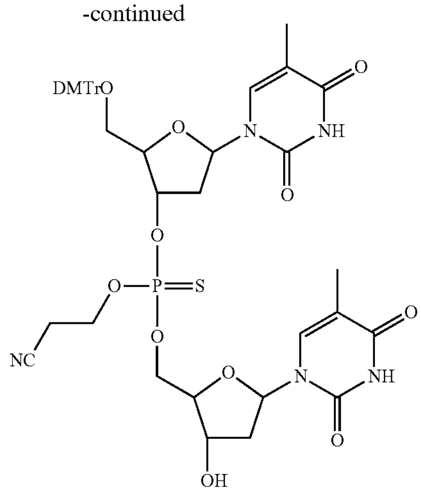

A mixture solution of 5'-O-((2-cyanoethoxy)(5'-O-(4,4'-dimethoxytrityl)-thymidine-3'-yl)phosphorothioyl)-thymidine-3'-yl 2-((3,4,5-tris (octadecyloxy)benzoyl)oxy)acetate (189 mg, 0.10 mmol) in THF (9 m L)-2-propanol (1 mL) was cooled to 0° C. In cool, 4 mol/L—lithium borohydride—THF solution (0.125 m L, 0.50 mmol) was added and stirred at the same temperature for 30 min. An aqueous ammonium chloride solution was added to the reaction solution, and then extracted 3 times with dichloromethane.

The organic layer was washed with brine, dried over anhydrous sodium sulfate, filtered to remove sodium sulfate, and then the filtrate was concentrated. The solid precipitated by suspending the concentrated residue in acetonitrile was removed by filtration, and the filtrate was concentrated. The concentrated residue was purified by column chromatography (silica gel, eluent: chloroform—methanol) to give the title compound (86 mg, 93%) as a white solid.

$^1$H-NMR (600 MHz, $CDCl_3$): δ 1.46 (d, 3H, J=15.8 Hz), 1.91 (d, 3H, J=8.2 Hz), 2.21-2.79 (m, 6H), 3.39-3.49 (m, 2H), 3.79 (d, 6H, J=3.4 Hz), 4.08-4.52 (m, 8H), 5.26-5.31 (m, 1H), 6.25-6.41 (m, 2H), 6.85 (dd, 4H, J=2.7, 8.9 Hz), 7.22-7.38 (m, 9H), 7.58 (d, 1H, J=24.1 Hz), 9.45-10.50 (m, 2H).

$^{13}$C-NMR (151 MHz, $CDCl_3$): δ 11.90, 12.57, 19.43, 38.92, 39.90, 55.30, 62.59, 63.36, 67.70, 71.03, 80.38, 84.66, 85.46, 87.28, 111.32, 111.97, 113.38, 116.54, 127.28, 128.00, 128.11, 130.06, 135.00, 135.80, 144.09, 150.64, 150.92, 158.74, 163.98.

TOF/MS (ESI): calcd for $C_{44}H_{48}N_5O_{13}PSNa$ $[M+Na]^+$ 940.3, found 940.2.

Example 7-6

Synthesis of 5'-O-((2-Cyanoethoxy)(5'-O-(4,4'-Dimethoxytrityl)-2'-Fluorodeoxyuridine-3'-Yl)Phosphoryl)-2'-Fluoro-$N^2$-Isobutyryldeoxyguanosine

[Chemical Formula 101]

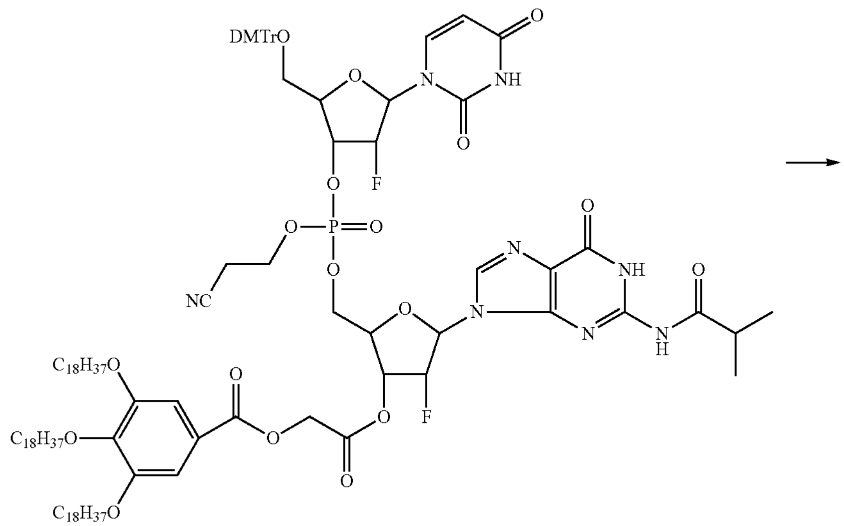

-continued

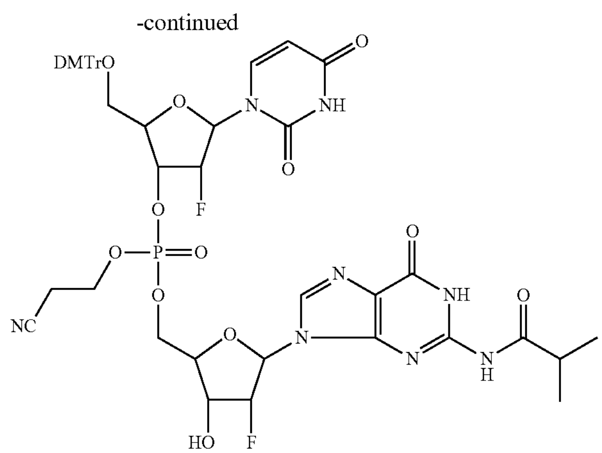

A mixture solution of 5'-O-((2-cyanoethoxy)(5'-O-(4,4'-dimethoxytrityl)-2'-fluorodeoxyuridin-3'-yl)phosphoryl)-2'-fluoro-$N^2$-isobutyryldeoxyguanosine-3'-yl 2-((3,4,5-tris(octadecyloxy)benzoyl)oxy)acetate (0.397 g, 0.200 mmol) in THF (27 mL)—2-propanol (3 mL) was cooled to 0 to −10° C. In cool, 4 mol/L—lithium borohydride—THF solution (0.10 m L, 0.400 mmol) was added and stirred at the same temperature for 20 min. 10% aqueous ammonium chloride (4 mL) was added to the reaction solution, and then the mixture was separated, and the organic layer was washed with 10% brine. The organic layer was dried over anhydrous sodium sulfate, filtered to remove sodium sulfate, and then the filtrate was concentrated. The solid precipitated by adding methanol to the concentrated residue was removed by filtration, and the filtrate was concentrated and dried. The concentrated residue was purified by column chromatography (spherical neutral silica gel, eluent: dichloromethane—methanol) to give the title compound (0.137 g, 67%) as a white solid.

$^1$H-NMR (400 MHz, $CDCl_3$): δ 1.16-1.26 (m, 6H), 2.19 (s, 2H), 2.45-2.87 (m, 3H), 3.44-3.66 (m, 2H), 3.72-3.75 (m, 6H), 3.92-4.18 (m, 2H), 4.25-4.50 (m, 4H), 4.89-5.55 (m, 6H), 5.85-6.00 (m, 2H), 6.80-6.82 (m, 4H), 7.15-7.30 (m, 7H), 7.33-7.37 (m, 2H), 7.71-7.82 (m, 2H), 10.05-10.42 (brs, 1H), 10.55-10.87 (brs, 1H), 12.36 (s, 1H).

$^{13}$C-NMR (100 MHz, $CDCl_3$): δ 18.75, 18.85, 19.01, 19.07, 19.38, 19.45, 36.01, 50.81, 55.26, 55.28, 60.65, 62.85, 67.86, 80.26, 81.13, 87.13, 87.19, 87.53, 87.88, 90.59, 92.53, 102.62, 113.33, 116.74, 121.28, 127.26, 128.05, 128.19, 130.22, 134.80, 134.91, 134.96, 135.07, 140.41, 144.01, 144.11, 148.00, 148.06, 148.50, 148.55, 150.44, 155.70, 158.76, 163.72, 180.33, 180.39.

TOF/MS (ESI): calcd for $C_{47}H_{49}N_8O_{14}F_2PNa$ $[M+Na]^+$ 1041.2972, found 1041.2975.

Examples 7-7

Synthesis of $N^4$-Benzoyl-5'-O-((2-Cyanoethoxy)(5'-O-(4,4'-Dimethoxytrityl)-2'-O-Methyluridine-3'-Yl) Phosphoryl)-2'-O-Methylcytidine

[Chemical Formula 102]

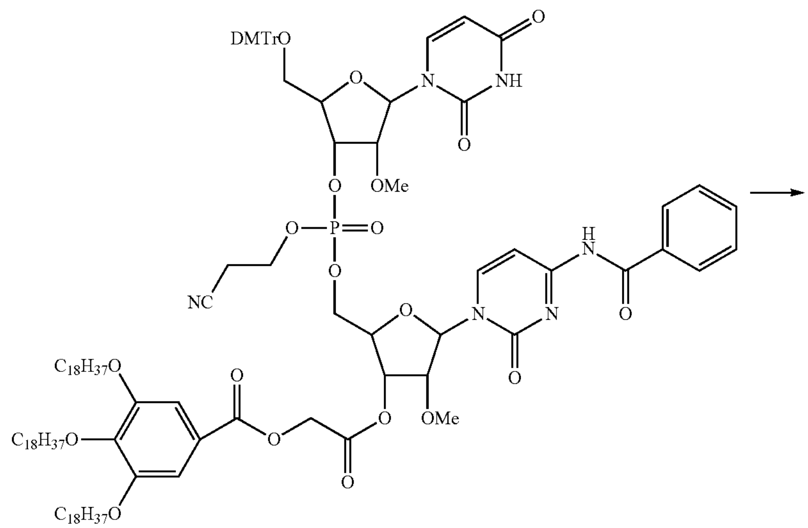

-continued

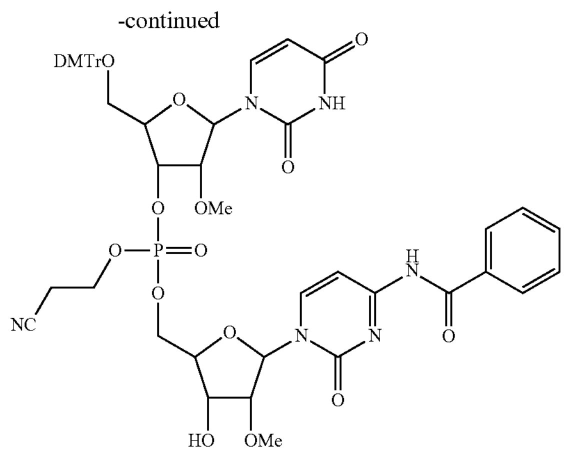

Mixture solutions of N,N-diisopropylethylamine (0.065 g, 0.50 mmol) in THF (13.5 mL) and 2-propanol (1.5 mL) were cooled from 0 to −10° C. In cool, 4 mol/L—lithium borohydride—THF solution (0.125 mL, 0.50 mmol) was added and stirred at the same temperature for 10 min. A mixture solution of $N^4$-benzoyl-5'-O-((2-cyanoethoxy) (5'-O-(4,4'-dimethoxytrityl)-2'-O-methyluridine-3'-yl)phosphoryl)-2'-O-methylcytidine-3'-yl 2-((3,4,5-tris(octadecyloxy) benzoyl)oxy)acetate (0.200 g, 0.10 mmol) in THF (0.9 mL)—2-propanol (0.1 mL) was then added and stirred at the same temperature for 0.5 hours. 10% aqueous ammonium chloride (2 mL) was added to the reaction solution, and then the mixture was separated, and the organic layer was washed with 10% brine. The organic layer was dried over anhydrous sodium sulfate, filtered to remove sodium sulfate, and then the filtrate was concentrated. The solid precipitated by adding methanol to the concentrated residue was removed by filtration, and the filtrate was concentrated and dried. The concentrated residue was purified by column chromatography (spherical neutral silica gel, eluent: dichloromethane—methanol) to give the title compound (0.055 g, 53%) as a white solid.

$^1$H-NMR (400 MHz, $CDCl_3$): δ 2.00-2.27 (brs, 2H), 2.55-2.74 (m, 1H), 2.80 (t, 1H, J=6.2 Hz), 3.14-3.41 (m, 1H), 3.44-3.92 (m, 14H), 4.03-4.64 (m, 7H), 5.12 (q, 1H, J=5.6 Hz), 5.27 (t, 1H, J=8.0 Hz), 5.87-6.05 (m, 2H), 6.78-6.89 (m, 4H), 7.19-7.64 (m, 12H), 7.76-8.16 (m, 4H), 9.05-9.42 (brs, 1H), 9.50-9.87 (b rs, 1H).

$^{13}$C-NMR (100 MHz, $CDCl_3$): δ 19.54, 19.56, 19.61, 19.64, 55.28, 55.32, 58.80, 58.82, 58.93, 61.30, 61.34, 62.38, 62.43, 62.68, 62.73, 66.03, 66.08, 66.41, 66.46, 67.85, 67.95, 74.30, 74.34, 74.42, 74.47, 81.32, 81.41, 81.49, 81.58, 81.64, 81.72, 82.17, 82.99, 83.08, 86.58, 86.79, 87.46, 87.48, 89.42, 89.51, 96.78, 102.69, 102.71, 113.39, 116.35, 116.48, 127.37, 127.42, 127.80, 127.85, 128.12, 128.25, 128.29, 128.57, 128.90, 128.93, 130.22, 130.27, 130.30, 131.01, 132.94, 133.02, 133.14, 133.17, 134.72, 134.75, 134.82, 134.84, 139.51, 139.66, 143.90, 143.97, 144.26, 150.43, 154.73, 158.81, 158.85, 162.82, 162.86, 163.22, 166.72.

TOF/MS (ESI): calcd for $C_{51}H_{53}N_6O_{16}PNa$ $[M+Na]^+$ 1059.3153, found 1059.3202.

Examples 7-8

Synthesis of 5'-O-((2-cyanoethoxy)(5'-O-(4,4'-dimethoxytrityl)-2'-O-(tert-butyldimethylsilyl)uridine-3'-yl) phosphoryl)-2'-O-(tert-butyldimethylsilyl) uridine

[Chemical Formula 103]

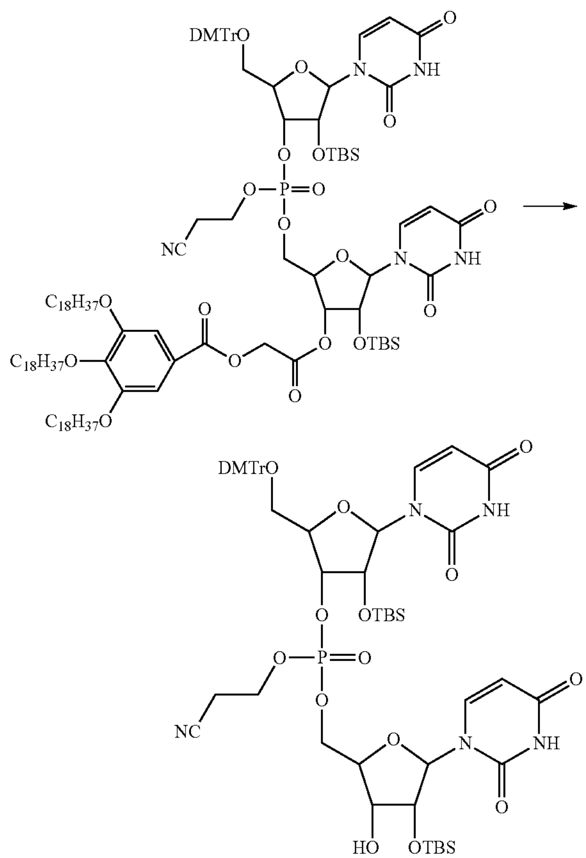

A mixture solution of 5'-O-((2-cyanoethoxy)(5'-O-(4,4'-dimethoxytrityl)-2'-O-(tert-butyldimethylsilyl)uridine-3'-yl) phosphoryl)-2'-O-(ter t-butyldimethylsilyl)uridine-3'-yl 2-((3,4,5-tris(octadecyloxy)benzoyl)oxy)acetate (0.420 g, 0.20 mmol) in THF (27 mL)—2-propanol (3 mL) was cooled to 0 to −10° C. In cool, 4 mol/L—lithium borohydride—THF solution (0.25 m L, 1.00 mmol) was added and then stirred at the same temperature for 1.5 h. 10% aqueous ammonium chloride (4 mL) was added to the reaction solution, and then the mixture was separated, and the organic layer was washed with 10% brine. The organic layer was dried over anhydrous sodium sulfate, filtered to remove sodium sulfate, and then the filtrate was concentrated. The solid precipitated by adding methanol to the concentrated residue was removed by filtration, and the filtrate was concentrated and dried. The concentrated residue was purified by column chromatography (spherical neutral silica gel, eluent: dichloromethane—methanol) to give the title compound (0.135 g, 60%) as a white solid.

$^1$H-NMR (400 MHz, $CDCl_3$): δ 0.11-0.15 (m, 12H), 0.89-0.93 (m, 18H), 1.66-1.84 (brs, 2H), 2.50-2.77 (m, 3H), 3.46-3.67 (m, 2H), 3.80 (s, 6H), 3.98-4.55 (m, 9H), 4.92-4.96 (m, 1H), 5.23-5.27 (m, 1H), 5.61-5.75 (m, 2H), 5.97-6.00 (m, 1H), 6.84-6.87 (m, 4H), 7.14-7.45 (m, 10H), 7.77-7.87 (m, 1H), 9.00-9.50 (b rs, 2H).

$^{13}$C-NMR (100 MHz, $CDCl_3$): δ −5.14, −4.98, −4.96, −4.90, −4.82, −4.76, −4.74, −4.70, −4.68, 17.96, 18.02, 18.06, 19.54, 19.60, 19.67, 25.56, 25.60, 25.66, 25.69, 55.31, 62.02, 62.29, 62.34, 62.52, 62.57, 62.62, 67.06, 67.12, 67.32, 69.38, 69.54, 70.49, 70.93, 73.61, 74.57, 74.63, 74.71, 74.88, 81.55, 81.60, 81.73, 81.84, 81.93, 82.01, 87.37, 87.65, 87.85, 87.95, 88.05, 91.58, 91.81, 93.18, 93.89, 102.60, 102.67, 102.76, 102.82, 102.86, 113.41, 116.26, 116.30, 127.41, 127.45, 128.13, 128.17, 128.21, 130.16, 130.23, 130.29, 130.34, 134.65, 134.69, 134.72, 134.75, 139.67, 139.75, 140.36, 140.40, 141.65, 141.77, 143.99, 144.03, 149.97, 150.09, 150.19, 150.40, 150.55, 150.75, 158.83, 158.88, 162.93, 163.00, 163.18.

TOF/MS (ESI): calcd for $C_{54}H_{72}N_5O_{16}Si_2PNa$ $[M+Na]^+$ 1156.4148, found 1156.4148.

Synthesis of 5'-O-((2-Cyanoethoxy)(5'-O-(4,4'-Dimethoxytrityl)Thymidine-3'-Yl)Phosphoryl)Thymidine

Examples 7-9

(1) Synthesis from 5'-O-((2-Cyanoethoxy)(5'-O-(4,4'-Dimethoxytrityl)Thymidine-3'-Yl)Phosphoryl)Thymidine-3'-Yl 3-((3,4,5-Tris(Octadecyloxy)Benzoyl)Oxy)Propionate

[Chemical Formula 104]

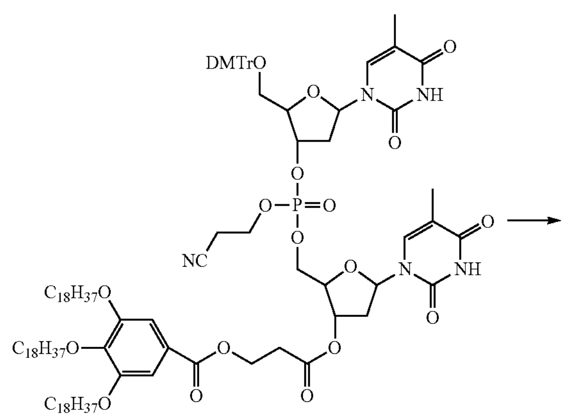

-continued

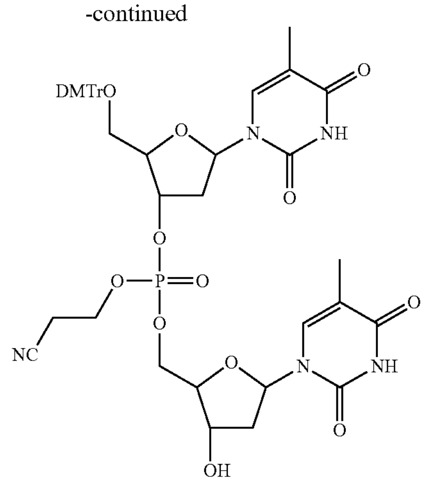

The title compound (0.136 g, 76%) was obtained as a white solid from 5'-O-((2-cyanoethoxy)(5'-O-(4,4'-dimethoxytrityl)thymidine-3'-yl)phosphoryl)thymidine-3'-yl 3-((3,4,5-tris(octadecyloxy)benzoyl)ox y)propionate (0.377 g, 0.200 mmol) according to the method of Examples 7-8.

$^1$H-NMR (400 MHz, $CDCl_3$): δ 1.41 (d, 3H, J=5.4 Hz), 1.87 (d, 3H, J=2.0 Hz), 2.19-2.27 (m, 1H), 2.34-2.48 (m, 2H), 2.62-2.77 (m, 3H), 3.39 (t, 1H, J=7.2 Hz), 3.47-3.52 (m, 1H), 3.78 (s, 6H), 4.07-4.55 (m, 8H), 5.12-5.18 (m, 1H), 6.18-6.24 (m, 1H), 6.35-6.40 (m, 1H), 6.84 (d, 4H, J=8.8 Hz), 7.21-7.31 (m, 8H), 7.32-7.38 (m, 2H), 7.51-7.58 (m, 1H), 9.92-10.14 (m, 2H).

$^{13}$C-NMR (100 MHz, $CDCl_3$): δ 11.78, 12.45, 12.49, 19.59, 19.67, 19.71, 38.83, 39.01, 39.61, 39.67, 55.31, 62.45, 62.50, 62.60, 62.65, 63.31, 67.74, 70.84, 80.08, 84.40, 84.50, 85.60, 87.30, 87.36, 111.23, 111.34, 111.91, 112.00, 113.37, 116.49, 116.74, 127.32, 128.10, 130.11, 130.14, 134.98, 135.01, 135.04, 135.19, 136.00, 144.01, 144.06, 150.69, 151.00, 151.05, 158.80, 163.96, 164.16.

TOF/MS (ESI): calcd for $C_{44}H_{48}N_5O_{14}PNa$ $[M+Na]^+$ 924.2833, found 924.2836.

Examples 7-10

(2) Synthesis from 5'-O-((2-Cyanoethoxy)(5'-O-(4,4'-Dimethoxytrityl)Thymidine-3'-Yl)Phosphoryl)Thymidine-3'-Yl 2-(N-Methyl-3,4,5-Tris(Octadecyloxy)Benzamide)Acetate

[Chemical Formula 105]

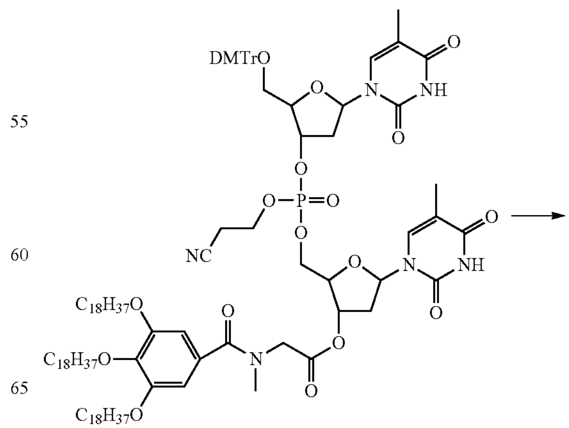

-continued

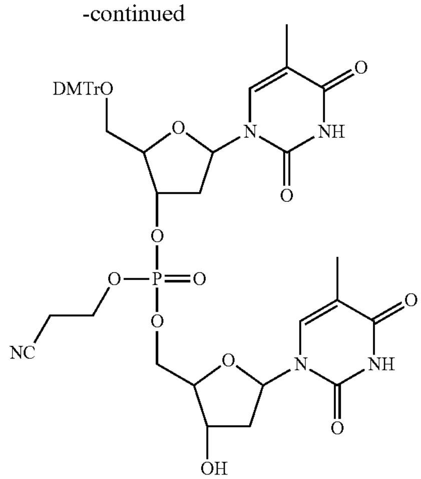

-continued

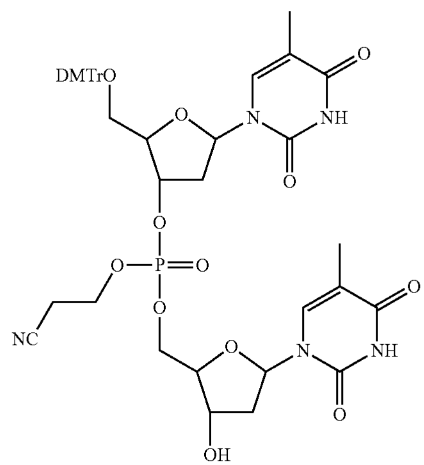

A mixture solution of 5'-O-((2-cyanoethoxy)(5'-O-(4,4'-dimethoxytrityl) thymidine-3'-yl)phosphoryl)thymidine-3'-yl 2-(N-methyl-3,4,5-tris (octadecyloxy)benzamido)acetate (189 mg, 0.10 mmol) in THF (9 mL)—2-propanol (1 mL) was cooled to 0° C. In cool, 4 mol/L—lithium borohydride—THF solution (0.125 m L, 0.50 mmol) was added and stirred at the same temperature for 30 min. An aqueous ammonium chloride solution was added to the reaction solution, and then extracted 3 times with dichloromethane. The organic layer was washed with brine, dried over anhydrous sodium sulfate, filtered to remove sodium sulfate, and then the filtrate was concentrated. The solid precipitated by suspending the concentrated residue in acetonitrile was removed by filtration, and the filtrate was concentrated. The concentrated residue was purified by column chromatography (silica gel, eluent: chloroform—methanol) to give the title compound (89 mg, 98%) as a white solid.

TOF/MS (ESI): calcd for $C_{44}H_{48}N_5O_{14}PNa$ [M+Na]$^+$ 924.3, found 924.2.

Example 7-11

(3) Synthesized from 5'-O-((2-Cyanoethoxy)(5'-O-(4,4'-Dimethoxytrityl) Thymidine-3'-Yl)Phosphoryl) Thymidine-3'-Yl 3-(3,4,5-Tris(Octadecyloxy)Benzamide)Propionate

[Chemical Formula 106]

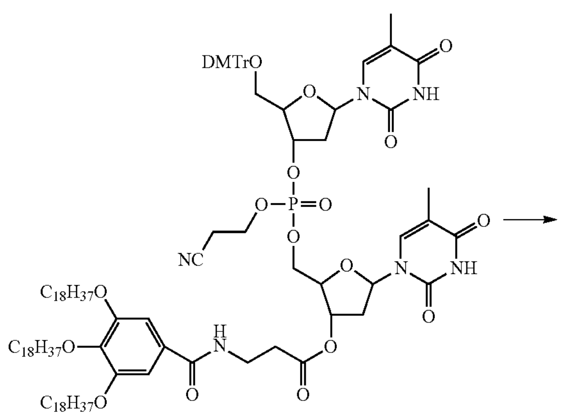

A mixture solution of 5'-O-((2-cyanoethoxy)(5'-O-(4,4'-dimethoxytrityl) thymidine-3'-yl)phosphoryl)thymidine-3'-yl 3-(3,4,5-tris(octadecyloxy)benzamide)propionate (189 mg, 0.10 mmol) in THF (9 mL)—2-propanol (1 mL) was cooled to 0° C. In cool, 4 mol/L—lithium borohydride—THF solutions (0.125 mL, 0.50 mmol) were added, and then stirred at room temperature for 1 hours. An aqueous ammonium chloride solution was added to the reaction solution, and then extracted 3 times with dichloromethane. The organic layer was washed with brine, dried over anhydrous sodium sulfate, filtered to remove sodium sulfate, and then the filtrate was concentrated. The solid precipitated by suspending the concentrated residue in acetonitrile was removed by filtration, and the filtrate was concentrated. The concentrated residue was purified by column chromatography (silica gel, eluent: chloroform—methanol) to give the title compound (74 mg, 82%) as a white solid.

TOF/MS (ESI): calcd for $C_{44}H_{48}N_5O_{14}PNa$ [M+Na]$^+$ 924.3, found 924.2.

Example 7-12
Synthesis of (6-($N^6$-Benzoyladenine-9-Yl)-4-Trityl-Morpholin-2-Yl)Methyl P-(2-(Hydroxymethyl)-6-Thymine-1-Yl)Morpholino)-N,N-Dimethylphosphonoamidate
[Chemical Formula 107]
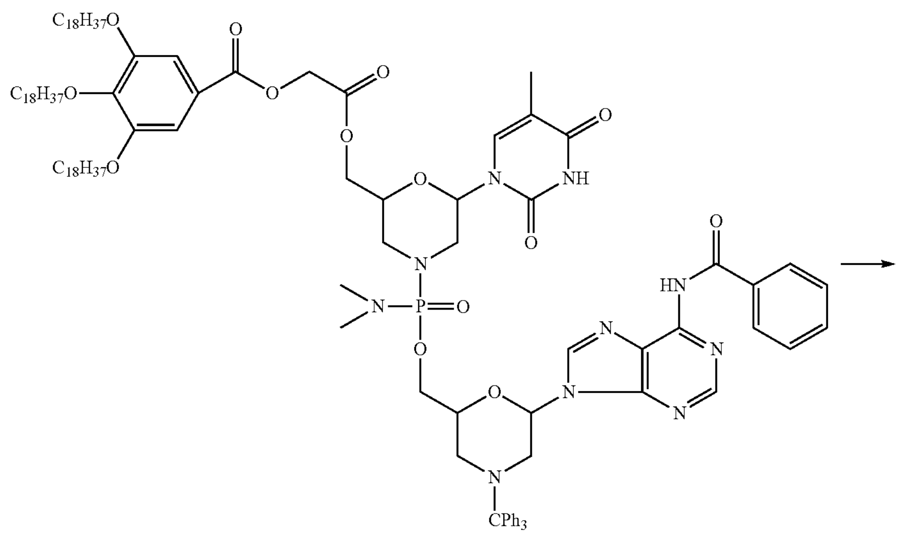
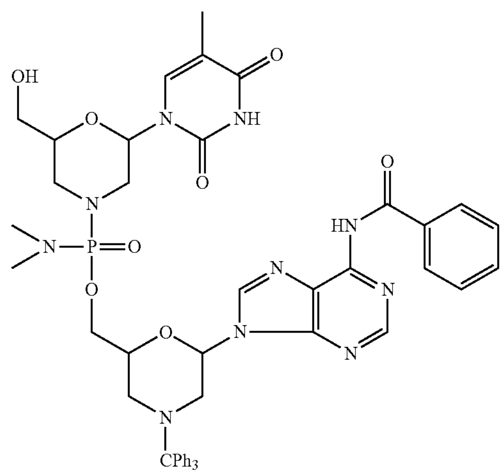

The title compound (0.114 g, 61%) was obtained as a white solid from (4-((6-($N^6$-benzoyladenine-9-yl)-4-tritylmorpholin-2-yl)methoxy) (dimethylamino)phosphoryl)-6-(thymine-1-yl)morpholin-2-yl)methyl 2-((3,4,5-tris(octadecyloxy)benzoyl)oxy)acetate (0.379 g, 0.20 mmol) according to the procedure of Examples 7-7.

$^1$H-NMR (400 MHz, $CDCl_3$): δ 0.87-1.95 (m, 6H), 2.01 (s, 1H), 2.45-2.64 (m, 7H), 3.06-4.04 (m, 9H), 4.43-4.46 (m, 1H), 5.52 (d d, 1H, J=2.4, 10.4 Hz), 6.41 (dt, 1H, J=2.4, 10.0 Hz), 7.05-7.64 (m, 19H), 8.03 (d, 2H, J=8.4 Hz), 8.09 (s, 1H), 8.71-8.80 (m, 1H), 9.69-9.78 (m, 1H), 10.28 (s, 1H), 10.75-11.05 (brs, 1H).

$^{13}$C-NMR (100 MHz, $CDCl_3$): δ 12.41, 12.45, 36.54, 36.58, 36.62, 36.66, 44.61, 44, 82, 47.13, 48.68, 48.78, 52.80, 52.85, 62.72, 62.78, 65.46, 65.61, 75.07, 75.14, 75.45, 75.52, 78.06, 78.13, 78.27, 78.33, 79.60, 79.65, 80.01, 80.49, 110.96, 111.03, 122.47, 122.78, 126.65, 128.00, 128.24, 128.41, 128.49, 128.62, 129.17, 132.61, 132.69, 133.48, 133.64, 134.86, 134.96, 140.94, 149.54, 149.75, 149.82, 150.02, 151.23, 151.42, 152.66, 152.75, 163.75, 163.79, 165.25.

TOF/MS (ESI): calcd for $C_{48}H_{51}N_{10}O_8PNa$ $[M+Na]^+$ 949.3527, found 949.3545.

Example 7-13

Synthesis of (6-($N^4$-Benzoylcytosine-1-Yl)-4-Tritylmorpholin-2-Yl)Methyl P-(2-(Hydroxymethyl)-6-($N^2$-Isobutyrylguanine-9-Yl)Morpholino)-N,N-Dimethylphosphonoamidate

[Chemical Formula 108]

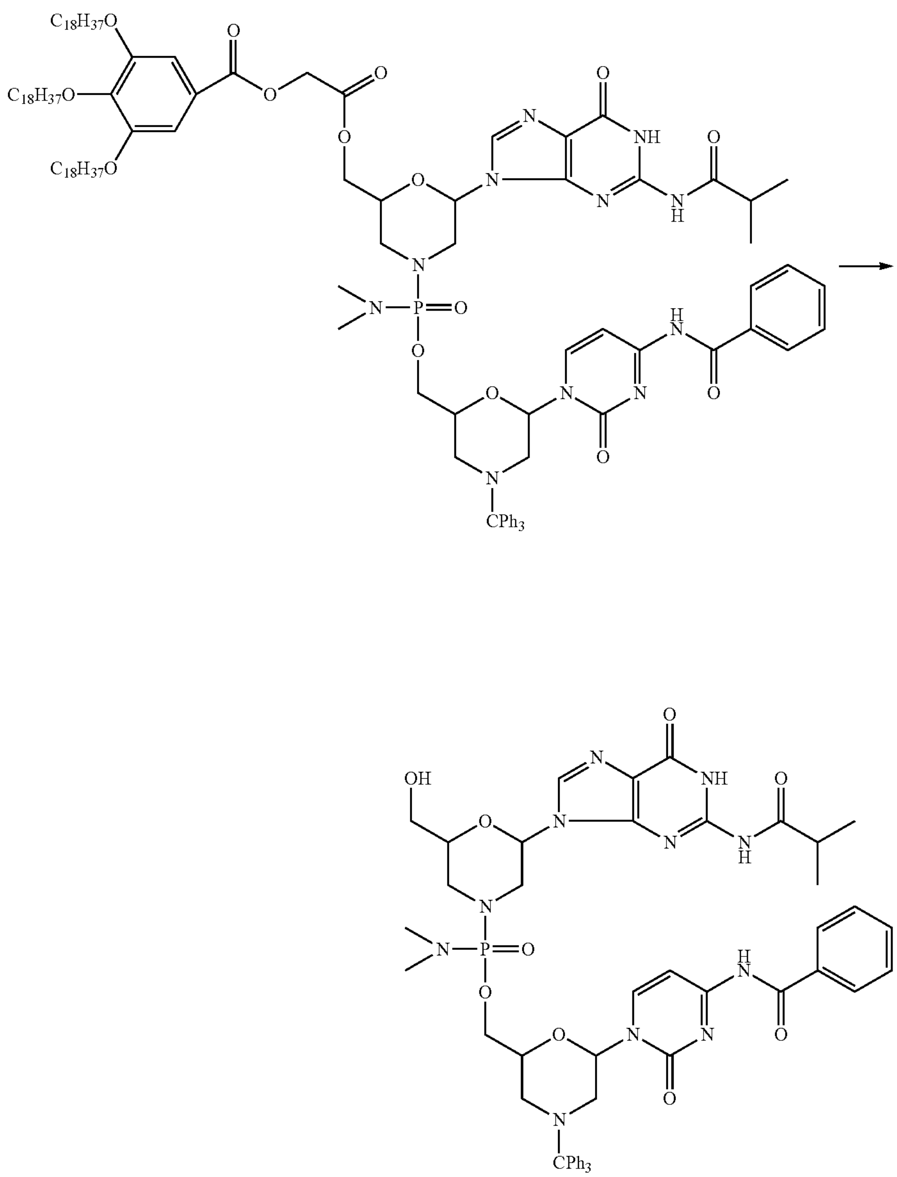

The title compound (0.052 g, 52%) was obtained as a white solid from (4-(((6-($N^4$-benzoylcytosine-1-yl)-4-tritylmorpholin-2-yl)methoxy) (dimethylamino)phosphoryl)-6-($N^2$-isobutyrylguanine-9-yl)morpholin-2-yl)methyl 2-((3,4,5-tris(octadecyloxy)benzoyl)oxy)acetate (0.197 g, 0.10 mmol) according to the methods of Examples 7-7.

$^1$H-NMR (400 MHz, $CDCl_3$): δ 0.78-1.55 (m, 9H), 2.37-2.95 (m, 8H), 3.08-3.94 (m, 9H), 4.13-4.43 (m, 2H), 5.42-5.54 (m, 1H), 6.22-6.38 (m, 1H), 7.05-7.80 (m, 19H), 7.93 (d, 2H, J=7.2H z), 9.58-9.92 (brs, 1H), 10.64-10.86 (brs, 1H), 12.05-12.21 (br s, 1H).

$^{13}$C-NMR (100 MHz, $CDCl_3$): δ 13.91, 14.12, 19.03, 19.06, 19.28, 22.69, 25.76, 28.55, 29.36, 29.70, 31.72, 31.92, 35.99, 36.05, 36.62, 36.65, 36.69, 44.63, 44.92, 47.15, 47.56, 48.44, 48.79, 52.26, 52.42, 61.85, 62.58, 62.73, 65.66, 66.15, 71.09, 71.69, 75.40, 75.86, 75.91, 78.19, 79.73, 80.56, 81.37, 81.76, 97.87, 120.56, 120.92, 126.65, 127.96, 128.04, 128.70, 128.83, 128.92, 129.13, 131.00, 132.21, 132.97, 133.02, 133.14, 136.66, 137.43, 144.02, 144.54, 147.92, 147.98, 148.00, 154.99, 155.57, 155.62, 162.69, 163.09, 167.24, 179.62, 179.86.

TOF/MS (ESI): calcd for $C_{51}H_{56}N_{11}O_9PNa$ $[M+Na]^+$ 1020.3898, found 1 020.3942.

Examples 7-14

Confirmation of De-Tagging of 8 Mer (1) Synthesis of 5'-O-((2-Cyanoethoxy)(5'-O-((2-Cyanoethoxy)(5'-O-((2-Cyanoethoxy)(5'-O-((2-Cyanoethoxy)(5'-O-((2-Cyanoethoxy)(5'-O-((2-Cyanoethoxy)(5'-O-((2-Cyanoethoxy)($N^4$-Benzoyldeoxycytidine-3'-Yl)Phosphoryl)-$N^6$-Benzoyldeoxyadenosine-3'-Yl)Phosphoryl) Thymidine-3'-Yl)Phosphoryl)-$N^2$-Isobutyryldeoxyguanosine-3'-Yl)Phosphoryl)-$N^4$-Benzoyldeoxycytidine-3'-Yl)Phosphoryl)-$N^6$-Benzoyldeoxyadenosine-3'-Yl)Phosphoryl) Thymidine-3'-Yl)Phosphoryl)Thymidine-3'-Yl 2-((3,4,5-Tris(Octadecyloxy)Benzoyl)Oxy)Acetate (8 Mer)

Under argon atmosphere, 5-benzylthio-1H-tetrazole (0.38 g, 1.96 mmol) was added to a suspension of thymidine-3'-yl 2-((3,4,5-tris (octadecyloxy)benzoyl)oxy)acetate (1.19 g, 0.98 mmol) and 5'-O-(4,4'-dimethoxytrityl) thymidine-3'-yl-phosphoroamidite (1.46 g, 1.96 mmol) in dichloromethane (10 mL), and stirred at room temperature for 1.5 hours. Next, pyridine (0.93 g, 11.77 mmol), water (0.11 g, 5.89 mmol), and iodine (1.25 g, 4.91 mmol) were added, and then stirred at room temperature for 4 hours. 1.2 mol/L-ascorbic acid aqueous solution (3 mL) was added to the reaction solution, and then stirred at room temperature for 15 minutes. The solid precipitated by dropping acetonitrile (24 mL) to the reaction solution was filtered. The solid was washed with acetonitrile—dichloromethane mixture solvent, and then dried under reduced pressure at 50° C. to obtain a DMTr (2.22 g)

Next, pyrrole (0.33 g, 4.91 mmol) and trifluoroacetic acid (0.13 g, 1.18 mmol) were added to a suspension of DMTr (1.83 g, 0.98 mmol) in dichloromethane (15 mL), and then stirred at room temperature for 1.5 hours. The solid precipitated by dropping acetonitrile (37 mL) and methanol (18 mL) to the reaction solution was filtered. The solid was washed with acetonitrile—methanol—dichloromethane mixture solvent, and then dried under reduced pressure at 50° C. to obtain a 2 mer (1.48 g).

The same procedure as was repeated 6 times to obtain 2.94 g of 8 mer.

TOF/MS (ESI): m/z 2106.3 $[M+2H]^{2+}$, 1403.9 $[M+3H]^{3+}$.

Example 7-15

(2) De-Tagging of 5'-O-((2-Cyanoethoxy)(5'-O-((2-Cyanoethoxy) (5'-O-((2-Cyanoethoxy)(5'-O-((2-Cyanoethoxy)(5'-O-((2-Cyanoethoxy)(5'-O-((2-Cyanoethoxy)(5'-O-((2-Cyanoethoxy)($N^4$-Benzoyldeoxycytidine-3'-Yl)Phosphoryl)-$N^6$-Benzoyldeoxyadenosine-3'-Yl)Phosphoryl) Thymidine-3'-Yl)Phosphoryl)-$N^2$-Isobutyryldeoxyguanosine-3'-Yl)Phosphoryl)-$N^4$-Benzoyldeoxycytidine-3'-Yl)Phosphoryl)-$N^6$-Benzoyldeoxyadenosine-3'-Yl)Phosphoryl) Thymidine-3'-Yl)Phosphoryl)Thymidine-3'-Yl 2-((3,4,5-Tris(Octadecyloxy)Benzoyl)Oxy)Acetate N,N-Diisopropylethylamine (65 mg, 0.50 mmol) was added to a mixture solution of dichloromethane (0.4 mL), THF (0.2 mL) and 2-propanol (0.04 mL), and then cooled to 0 to −10° C. Next, 4 mol/L—lithium borohydride—THF solution (0.125 m L, 0.50 mmol) was added, and then stirred at the same temperature for 20 minutes to prepare a reducing reagent. The reducing reagents were added to a mixture of 8 mer (84 mg, 0.02 mmol) in dichloromethane (4.2 mL)—THF (1.8 mL)—2-propanol (0.4 mL) previously cooled to 0 to −10° C., and then the mixture was stirred at the same temperature for 40 minutes. 10% aqueous ammonium chloride (5 mL) was added to the reaction solution, and then was extracted with dichloromethane. The organic layer was washed with brine, and then the organic layer was concentrated to dryness. The precipitated solid was collected by suspending the concentrated residue in dichloromethane. The solid was washed with dichloromethane and dried in vacuo, and then 5'-O-((2-cyanoethoxy) (5'-O-((2-cyanoethoxy)(5'-O-((2-cyanoethoxy)(5'-O-((2-cyanoethoxy) (5'-O-((2-cyanoethoxy)(5'-O-((2-cyanoethoxy)(5'-O-((2-cyanoethoxy) ($N^4$-benzoyldeoxycytidine-3'-yl)phosphoryl)-$N^6$-benzoyldeoxyadenosine-3'-yl)phosphoryl)thymidine-3'-yl) phosphoryl)-$N^2$-isobutyryldeoxyguanosine-3'-yl) phosphoryl)-$N^4$-benzoyldeoxycytidine-3'-yl)phosphoryl)-$N^6$-benzoyldeoxyadenosine-3'-yl)phosphoryl)thymidine-3'-yl)phosphoryl)thymidine (25 mg) was obtained.

TOF/MS (ESI): m/z 1621.9 $[M+2H]^{2+}$, 1081.6 $[M+3H]^{3}$+, 811.2 $[M+4H]^{4+}$.

8. Comparison of the Rate of Progression of De-Tagging

Example 8

5'-O-(4,4'-Dimethoxytrityl)thymidine-3'-yl 2-((3,4,5-tris (octadecyloxy)benzoyl)oxy)acetate (abbreviated as A-Tag-dT-DMTr) and 3,4,5-tris(octadecyloxy)benzyl 5'-O-(4,4'-dimethoxytrityl)thymidine-3'-yl succinate (abbreviated as S-Tag-dT-DMTr) were compared for the rate of progression of de-tagging under ammonia basic conditions as shown below.

<De-tagging Conditions>

A-Tag-dT-DMTr or S-Tag-dT-DMTr 50 μmol
28% aqueous ammonia 2.0 mL
Ethanol 0.5 mL
THF 0.5 mL
Reaction temperature 35° C.

<Formation Rate of dT-DMTr (Tag-Free Form)>

TABLE 1

| | 1 hr | 2 hr | 3 hr | 4 hr | 5 hr |
|---|---|---|---|---|---|
| A-Tag-dT-DMTr | 34% | 74% | 91% | 98% | 100% |
| S-Tag-dT-DMTr | 0% | 2% | 3% | 4% | 5% |

<HPLC Condition>

Columns: Inertsil WP 300 Diol (5 μm, 4.6ϕ×150 mm)

Flow rate: 1.0 mL/min

Mobile phase: n-hexane, $CHCl_3$-MeOH (1/1)

Gradient: 0-11 min; 5 to 30% ($CHCl_3$-MeOH)

Detection method: UV (λ=254 nm)

Retention time: A-Tag-dT-DMTr: Rt=4.23 min, S-Tag-dT-DMTr: Rt=4.17 min, dT-DMTr: Rt=9.40 min Production rate: (dT-DMTr)/[(A-Tag-dT-DMTr or S-Tag-dT-DMT r)+(dT-DMTr)]

As described above, we confirmed that A-Tag is more rapidly de-Tagged than succinate esters in common deprotection conditions for oligonucleic acid synthesis.

9. Summary of Synthesis Examples

Hereinafter, those summarizing the synthesis examples in each of the above-described examples will be described.

9.1 Synthesis of the 3 Mer

TABLE 2

Synthesis of the 3 mer

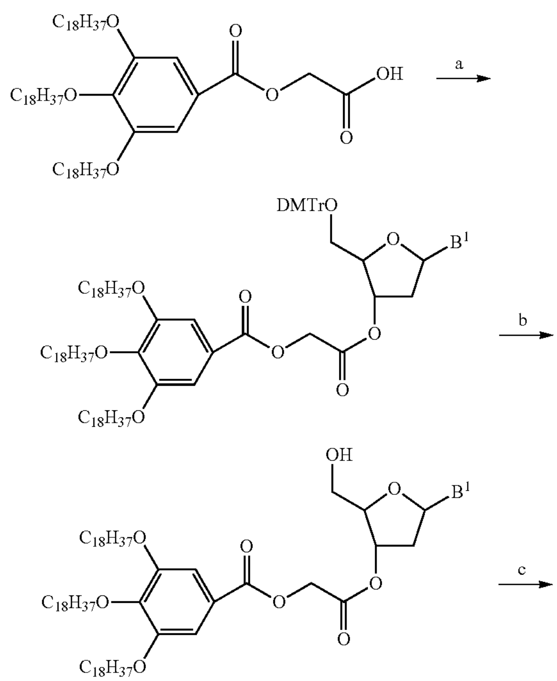

TABLE 2-continued

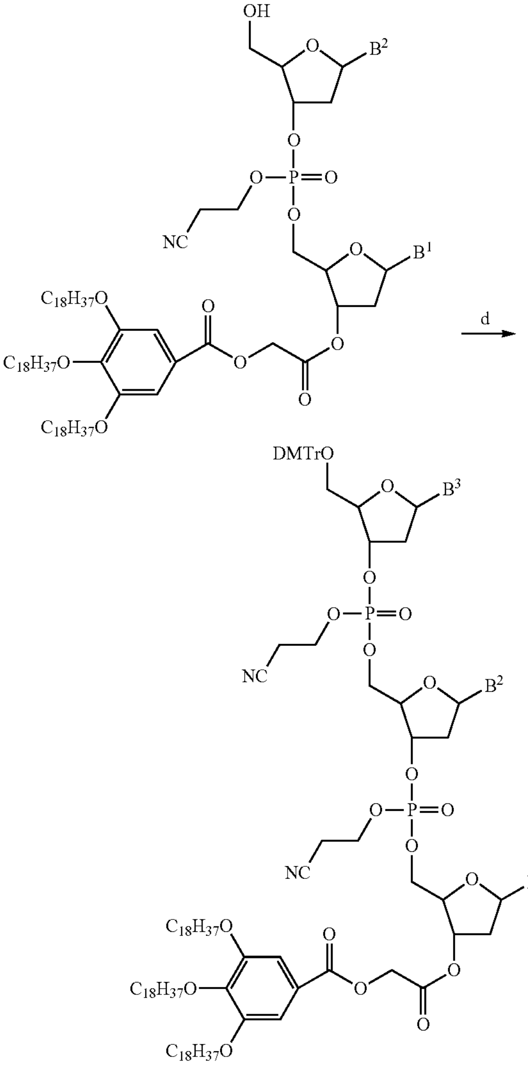

| sequence | | | | Yield (%) | | | | |
|---|---|---|---|---|---|---|---|---|
| 5' → 3' | B1 | B2 | B3 | a | b | c | d | total |
| TGT | T | $G^{Bu}$ | T | 95% | 91% | 98% | 90% | 76% |
| GTA | $A^{Bz}$ | T | $G^{Bu}$ | 96% | 92% | 97% | 94% | 81% |
| TGC | $C^{Bz}$ | $G^{Bu}$ | T | 97% | 97% | 99% | 89% | 83% |
| TTG | $G^{Bu}$ | T | T | 98% | 98% | 94% | 89% | 80% |

As shown in Table 2 above, various Tag-conjugated 3 mer DNA oligomers could be obtained in high yields.

9.2 Synthesis of the Dimer

TABLE 3

Synthesis of the dimer

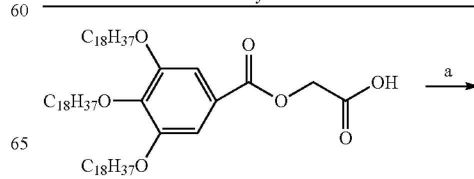

TABLE 3-continued

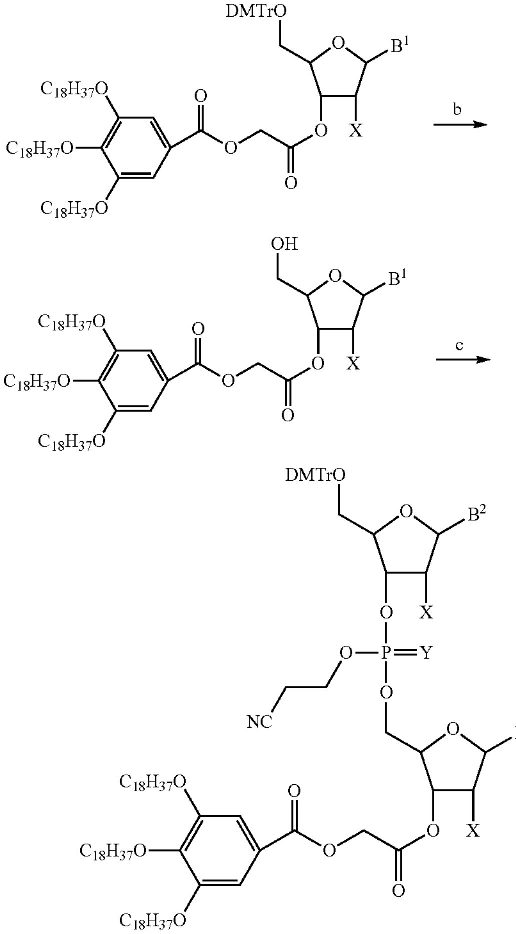

| sequence | | | | | Yield (%) | | | |
|---|---|---|---|---|---|---|---|---|
| 5' → 3' | X | Y | B1 | B2 | a | b | c | total |
| TT (P = S) | H | S | T | T | 95% | 91% | 96% | 83% |
| UU (TBS) | OTBS | O | U | U | 68% | 97% | 92% | 61% |
| UC (OMe) | OMe | O | $C^{Bz}$ | U | 91% | 99% | 70% | 63% |
| UG (F) | F | O | $G^{Bu}$ | U | 96% | 98% | 93% | 87% |

As shown in Table 3 above, various Tag-conjugated oligonucleotides (dimers) were obtained in high yields.

9.3 Synthesis of the Dimer

TABLE 4

Synthesis of the dimer

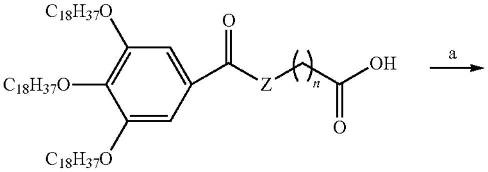

TABLE 4-continued

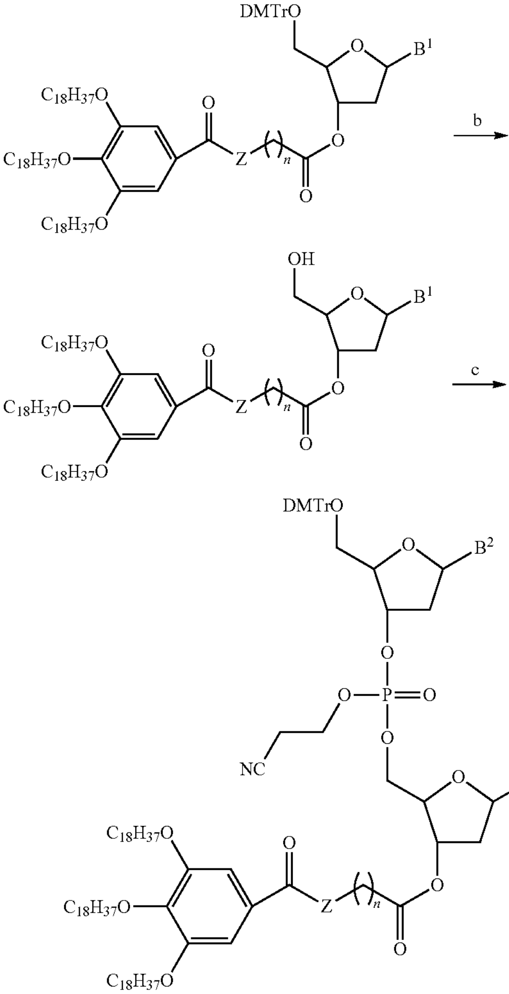

| sequence | | | | | Yield (%) | | | |
|---|---|---|---|---|---|---|---|---|
| 5' → 3' | Z | n | B1 | B2 | a | b | c | total |
| TT | O | 2 | T | T | 18% | | 96% | 17% |
| TT | N—Me | 1 | T | T | 78% | 98% | 96% | 73% |
| TT | N—H | 2 | T | T | 60% | 99% | 95% | 56% |

As shown in Table 4 above, various Tag-conjugated oligonucleotides (dimers) were obtained in high yields.

9.4 Synthesis of the Dimer

TABLE 5

Synthesis of the dimer

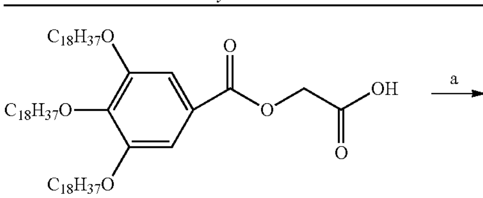

TABLE 5-continued
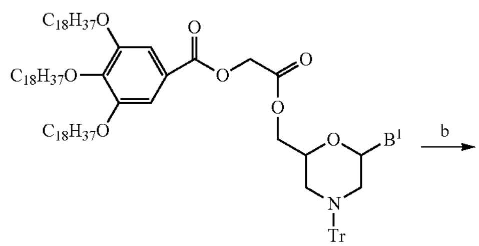
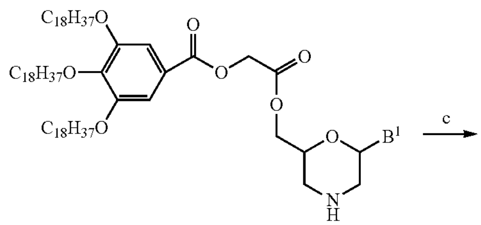
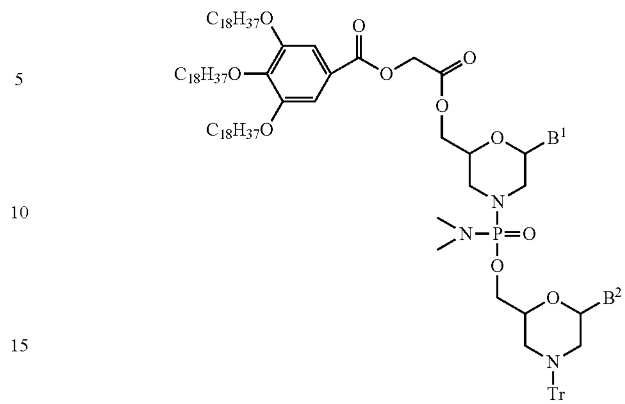
| sequence | | | Yield (%) | | | |
|---|---|---|---|---|---|---|
| 5' → 3' | B1 | B2 | a | b | c | total |
| TA | T | $A^{Bz}$ | 98% | 97% | 59% | 56% |
| GC | $G^{Bu}$ | $C^{Bz}$ | 97% | 96% | 91% | 85% |
As shown in Table 5 above, various Tag binding oligonucleotides (dimers) were obtained in high yields.
9.5 Synthesis and Deprotection of 20 Mers
Chemical Formula 109
Synthesis and Total Deprotection of 20 Mers
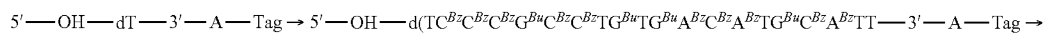
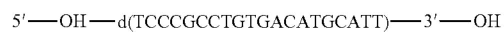

By using the alkoxyphenyl derivative of the present invention and the Tagged protected nucleotide, the Tagged protected oligonucleotide (20 mer) could be easily obtained. Moreover, by removing Tag moieties as well as protecting groups, oligonucleotides could be conveniently obtained.

9.6 de-Tag of the 3 Mer

TABLE 6 de-Tag of the 3 mer

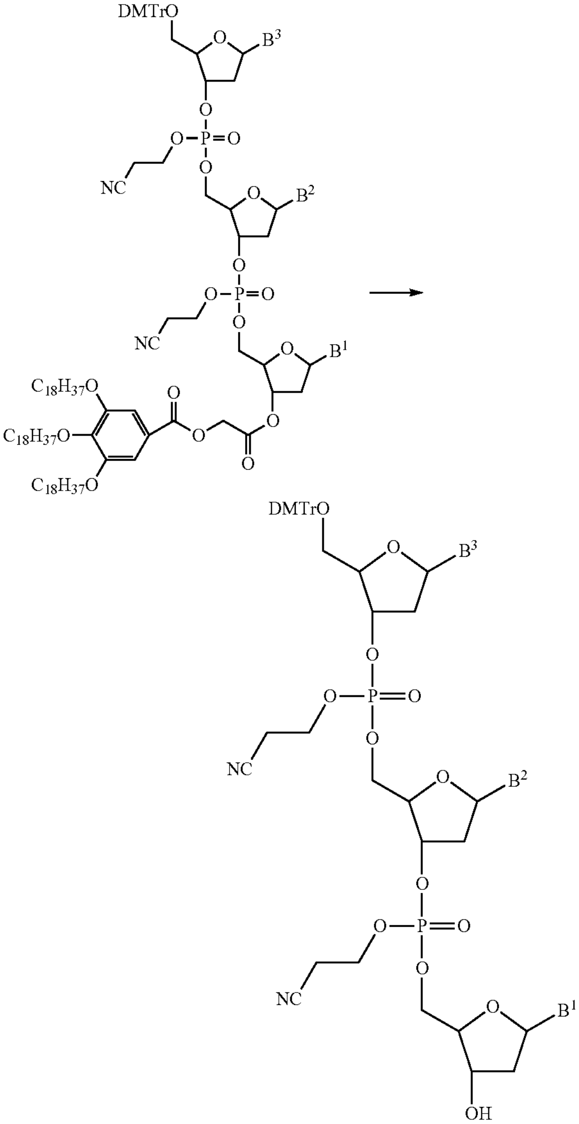

| sequence 5' → 3' | B1 | B2 | B3 | Reductant | Base | Yield |
|---|---|---|---|---|---|---|
| TGT | T | $G^{Bu}$ | T | $LiBH_4$ | — | 95% |
| GTA | $A^{Bz}$ | T | $G^{Bu}$ | $LiBH_4$ | — | 75% |
| TGC | $C^{Bz}$ | $G^{Bu}$ | T | $LiBH_4$ | — | 79% |
| TTG | $G^{Bu}$ | T | T | $LiBH_4$ | — | 93% |

De-Tag of the 3Mer

As shown in Table 6 above, Tag moieties of various Tagged protected oligonucleotides (3 mers) were removed, and each protected oligonucleotide (3 mer) could be obtained in high yield.

9.7 de-Tag of the Dimer

TABLE 7 de-Tag of the dimer

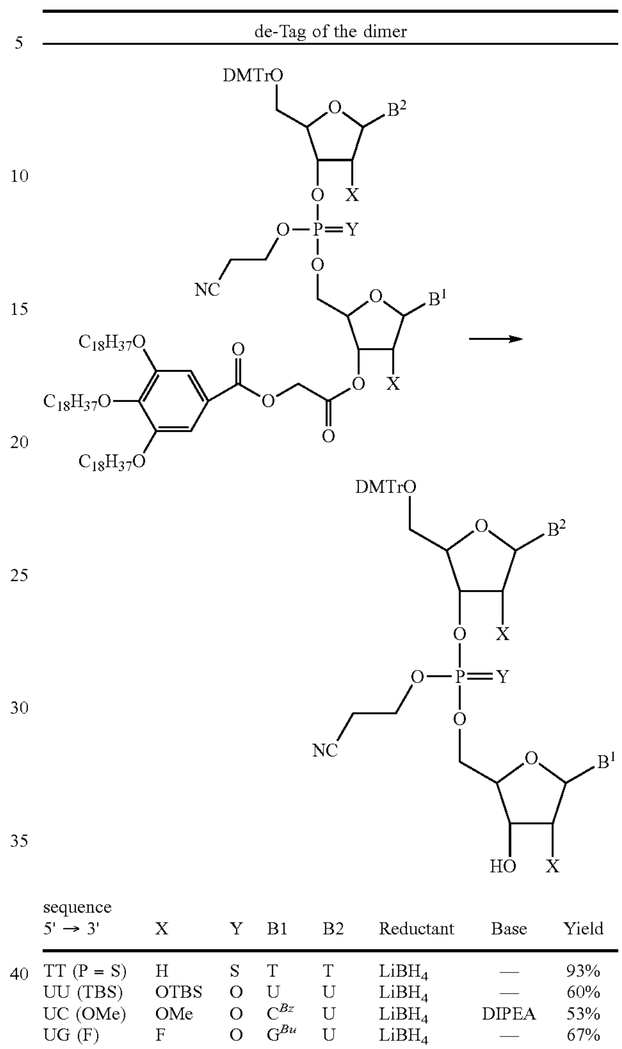

| sequence 5' → 3' | X | Y | B1 | B2 | Reductant | Base | Yield |
|---|---|---|---|---|---|---|---|
| TT (P = S) | H | S | T | T | $LiBH_4$ | — | 93% |
| UU (TBS) | OTBS | O | U | U | $LiBH_4$ | — | 60% |
| UC (OMe) | OMe | O | $C^{Bz}$ | U | $LiBH_4$ | DIPEA | 53% |
| UG (F) | F | O | $G^{Bu}$ | U | $LiBH_4$ | — | 67% |

As shown in Table 7 above, the Tag moieties of the various Tagged protected oligonucleotides (dimers) were removed and each protected oligonucleotide (dimer) was obtained in high yield.

9.8-De-Tag of the Dimer

TABLE 8 de-Tag of the dimer

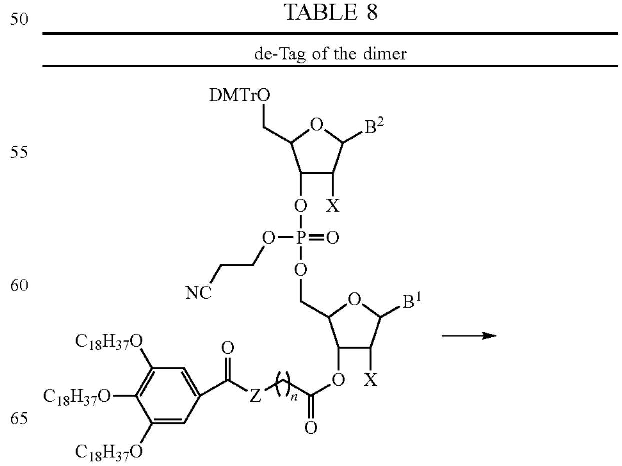

TABLE 8-continued

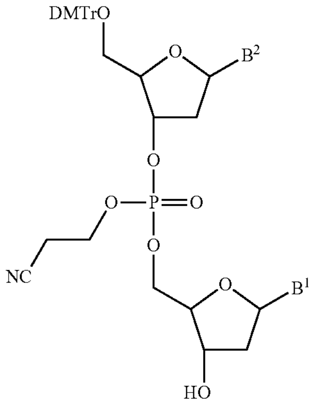

| sequence 5' → 3' | Z | n | B1 | B2 | Reductant | Base | Yield |
|---|---|---|---|---|---|---|---|
| TT | O | 2 | T | T | $LiBH_4$ | — | 76% |
| TT | N—Me | 1 | T | T | $LiBH_4$ | — | 98% |
| TT | N—H | 2 | T | T | $LiBH_4$ | — | 82% |

As shown in Table 8 above, the Tag moieties of the various Tagged protected oligonucleotide (dimers) were removed and each protected oligonucleotide (dimer) was obtained in high yield.

9.9 De-Tag of the Dimer

TABLE 9 de-Tag of the dimer

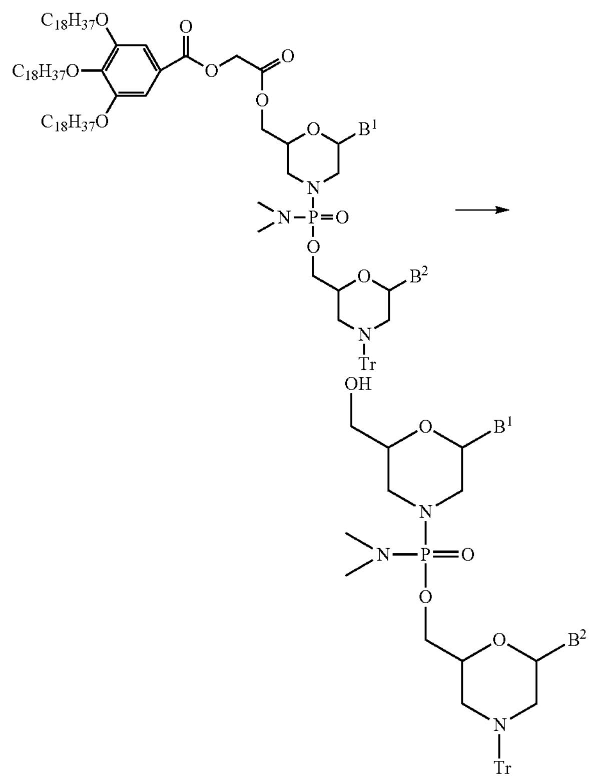

TABLE 9-continued

| sequence 5' → 3' | B1 | B2 | Reductant | Base | Yield |
|---|---|---|---|---|---|
| TA | T | $A^{Bz}$ | $LiBH_4$ | DIPEA | 61% |
| GC | $G^{Bu}$ | $C^{Bz}$ | $LiBH_4$ | DIPEA | 52% |

As shown in Table 9 above, the Tag moieties of the various Tagged protected oligonucleotides (dimers) were removed and each protected oligonucleotide (dimer) was obtained in high yield.

INDUSTRIAL APPLICABILITY

The alkoxyphenyl derivative of the present invention is available for the production of the Tagged protected nucleosides and Tagged protected nucleotides and the like. Also, a method for producing an oligonucleotide, such as a Tagged protected nucleoside and a Tagged protected nucleotide of the present invention, and a method for selective Tag moiety removal of a Tagged protected nucleoside or a Tagged protected nucleotide are available for the synthesis of protected oligo nucleotides, particularly in liquid phase synthesis (including pseudo-liquid phase synthesis). All of these are very useful compounds and methods for nucleic acid drug development, biological mechanism elucidation, and the like.

The invention claimed is:

1. A compound of general formula (3) or a derivative thereof:

(3)

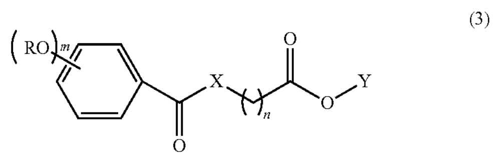

wherein: R each independently is an optionally substituted alkyl group having 10 to 40 carbon atoms; m is an integer between 1 and 5, wherein if m is 2 or more, a plurality of ROs may be the same or different; X is O, or S; n is an integer from 1 to 4; Y is the following general formula (4) or general formula (5):

(4)

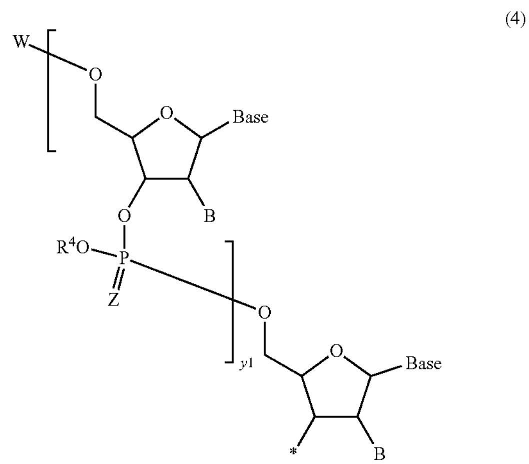

wherein for formula (4):

Base is a nucleobase which may be modified, wherein if 2 or more Bases are present, a plurality of Bases present may be the same or different; B is a hydrogen atom, an optionally protected hydroxyl group, or a halogen, wherein if 2 or more Bs are present, a plurality of Bs present may be the same or different; W is a hydrogen atom or protecting group; $R^4$ is an alkyl group having 1 to 4 carbons and having an electron withdrawing group, wherein if 2 or more $R^4$s are present, a plurality of R4s present may be the same or different; Z represents is O or S, wherein if 2 or more Zs are present, a plurality of Zs present may be the same or different; y1 is any integer greater than or equal to 0; and * is a bonding position in the above general formula (3);

(5)

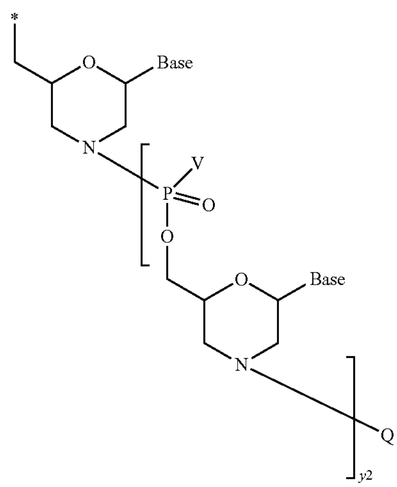

wherein for formula (5):

Base is a nucleobase which may be modified, wherein if 2 or more Bases are present, a plurality of Bases present may be the same or different; Q is a hydrogen atom or protecting group; V is an alkoxy group having 1 to 6 carbon atoms, a di(C-alkyl)amino group, or a piperazino group in which the nitrogen atom at the 4-position is protected with a protecting group and may be further substituted, wherein if 2 or more Vs are present, a plurality of Vs present may be the same or different; y2 is any integer greater than or equal to 0; and * is a bonding position in the above general formula (3).

2. The compound according to claim 1 or a derivative thereof, which is of general formula (6):

(6)

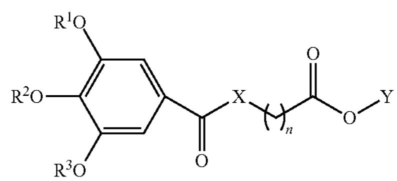

wherein:

each R1, R2, and R3 is independently an optionally substituted alkyl group having 10 to 40 carbons;

X is O, or S; n is an integer from 1 to 4; Y is the following general formula (4) or general formula (5):

(4)

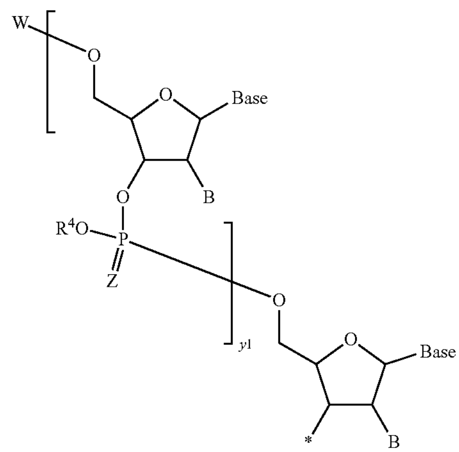

wherein for formula (4):

Base represents is a nucleobase which may be modified, wherein if 2 or more Bases are present, a plurality of Bases present may be the same or different; B is a hydrogen atom, an optionally protected hydroxyl group, or a halogen, wherein if 2 or more Bs are present, a plurality of Bs present may be the same or different; W is a hydrogen atom or protecting group; $R^4$ is alkyl group having 1 to 4 carbons and having an electron: withdrawing group, wherein if 2 or more $R^4$s are present, a plurality of $R^4$s may be the same or different; Z is O or S, wherein if 2 or more Zs are present, a plurality of Zs present may be the same or different; y1 represents is any integer greater than or equal to 0; and * represents is a bonding position in the above general formula (6);

(5)

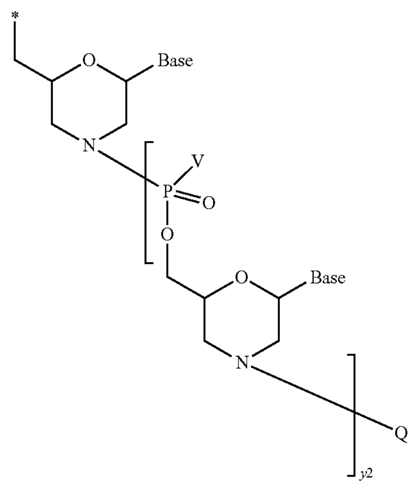

herein for formula (5):

Base is a nucleobase which may be modified, wherein if 2 or more Bases are present, a plurality of Bases present may be the same or different; Q is a hydrogen atom or protecting group; V is an alkoxy group having 1 to 6 carbon atoms, a di(C-alkyl)amino group, or a piperazino group in which the nitrogen atom at the 4-position is protected with a protecting group and may be further substituted, wherein if 2 or more Vs are present, a plurality of Vs present may be the same or different; y2 is any integer greater than or equal to 0; and * is a bonding position in the above general formula (6).

3. The compound or a derivative thereof as claimed in claim 1, wherein W is a hydrogen atom, a trityl group, a di ($C_{1-6}$ alkoxy)trityl group, a mono ($C_{1-18}$ alkoxy)trityl group, a 9-(9-phenyl)xanthenyl group, or a 9-(9-phenyl)thioxanthenyl group.

4. The compound or a derivative thereof according to claim 1, wherein $R^4$ is an ethylic group having an electron-withdrawing group at the 2-position.

5. The compound or a derivative thereof according to claim 1, wherein Q is a hydrogen atom, a trityl group, a di($C_{1-6}$ alkoxy)trityl group, a mono($C_{1-18}$ alkoxy)trityl group, a 9-(9-phenyl)xanthenyl group, or a 9-(9-phenyl)thioxanthenyl group.

6. The compound or a derivative thereof according to claim 1, wherein y1 or y2 is 1 to 100.

7. The compound or a derivative thereof according to claim 1, wherein y1 or y2 is 1 to 30.

8. The compound or a derivative thereof according to claim 1, wherein y1 or y2 is 0.

9. The compound or a derivative thereof according to claim 1, wherein n is 1 or 2.

10. The compound or a derivative thereof according to claim 1, wherein m is an integer of 2 to 4.

* * * * *